(12) United States Patent
Goldstein et al.

(10) Patent No.: US 9,376,438 B2
(45) Date of Patent: Jun. 28, 2016

(54) PYRAZOLOPYRIMIDINE DERIVATIVES AS TYROSINE KINASE INHIBITORS

(75) Inventors: David Michael Goldstein, Redwood City, CA (US); Kenneth Albert Brameld, Menlo Park, CA (US)

(73) Assignee: Principia Biopharma, Inc., South San Francisco, CA (US)

(*) Notice: Subject to any disclaimer, the term of this patent is extended or adjusted under 35 U.S.C. 154(b) by 177 days.

(21) Appl. No.: 14/117,927

(22) PCT Filed: May 16, 2012

(86) PCT No.: PCT/US2012/038135
§ 371 (c)(1),
(2), (4) Date: Apr. 16, 2014

(87) PCT Pub. No.: WO2012/158795
PCT Pub. Date: Nov. 22, 2012

(65) Prior Publication Data
US 2014/0221398 A1 Aug. 7, 2014

Related U.S. Application Data

(60) Provisional application No. 61/486,933, filed on May 17, 2011.

(51) Int. Cl.
| | | |
|---|---|---|
| *C07D 487/04* | (2006.01) | |
| *A61K 31/519* | (2006.01) | |
| *A61P 35/00* | (2006.01) | |
| *A61P 35/02* | (2006.01) | |
| *A61P 35/04* | (2006.01) | |
| *A61P 29/00* | (2006.01) | |
| *A61P 19/02* | (2006.01) | |
| *A61P 11/06* | (2006.01) | |
| *A61P 17/06* | (2006.01) | |

(52) U.S. Cl.
CPC .................... *C07D 487/04* (2013.01)

(58) Field of Classification Search
CPC ............................ C07D 487/04; A61K 31/519
See application file for complete search history.

(56) References Cited

U.S. PATENT DOCUMENTS

| | | |
|---|---|---|
| 4,721,710 A | 1/1988 | Bernhart et al. |
| 4,861,760 A | 8/1989 | Mazuel et al. |
| 4,911,920 A | 3/1990 | Jani et al. |
| 5,212,162 A | 5/1993 | Missel et al. |
| 5,403,841 A | 4/1995 | Lang et al. |
| 5,514,711 A | 5/1996 | Kitano et al. |
| 5,792,771 A | 8/1998 | App et al. |
| 6,410,486 B2 | 6/2002 | Wetterich et al. |
| 6,660,744 B1 | 12/2003 | Hirst et al. |
| 7,217,682 B2 | 5/2007 | Mori |
| 7,700,648 B2 | 4/2010 | Mori |
| 2003/0153752 A1 | 8/2003 | Hirst et al. |
| 2003/0187001 A1 | 10/2003 | Calderwood et al. |
| 2004/0157847 A1 | 8/2004 | Field et al. |
| 2005/0008640 A1 | 1/2005 | Waegell et al. |
| 2005/0026945 A1 | 2/2005 | Kafka et al. |
| 2005/0065176 A1 | 3/2005 | Field et al. |
| 2006/0025383 A1 | 2/2006 | Wishart et al. |
| 2006/0058297 A1 | 3/2006 | Roifman et al. |
| 2006/0058324 A1 | 3/2006 | Capraro et al. |
| 2007/0149464 A1 | 6/2007 | Billen et al. |
| 2007/0149550 A1 | 6/2007 | Billen et al. |
| 2007/0232668 A1 | 10/2007 | Priebe et al. |

(Continued)

FOREIGN PATENT DOCUMENTS

| | | |
|---|---|---|
| CN | 101880243 A | 11/2010 |
| EP | 0461546 A2 | 12/1991 |

(Continued)

OTHER PUBLICATIONS

Armesto et al., "Efficient photochemical synthesis of 2-vinylcyclopropanecarbaldehydes, precursors of cyclopropane components present in pyrethroids, by using the oxa-di-π-methane rearrangement," *Tetrahedron*, 66: 8690-8697 (2010).

(Continued)

*Primary Examiner* — Susanna Moore
(74) *Attorney, Agent, or Firm* — Finnegan, Henderson, Farabow, Garrett & Dunner, LLP

(57) ABSTRACT

The present disclosure provides compounds of Formula (I) and pharmaceutically acceptable salts that are tyrosine kinase inhibitors, in particular BLK, BMX, EGFR, HER2, HER4, ITK, Jak3, TEC, Btk, and TXK and are therefore useful for the treatment of diseases treatable by inhibition of tyrosine kinases such as cancer and inflammatory diseases such as arthritis, and the like. Also provided are pharmaceutical compositions containing such compounds and pharmaceutically acceptable salts and processes for preparing such compounds and pharmaceutically acceptable salts.

Formula (I)

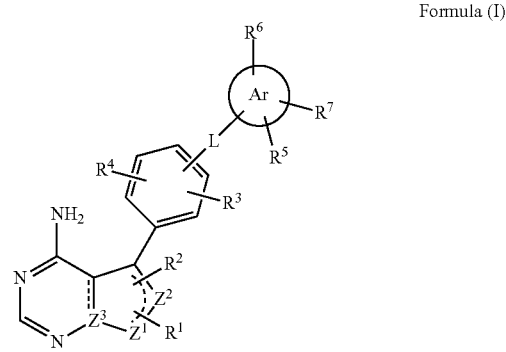

20 Claims, No Drawings

(56) References Cited

U.S. PATENT DOCUMENTS

| | | |
|---|---|---|
| 2007/0232688 A1 | 10/2007 | Orchansky et al. |
| 2008/0146643 A1 | 6/2008 | Billen et al. |
| 2008/0176865 A1 | 7/2008 | Billen et al. |
| 2009/0306396 A1 | 12/2009 | Toyoshima et al. |
| 2010/0113520 A1 | 5/2010 | Miller |
| 2010/0144705 A1 | 6/2010 | Miller |
| 2011/0021518 A1 | 1/2011 | Magnuson et al. |
| 2011/0086866 A1 | 4/2011 | Chen et al. |
| 2012/0028981 A1 | 2/2012 | Miller |
| 2014/0142099 A1 | 5/2014 | Owens |

FOREIGN PATENT DOCUMENTS

| | | |
|---|---|---|
| EP | 0493767 A2 | 7/1992 |
| EP | 0908457 A1 | 4/1999 |
| FR | 2535721 A1 | 5/1984 |
| GB | 2447933 A | 10/2008 |
| JP | 42008308 B4 | 4/1967 |
| JP | 56-63950 A | 5/1981 |
| JP | 200-1450 | 1/1990 |
| JP | 04-177244 A | 6/1992 |
| JP | 2005-239657 A | 9/2005 |
| WO | WO 95/24190 | 9/1995 |
| WO | WO 95/31432 A1 | 11/1995 |
| WO | WO 98/41499 A1 | 9/1998 |
| WO | WO 99/14216 | 3/1999 |
| WO | WO 01/72751 A1 | 10/2001 |
| WO | WO 03/050080 A1 | 6/2003 |
| WO | WO 03/082807 A2 | 10/2003 |
| WO | WO 2004/016259 A1 | 2/2004 |
| WO | WO 2004/074283 A1 | 9/2004 |
| WO | WO 2005/023773 A1 | 3/2005 |
| WO | WO 2005/030184 A1 | 4/2005 |
| WO | WO 2005/085210 A1 | 9/2005 |
| WO | WO 2006/134468 A1 | 12/2006 |
| WO | WO 2007/043401 A1 | 4/2007 |
| WO | WO 2007/087068 A2 | 8/2007 |
| WO | WO 2008/005954 A2 | 1/2008 |
| WO | WO 2008/039218 A2 | 4/2008 |
| WO | WO 2008/054827 A2 | 5/2008 |
| WO | WO 2008/061740 A1 | 5/2008 |
| WO | WO 2008/072053 A2 | 6/2008 |
| WO | WO 2008/072077 A2 | 6/2008 |
| WO | WO 2008/121742 A2 | 10/2008 |
| WO | WO 2010/009342 A2 | 1/2010 |
| WO | WO 2011/046964 A2 | 4/2011 |
| WO | WO 2011/060440 A2 | 5/2011 |
| WO | WO 2011/152351 A1 | 12/2011 |
| WO | WO 2011/153514 A2 | 12/2011 |
| WO | WO 2012/158810 A1 | 1/2012 |
| WO | WO 2012/158764 A1 | 11/2012 |
| WO | WO 2012/158843 A2 | 11/2012 |
| WO | WO 2013/003629 A2 | 1/2013 |
| WO | WO 2013/010136 A2 | 1/2013 |
| WO | WO 2013/010380 A1 | 1/2013 |
| WO | WO 2013/010868 A1 | 1/2013 |
| WO | WO 2013/010869 A1 | 1/2013 |
| WO | WO 2013/059738 A1 | 4/2013 |
| WO | WO 2013/102059 A1 | 7/2013 |
| WO | WO 2013/116382 A1 | 8/2013 |
| WO | WO 2013/191965 A1 | 12/2013 |
| WO | WO 2014/022569 A1 | 2/2014 |
| WO | WO 2014/039899 A1 | 3/2014 |
| WO | WO 2014/078578 A1 | 5/2014 |

OTHER PUBLICATIONS

Arnold, Lee D. et al., "Pyrrolo[2,3-d]pyrimidines Containing an Extended 5-Substituent as Potent and Selective Inhibitors of lck I," *Bioorganic & Medicinal Chemistry Letters*, 10:2167-2170 (2000).

Basheer, A., et al., "Enols of Substituted Cyanomalonamides," *J. Org. Chem*. 72:5297-5312 (2007).

Bernhart et al., "Synthesis and Antiarrhythmic activity of new [(Dialkylamino)alkyl]phridylacetamides," *J. Med. Chem.*, 26:451-455 (1983).

Burchat, A.F., et al., "Pyrrolo[2,3-d]pyrimidines Containing an Extended 5-Substituent as Potent and Selective Inhibitors of lck II," *Bioorganic & Medicinal Chemistry Letters*, 10:2171-2174 (2000).

Burini et al., "Efficient Synthesis of 4-Cyano 2,3-Dihydrooxazoles by Direct Amination of 2-Alkylidene 3-Oxo Nitriles," *SYNLETT*, 17: 2673-2675 (2005).

Calderwood, David J., et al., "Pyrrolo[2,3-d]pyrimidines Containing Diverse N-7 Substituents as Potent Inhibitors of Lck," *Bioorganic & Medicinal Chemistry Letters*, 12:1683-1686 (2002).

CAS RN 26272-41-3, Nov. 16, 1984.

Cohen, Michael S., et al., "Structural Bioinformatics-Based Design of Selective, Irreversible Kinase Inhibitors," *Science*, vol. 308. May 27, 2005.

Deng et al., "Reversible 4hosphor-Smad$_3$ signalling between tumour suppression and fibrocarcinogenesis in chronic hepatitis B infection," British Society for Immunology, *Clinical and Experimental Immunology*, 176: 102-111 (2013).

Donald, Alastair, et al., "Rapid Evolution of 6-Phenylpurine Inhibitors of Protein Kinase B through Structure-Based Design," *J. Med. Chem*., 50:2289-2292 (2007).

Elinson et al., "Electrochemical transformation of cyanoacetic ester and alkylidenecyanoacetic esters into 3-substituted 1,2-dicyanocyclopropane-1,2-dicarboxylates," *Russian Chemical Bulletin*, 47(6): 1133-1136 (1998).

Elliott et al., "The Pyrethrins and Related Compounds. Part XVIII. Insecticidal 2,2-Dimethylcyclopropanecarboxylates with New Unsaturated 3-Substituents," *Journal of the Chemical Society*, Perkin Transactions 1: Organic and Bio-Organic Chemistry (1972-1999) (1974), (21), 2470-4.

Elliott et al., "Insecticidal activity of the pyrethrins and related compounds X. $^a$ 5-benzyl-3-furylmethyl 2,2-dimethyicyclopropanecarboxylates with ethylenic substituents at position 3 on the cyclopropane ring," *Pestic. Sci.*, 7: 499-502 (1976).

Fioravanti et al., "Parallel Solution-Phase Synthesis of Acrylonitrile Scaffolds Carrying $_L$- α-Amino Acidic or D-Glycosyl Residues," *J. Comb. Chem*., 8: 808-811 (2006).

Gyoung et al, "Regiospecific synthesis of 2-allylated-5-substituted tetrazoles via palladium-catalyzed reaction of nitriles, trimethylsilyl azide, and allyl acetates," *Tetrahedron Letters*, 41(21): 4193-4196 (2000).

International Preliminary Report on Patentability for International Application No. PCT/US2010/056890, mailed May 22, 2012.

International Search Report, PCT/US2010/056890, mailed Jul. 28, 2011.

Jenner, "Steric effects in high pressure Knoevenagel reactions," *Tetrahedron Letters*, 42(2): 243-245 (2001).

Kamath, S. and Buolamwini John K., "Receptor-Guided Alignment-Based Comparative 3D-QSAR Studies of Benzylidene Malonitrile Tyrphostins as EGFR and HER-2 Kinase Inhibitors," *J. Med. Chem*., 46:4657-4668 (2003).

Kamijo et al., "Tetrazole synthesis via the palladium-catalyzed three component coupling reaction," *Molecular Diversity*, 6: 181-192 (2003).

Knight, Z.A., "A membrane capture assay for lipid kinase activity," *Nature Protocols*, vol. 2, No. 10 (2007).

Kojima et al., "Stereoselective synthesis of activated cyclopropanes with an α-pyridinium acetamide bearing an 8-phenylmenthyl group as the chiral auxiliary," *Tetrahedron Letters*, 45(18): 3565-3568 (2004).

Komura et al., "Layered silicate PLS-1: A new solid base catalyst for C—C bond forming reactions," *Catalysis Communications*, 8(4): 644-648 (2007).

Kotz et al., "The Action of Chloroform on Methylene and Methenyl Groups," *Journal fuer Praktische Chemie (Leipzig)*, Abstract, 74: 425-48 (1907).

Lou et al., "Bruton's Tyrosine Kinase Inhibitors: Approaches to Potent and Selective Inhibition, Preclinical and Clinical Evaluation for Inflammatory Diseases and B Cell Malignancies," *J. Med. Chem*., 55(10): 4539-4550 (2012).

Maas et al., "Conjugate Addition of Dialkylaluminum Chlorides to Alkylidenemalonic Acid Derivatives," *Synthesis*, 10: 1792-1798 (1999).

(56) References Cited

OTHER PUBLICATIONS

Maurya et al., "Catalyst-free stereoselective cyclopropanation of electron deficient alkenes with ethyl diazoacetate," *RSC Advances*, 3: 15600-15603 (2013).
Miller, Rand M., "Electrophilic Fragment-Based Design of Reversible Covalent Kinase Inhibitors," *J. Am. Chem. Soc.* 135(14):5298-5301 (2013).
Neplyuev, "Studies of triacylmethanes VII. 1,1,3,3-Tetraacyl-3-arylazo-1-propenes," *Zhurnal Organicheskoi Khimii*, Abstract, 15(3): 563-6 (1979).
Neplyuev, "Nitration and nitrosation of 1,1,3,3-tetraacyl-1-propenes"*Ukrainskii Khimicheskii Zhurnal (Russian Edition)*, Abstract, 49(2): 192-4 (1983).
Pan, Zhengying, et al., "Discovery of Selective Irreversible Inhibitors for Bruton's Tyrosine Kinase," *ChemMedChem*, 2:58-61 (2007).
Porter et al., "The discovery of potent, orally bioavailable pyrimidine-5-carbonitrile-6-alkyl CXCR2 receptor antagonists," *Bioorganic & Medicinal Chemistry Letters*, 24: 3285-3290 (2014).
Proenca, Fernanda and Costa, Marta, "A simple and eco-friendly approach for the synthesis of 2-imino and 2-oxo-2H-chromene-3-carboxamides,"*Green Chem.*, 10:995-998 (2008).
Rellos, Peter et al., "Structure and Regulation of the Human Nek2 Centrosomal Kinase," *Journal of Biological Chemistry*, 282(9):6833-6842 (2007).
Sammes, M.P., et al., "α-Cyano-sulphonyl Chlorides : Their Preparation and Reactions with Amines, Alcohols, and Enamines," *J. Chem. Soc.* / 2151-2155 (1971).
Santilli Arthur A. and Osdene T.S., "8,9,10,11-Tetrahydro-12$H$-benzo[5,6]quinoxalino[2,3-$e$][1,4]diazepin-12-ones. Examples of a New Heterocyclic Ring System," *J. Org. Chem.*, 29:2066-2068 (1964).
Schwarz et al., "Novel Cyclopropyl β-Amino Acid Analogues of Pregabalin and Gabapentin That Target the $\alpha_2$-δ Protein," *J. Med. Chem.*, 48:3026-3035 (2005).
SciFinder® dated May 9, 2011, 8:13 pm.
SciFinder® dated May 9, 2011, 8:23 pm.
SciFinder® dated May 9, 2011, 8:33 pm.
SciFinder® dated May 9, 2011, 9:06 pm.
SciFinder® dated May 10, 2011, 10:04 am.
SciFinder® dated May 10, 2011, 10:20 am.
SciFinder® dated May 10, 2011, 10:46 am.
Serafimova, Iana M., et al., "Reversible targeting of noncatalytic cysteines with chemically tuned electrophiles," *Nature Chemical Biology*, 8, 471-476 (2012).
Stevens et al, "Synthesis of Substituted Cyclopropylphosphonates by Michael Induced Ring Closure (MIRC) Reactions," *Synlett*, 7: 1089-1092 (2002).
Verhé et al., "Preparation of 2,2-Dialkylcyclopropanes Geminally Substituted with Electron-Withdrawing Groups," Synthesis, 7: 530-2 (1978).
Verhé et al., "Thermal Lactonization of Brominated Alkylidenemalonates: Synthesis of 2-Buten-4-Olides," *Bulletin des Societes Chimiques Belges*, 87(3): 215-222 (1978).
Verhé et al, "Synthesis of 1,1-Bis(Hydroxymethyl) Cyclopropanes," *Organic Preparations and Procedures International*, 13(1): 13-18 (1981).
Vo et al., "Transformations of Resin-Bound Pyridinium Ylides: I. A Stereoselective Synthesis of 2,2,3-Trisubstituted Cyclopropanecarboxylates," *Tetrahedron Letters*, 38(46): 7951-7954 (1997).
Wang, "Cyanoacetamide Multicomponent Reaction (I): Parallel Synthesis of Cyanoacetamides," *J. Comb. Chem.* 11:920-927 (2009).
Wang, Gary T., et al., "Substituted 4-amino-1H-pyrazolo[3,4-d]pyrimidines as multi-targeted inhibitors of insulin-like growth factor-I receptor (IGFIR) and members of ErbB-family receptor kinases," *Bioorganic & Medicinal Chemistry Letters*, 20:6067-6071 (2010).
Wells, Geoffrey et al., "Structural Studies on Bioactive Compounds. 32.[1] Oxidation of Tyrphostin Protein Tyrosine Kinase Inhibitors with Hypervalent Iodine Reagents," *J. Med. Chem.* 43:1550-1562 (2000).
Zhang et al., "Organic base catalyzed carbonyl allylation of methyl trifluoropyruvate with activated alkenes," *Tetrahedron*, 65: 83-86 (2009).
Zimmerman et al., "The Diverted Di-π-Methane Rearrangement; Mechanistic and Exploratory Organic Photochemistry," *Organic Letters*, 4(7): 1155-1158 (2002).
International Search Report and Written Opinion mailed Jul. 5, 2012 for PCT Application No. PCT/US2012/038092.
International Search Report mailed Feb. 1, 2013 for PCT Application No. PCT/US2012/038214.
PCT Notification of Transmittal of the International Search Report and the Written Opinion of the International Searching Authority, or the Declaration for International Application No. PCT/US2013/058614, mailed Nov. 5, 2013.
International Search Report mailed Jul. 25, 2012 for PCT Application No. PCT/US2012/038135.
File History of U.S. Appl. No. 13/859,569, "Tyrosine Kinase Inhibitors" in the name of David Michael Goldstein, filed Apr. 9, 2013.
File History of U.S. Appl. No. 13/929,004, "Tyrosine Kinase Inhibitors" in the name of David Michael Goldstein, filed Jun. 27, 2013.
File History of U.S. Appl. No. 13/929,179, "Tyrosine Kinase Inhibitors" in the name of David Michael Goldstein, filed Jun. 27, 2013.
File History of U.S. Appl. No. 14/185,687, "Tyrosine Kinase Inhibitors" in the name of David Michael Goldstein, filed Feb. 20, 2014.
File History of U.S. Appl. No. 14/255,842, "Tyrosine Kinase Inhibitors" in the name of David Michael Goldstein, filed Apr. 17, 2014.
File History of U.S. Appl. No. 14/341,421, "Tyrosine Kinase Inhibitors" in the name of David Michael Goldstein, filed Jul. 25, 2014.
File History of U.S. Appl. No. 14/117,933, "Tyrosine Kinase Inhibitors" in the name of David Michael Goldstein, filed Nov. 15, 2013.
File History of U.S. Appl. No. 14/374,788, "Pyrazolopyrimidine Compounds as Kinase Inhibitors," in the name of Tim Owens, filed Jul. 25, 2014.
File History of U.S. Appl. No. 14/464,602, "Pyrazolopyrimidine Compounds as Kinase Inhibitors," in the name of Tim Owens, filed Aug. 20, 2014.
File History of U.S. Appl. No. 14/084,519, "Purinone Derivatives as Tyrosine Kinase Inhibitors," in the name of Timothy D. Owens, filed Nov. 19, 2013.

PYRAZOLOPYRIMIDINE DERIVATIVES AS TYROSINE KINASE INHIBITORS

The application is a national stage entry under 35 U.S.C. §371 of International Application No. PCT/US2012/038135, filed May 16, 2012 which claims priority to U.S. Provisional Application No. 61/486,933, filed May 17, 2011 all of which are incorporated herein by reference.

The present disclosure provides compounds and pharmaceutically acceptable salts that are tyrosine kinase inhibitors, in particular BLK, BMX, EGFR, HER2, HER4, ITK, Jak3, TEC, Btk, and TXK and are therefore useful for the treatment of diseases treatable by inhibition of tyrosine kinases such as cancer and inflammatory diseases such as arthritis, and the like. Also provided are pharmaceutical compositions containing such compounds and pharmaceutically acceptable salts and processes for preparing such compounds and pharmaceutically acceptable salts.

The human genome contains at least 500 genes encoding protein kinases. Many of these kinases have been implicated in human disease and as such represent potentially attractive therapeutic targets. For example EGFR is overexpressed in breast, head and neck cancers and the overexpression is correlated with poor survival (see Do N. Y., et al., Expression of c-erbB receptors, MMPs and VEGF in squamous cell carcinoma of the head and neck. *Oncol Rep.* August 12:229-37. 2004 and Foley J, et al., EGFR signaling in breast cancer: bad to the bone. *Semin Cell Dev Biol.* 21:951-60. 2010). Her2, another EGFR family member, also is amplified or overexpressed in up to 30% of breast cancers, also correlating with poor survival (see Murphy C. G, Modi S. HER2 breast cancer therapies: a review. *Biologics* 3:289-301. 2009). HER4, also in the EGFR family, is overexpressed in head and neck squamous cell carcinomas (4). Other studies show decreased expression of HER4 in certain cancers and suggest tumor suppressor activity (see Thomasson M, et al., ErbB4 is down-regulated in renal cell carcinoma—a quantitative RT-PCR and immunohistochemical analysis of the epidermal growth factor receptor family. *Acta Oncol.* 43:453-9. 2004). Overall the data support a role for members of the EGFR family in cancer. ITK, a member of the TEC kinase family, is involved in activation of T cells and mast cells (see Iyer A. S. et al. Absence of Tec Family Kinases Interleukin-2 Inducible T cell Kinase (Itk) and Bruton's Tyrosine Kinase (Btk) Severely Impairs Fc{epsilon}RI-dependent Mast Cell Responses. *J. Biol Chem.*;286:9503-13. 2011) and is a potential target in inflammatory immune diseases such as asthma. Mice deficient in ITK are resistant to development of allergic asthma (see Sahu N, et al., Differential sensitivity to Itk kinase signals for T helper 2 cytokine production and chemokine-mediated migration. *J. Immunol.* 180:3833-8. 2008). Another family member, BMX, is involved in supporting tumor angiogenesis through it's role in the tumor vascular endothelium (see Tu T, et al., Bone marrow X kinase-mediated signal transduction in irradiated vascular endothelium. *Cancer Res.* 68:2861-9. 2008) and is also progressively up-regulated during bladder cancer progression (see Guo S, et al., Tyrosine Kinase ETK/BMX Is Up-Regulated in Bladder Cancer and Predicts Poor Prognosis in Patients with Cystectomy. *PLoS One.* 6:e17778. 2011) suggesting a potential therapeutic target in this type cancer. Jak3, which is critical for signaling downstream of IL-2 as well as other cytokines that utilize the common gamma chain of the IL-2 receptor, has clinical utility for a number of indications including rheumatoid arthritis, kidney transplantation, Crohn's disease, psoriasis, and Jak3-dependent hematopoietic malignancies (see Ghoreschi K, et al., Janus kinases in immune cell signaling. *Immunol Rev.* 228: 273-87. 2009). The B lymphoid kinase (BLK) is linked through genetic association with a variety of rheumatic diseases including systemic lupus erythematosus and systemic sclerosis (see Ito I, et al., Association of the FAMI67A-BLK region with systemic sclerosis. *Arthritis Rheum.* 62:890-5. 2010).

Bruton's tyrosine kinase (abbreviated as Btk), a member of the Tec family non-receptor tyrosine kinases that is essential for B cell signaling downstream from the B-cell receptor. It is expressed in B cells and other hematopoietic cells such as monocytes, macrophages and mast cells. It functions in various aspects of B cell function that maintain the B cell repertoire (see Gauld S. B. et al., B cell antigen receptor signaling: roles in cell development and disease. Science, 296:1641-2. 2002.)). Clinical validation of the role of B cells in RA has been provided by the efficacy of Rituxan (an anti-CD20 antibody), which depletes B cells as a mechanism of action (see Perosa F., et al., CD20-depleting therapy in autoimmune diseases: from basic research to the clinic. *J Intern Med.* 267: 260-77. 2010 and Dörner T, et al. Targeting B cells in immune-mediated inflammatory disease: a comprehensive review of mechanisms of action and identification of biomarkers. *Pharmacol Ther.* 125:464-75. 2010.). Btk is known to be required for B cell development because patients with the disease X-linked agammaglobulinemia (see Rosen F. S., et al., The primary immunodeficiencies. *N Engl J Med.* 333: 431-40. 1995). Notably, small-molecule Btk inhibitors in preclinical development have been shown to be efficacious in collagen-induced arthritis (see Pan Z., et al., Discovery of selective irreversible inhibitors for Bruton's tyrosine kinase. *J. Med. Chem.* 2:58-61. 2007). However, the potential advantage of a Btk inhibitor (beyond the inherent advantage of a small-molecule over a biologic) is that modulation of Btk can inhibit B cell function without permanent removal of the B cell itself. Therefore, the long periods of low B cell levels experienced with Rituxan should be avoidable by targeting Btk.

In addition, the disease modifying activities of Btk are expected to extend beyond those of Rituxan because of effects on addition cellular targets that are involved in propagation of disease. For instance, antigen induced mast cell degranulation is impaired in mast cells derived from the bone marrow of Btk deficient mice, demonstrating that Btk is downstream of the FcεR1 receptor (see Setoguchi R., et al., Defective degranulation and calcium mobilization of bone-marrow derived mast cells from Xid and Btk-deficient mice. *Immunol Lett.* 64:109-18. 1998). A similar signaling module exists in monocytes and macrophages for the FcγR1 receptor indicating Btk inhibition is highly likely to modulate TNF production in response to IgG. Both mast cells and macrophages are thought to contribute to propagation of the inflammatory cytokine environment of the diseased synovium.

In addition to the peripheral and synovial effects of Btk inhibition described above, there is evidence that Btk inhibition will have bone protective effects in the inflamed joint (see Gravallese E. M., et al., Synovial tissue in rheumatoid arthritis is a source of osteoclast differentiation factor. *Arthritis Rheum.* 43:250-8. 2000). Studies with mice that are either deficient in Btk or have impaired Btk function have demonstrated that Rank ligand-induced osteoclast differentiation is impaired in the absence of Btk function (see Lee S. H., et. al., The tec family tyrosine kinase Btk Regulates RANKL-induced osteoclast maturation. *J. Biol. Chem.* 283:11526-34. 2008). Taken together these studies suggest a Btk inhibitor could inhibit or reverse the bone destruction that occurs in RA patients. Given the importance of B cells in autoimmune disease, Btk inhibitors could also have utility in other autoimmune diseases such as systemic lupus erythematosus (see Shlomchik M. J., et. al., The role of B cells in lpr/lpr-induced autoimmunity. *J. Exp Med.* 180:1295-1306. 1994). Notably, an irreversible Btk inhibitor has been shown to display efficacy in the mouse MRL/lpr lupus model, reducing autoantibody production and renal damage (see Honigberg L. A., The Bruton tyrosine kinase inhibitor PCI-32765 blocks B-cell activation and is efficacious in models of autoimmune disease and B-cell malignancy. *Proc. Natl. Acad. Sci.* 107:13075-80. 2010).

There is also potential for Btk inhibitors for treating allergic diseases (see Honigberg, L., et. al., The selective Btk inhibitor PCI-32765 blocks B cell and mast cell activation and prevents mouse collagen induced arthritis. *Clin. Immunol.* 127 S1:S111. 2008). In addition, the irreversible inhibitor suppresses passive cutaneous anaphylaxis (PCA) induced by IgE antigen complex in mice (see Honigberg, L, et. al., The selective Btk inhibitor PCI-32765 blocks B cell and mast cell activation and prevents mouse collagen induced arthritis. *Clin. Immunol.* 127 S1:S111. 2008). These findings are in agreement with those noted with Btk-mutant mast cells and knockout mice and suggest that Btk inhibitors may be useful for the treatment of asthma, an IgE-dependent allergic disease of the airway.

In addition, platelet aggregation in response to collagen or collagen-related peptide is impaired in XLA patients who lack Btk function (see Quek L. S, et al., A role for Bruton's tyrosine kinase (Btk) in platelet activation by collagen. *Curr. Biol.* 8:1137-40.1998). This is manifested by changes downstream from GPIV, such as phosphorylation of PLCgamma2 and calcium flux, which suggests potential utility in treating thromboembolic diseases.

Preclinical studies with a selective inhibitor of Btk have shown effects on spontaneous canine B cell lymphomas suggesting a potential utility in human lymphomas or other hematologic malignancies including chronic lymphocytic leukemia.

Accordingly, there is a need for compounds that inhibit tyrosine kinases thereby providing treatment for diseases such as autoimmune diseases, thromboembolic diseases and cancer. The present disclosure fulfills this need and related needs.

In one aspect, this disclosure is directed to a compound of Formula (I) or a pharmaceutically acceptable salt thereof:

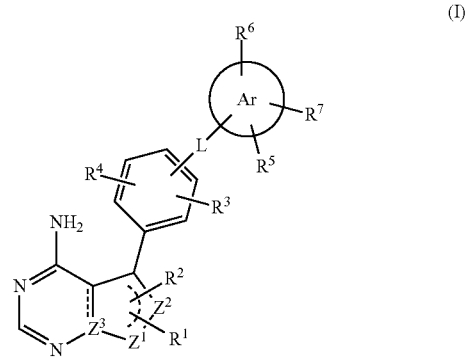

wherein:

dashed lines are independently an optional bond;

$Z^1$, $Z^2$, and $Z^3$ are —N— or CH, provide that at least one and not more than two of $Z^1$, $Z^2$, and $Z^3$ are simultaneously N;

L is O, CO, $CH_2$, S, SO, $SO_2$, NR, NRCO, CONR, NR'$SO_2$, $SO_2$NR', or NRCONR', where (each R and R' is independently hydrogen, alkyl, or cycloalkyl);

Ar is aryl, heteroaryl, cycloalkyl or heterocyclyl;

one of $R^1$ and $R^5$ is hydrogen, alkyl, hydroxy, alkoxy, halo, haloalkyl, or haloalkoxy and the other of $R^1$ and $R^5$ is:

(i) —P-Q-CH=C($R^b$)(EWG) where P is a bond, $NR^a$ (where $R^a$ is hydrogen or alkyl), —O—, S, SO, $SO_2$, alkylene or heteroalkylene, Q is a bond, aryl or heteroaryl wherein aryl or heteroaryl is optionally substituted with one or two substituents independently selected from hydrogen, halo, alkyl, alkoxy, alkylthio, haloalkyl, or haloalkoxy, $R^b$ is cyano, nitro, halo, haloalkyl, haloalkoxy, alkylthio, or alkylsulfonyl and EWG is an electron withdrawing group; or (ii) —Z-(EWG')-C($R^{b'}$)=$CHR^c$ where Z is bond, $NR^a$ (where $R^a$ is hydrogen or alkyl), —O—, S, SO, $SO_2$, alkylene, cycloalkylene, heteroalkylene, —$(Z^a)_{n1}$-aryl, or —$(Z^a)_{n1}$-heteroaryl (wherein n1 is 0 or 1, $Z^a$ is $NR^a$ (where $R^a$ is hydrogen or alkyl), —O—, S, SO, $SO_2$, alkylene, or heteroalkylene and aryl or heteroaryl is optionally substituted with one or two substituents independently selected from hydrogen, halo, alkyl, alkoxy, alkylthio, haloalkyl, or haloalkoxy), EWG' is a bond or an electron withdrawing group, $R^{b'}$ is nitro, halo, haloalkyl, haloalkoxy, alkylthio, or alkylsulfonyl and $R^c$ is alkyl, substituted alkyl, haloalkoxy, cycloalkyl, cycloalkylene$NR^dR^e$ where $R^d$ and $R^e$ are independently hydrogen, alkyl, or cycloalkyl; or (iii) a group of formula (a) or (b);

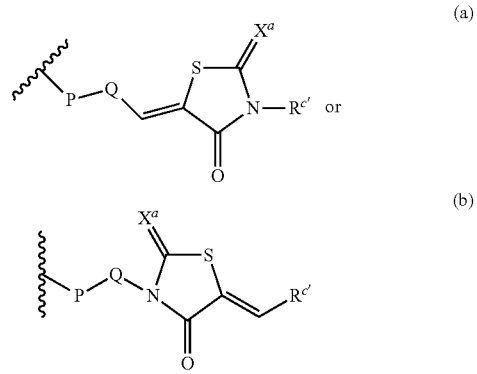

where P and Q are as defined above, $X^a$ is O, S, or N(H or alkyl) and $R^{c'}$ is hydrogen, alkyl, substituted alkyl, haloalkoxy, cycloalkyl, or cycloalkylene$NR^dR^e$ where $R^d$ and $R^e$ are independently hydrogen, alkyl, or cycloalkyl;

$R^2$ is hydrogen, alkyl, hydroxy, alkoxy, cyano, halo or haloalkyl;

$R^3$ and $R^4$ are independently hydrogen, alkyl, cycloalkyl, hydroxy, alkoxy, cyano, halo, haloalkyl or haloalkoxy; and $R^6$ and $R^7$ are independently hydrogen, alkyl, hydroxy, alkoxy, halo, haloalkyl, haloalkoxy, carboxy, alkoxycarbonyl, cyano, —$CONH_2$, amino, monosubstituted and disubstituted amino;

provided that the compound of Formula (I) is not:

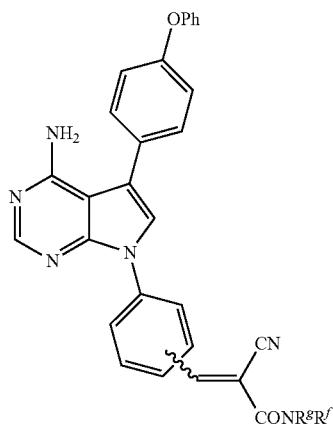

where $R^g$ is hydrogen or alkyl and $R^f$ is hydrogen, alkyl, hydroxyalkyl, or $R^g$ and $R^h$ together with the nitrogen atom to which they are attached form piperazinyl or azetidinyl each ring optionally substituted with alkyl or hydroxyl.

In a second aspect, this disclosure is directed to a pharmaceutical composition comprising a compound of Formula (I) (or any of the embodiments thereof described herein), or a pharmaceutically acceptable salt thereof; and a pharmaceutically acceptable excipient.

In a third aspect, this disclosure is directed to a method of treating a disease treatable by inhibition of tyrosine kinase such as BLK, BMX, EGFR, HER2, HER4, ITK, Jak3, TEC, Btk, and TXK, preferably Btk, in a patient which method comprises administering to the patient in need thereof, a pharmaceutical composition comprising a compound of Formula (I) or (or any of the embodiments thereof described herein) or a pharmaceutically acceptable salt thereof, and a pharmaceutically acceptable salt thereof and a pharmaceutically acceptable excipient. In one embodiment the disease is inflammatory disease such as arthritis, kidney disease, or cancer such as B-cell non-Hodgkin lymphoma.

In one embodiment of this aspect, the patient in need is suffering from an autoimmune disease, e.g., inflammatory bowel disease, arthritis, lupus, rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, Sjogren's syndrome, multiple sclerosis, Guillain-Barre syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, endometriosis, interstitial cystitis, neuromyotonia, sceroderma, or vulvodynia. Preferably, the disease is rheumatoid arthritis. Preferably, the autoimmune disease is lupus.

In another embodiment of this aspect, the patient in need is suffering from a heteroimmune condition or disease, e.g., graft versus host disease, transplantation, transfusion, anaphylaxis, allergy, type I hypersensitivity, allergic conjunctivitis, allergic rhinitis, or atopic dermatitis.

In another embodiment of this aspect, the patient in need is suffering from an inflammatory disease, e.g., asthma, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, or vulvitis.

In another embodiment of this aspect, the patient is suffering from inflammatory skin disease which includes, by way of example, dermatitis, contact dermatitis, eczema, urticaria, rosacea, and scarring psoriatic lesions in the skin, joints, or other tissues or organs.

In yet another embodiment of this aspect, the patient in need is suffering from a cancer. In one embodiment, the cancer is a B-cell proliferative disorder, e.g., diffuse large B cell lymphoma, follicular lymphoma, chronic lymphocytic lymphoma, chronic lymphocytic leukemia, B-cell prolymphocytic leukemia, lymphoplamascytic lymphoma/Waldenstrom macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, burkitt lymphoma/leukemia, or lymphomatoid granulomatosis. In some embodiments, the compound of Formula (I) is administered in combination with another an anti-cancer agent e.g., the anti-cancer agent is an inhibitor of mitogen-activated protein kinase signaling, e.g., U0126, PD98059, PD184352, PD0325901, ARRY-142886, SB239063, SP600125, BAY 43-9006, wortmannin, LY294002, Nexavar®, Tarceva®, Sutent®, Tykerb®, Sprycel®, Crizotinib, and Xalkori®.

In yet another embodiment, the patient in need is suffering from a thromboembolic disorder, e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, or deep venous thrombosis.

In a fourth aspect, the disclosure is directed to a compound of Formula (I) (and any embodiments thereof described herein) for use as a medicament. In one embodiment, the use of compound of Formula (I) is for treating inflammatory disease or proliferative diseases.

In a fifth aspect, is the use of a compound of Formula (I) in the manufacture of a medicament for treating an inflammatory disease in a patient in which the activity of a tyrosine kinase such as BLK, BMX, EGFR, HER2, HER4, ITK, Jak3, TEC, Btk, or TXK, preferably, Btk contributes to the pathology and/or symptoms of the disease. In one embodiment of this aspect, the tyrosine kinase protein is Btk. In another embodiment of this aspect, the inflammatory disease is respiratory, cardiovascular, or proliferative diseases.

In any of the aforementioned aspects involving the treatment of proliferative disorders, including cancer, are further embodiments comprising administering the compound of Formula (I) in combination with at least one additional agent selected from the group consisting of alemtuzumab, arsenic trioxide, asparaginase (pegylated or non-), bevacizumab, cetuximab, platinum-based compounds such as cisplatin, cladribine, daunorubicin/doxorubicin/idarubicin, irinotecan, fludarabine, 5-fluorouracil, gemtuzamab, methotrexate, paclitaxel, Taxol™, temozolomide, thioguanine, or classes of drugs including hormones (an antiestrogen, an antiandrogen, or gonadotropin releasing hormone analogues, interferons such as alpha interferon, nitrogen mustards such as busulfan or melphalan or mechlorethamine, retinoids such as tretinoin, topoisomerase inhibitors such as irinotecan or topotecan, tyrosine kinase inhibitors such as gefinitinib or imatinib, or agents to treat signs or symptoms induced by such therapy including allopurinol, filgrastim, granisetron/ondansetron/palonosetron, dronabinol. When combination therapy is used, the agents can be administered simultaneously or sequentially.

DEFINITIONS

Unless otherwise stated, the following terms used in the specification and claims are defined for the purposes of this application and have the following meaning:

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, butyl (including all isomeric forms), pentyl (including all isomeric forms), and the like.

"Alkylene" means a linear saturated divalent hydrocarbon radical of one to six carbon atoms or a branched saturated divalent hydrocarbon radical of three to six carbon atoms unless otherwise stated e.g., methylene, ethylene, propylene, 1-methylpropylene, 2-methylpropylene, butylene, pentylene, and the like.

"Alkylthio" means a —SR radical where R is alkyl as defined above, e.g., methylthio, ethylthio, and the like.

"Alkylsulfonyl" means a —SO$_2$R radical where R is alkyl as defined above, e.g., methylsulfonyl, ethylsulfonyl, and the like.

"Amino" means a —NH$_2$.

"Alkylamino" means a —NHR radical where R is alkyl as defined above, e.g., methylamino, ethylamino, propylamino, or 2-propylamino, and the like.

"Alkoxy" means a —OR radical where R is alkyl as defined above, e.g., methoxy, ethoxy, propoxy, or 2-propoxy, n-, iso-, or tert-butoxy, and the like.

"Alkoxyalkyl" means a linear monovalent hydrocarbon radical of one to six carbon atoms or a branched monovalent hydrocarbon radical of three to six carbons substituted with at least one alkoxy group, preferably one or two alkoxy groups, as defined above, e.g., 2-methoxyethyl, 1-, 2-, or 3-methoxypropyl, 2-ethoxyethyl, and the like.

"Alkoxycarbonyl" means a —C(O)OR radical where R is alkyl as defined above, e.g., methoxycarbonyl, ethoxycarbonyl, and the like.

"Aminocarbonyl" means a —CONRR' radical where R is independently hydrogen, alkyl, or substituted alkyl, each as defined herein and R' is hydrogen, alkyl, cycloalkyl, cycloalkylalkyl, aryl, aralkyl, heteroaryl, heteroaralkyl, heterocyclyl, heterocyclylalkyl, or substituted alkyl, each as defined herein and wherein the aryl, heteroaryl, or heterocyclyl ring either alone or part of another group e.g., aralkyl, is optionally substituted with one, two, or three substituents independently selected from alkyl, alkoxy, halo, haloalkoxy, hydroxyl, carboxy, or alkoxycarbonyl, e.g., —CONH$_2$, methylaminocarbonyl, 2-dimethylaminocarbonyl, and the like.

"Aminosulfonyl" means a —SO$_2$NRR' radical where R is independently hydrogen, alkyl, or substituted alkyl, each as defined herein and R' is hydrogen, alkyl, cycloalkyl, cycloalkylalkyl, aryl, aralkyl, heteroaryl, heteroaralkyl, heterocyclyl, heterocyclylalkyl, or substituted alkyl, each as defined herein and wherein the aryl, heteroaryl, or heterocyclyl ring either alone or part of another group e.g., aralkyl, is optionally substituted with one, two, or three substituents independently selected from alkyl, alkoxy, halo, haloalkoxy, hydroxyl, carboxy, or alkoxycarbonyl, e.g., —SO$_2$NH$_2$, methylaminosulfonyl, dimethylaminosulfonyl, and the like.

"Acyl" means a —COR radical where R is alkyl, haloalkyl, cycloalkyl, cycloalkylalkyl, aryl, aralkyl, heteroaryl, heteroaralkyl, heterocyclyl, or heterocyclylalkyl, each as defined herein and wherein the aryl, heteroaryl, or heterocyclyl ring either alone or part of another group e.g., aralkyl, is optionally substituted with one, two, or three substituents independently selected from alkyl, alkoxy, halo, haloalkoxy, hydroxyl, carboxy, or alkoxycarbonyl, e.g., acetyl, propionyl, benzoyl, pyridinylcarbonyl, and the like. When R is alkyl, the radical is also referred to herein as alkylcarbonyl.

"Aryl" means a monovalent monocyclic or bicyclic aromatic hydrocarbon radical of 6 to 10 ring atoms e.g., phenyl or naphthyl.

"Aralkyl" means a -(alkylene)-R radical where R is aryl as defined above.

"Cycloalkyl" means a cyclic saturated monovalent hydrocarbon radical of three to ten carbon atoms wherein one or two carbon atoms may be replaced by an oxo group, e.g., cyclopropyl, cyclobutyl, cyclopentyl, or cyclohexyl, and the like.

"Cycloalkylalkyl" means a -(alkylene)-R radical where R is cycloalkyl as defined above; e.g., cyclopropylmethyl, cyclobutylmethyl, cyclopentylethyl, or cyclohexylmethyl, and the like.

"Cycloalkylene" means a divalent cyclic saturated hydrocarbon radical of three to ten carbon atoms wherein one or two carbon atoms may be replaced by an oxo group, e.g., cyclopropylene, cyclobutylene, cyclopentylene, or cyclohexylene, and the like.

"Carboxy" means —COOH.

"Disubstituted amino" means a —NRR' radical where R and R' are independently alkyl, cycloalkyl, cycloalkylalkyl, acyl, sulfonyl, aryl, aralkyl, heteroaryl, heteroaralkyl, heterocyclyl, heterocyclylalkyl, or substituted alkyl, each as defined herein and wherein the aryl, heteroaryl, or heterocyclyl ring either alone or part of another group e.g., aralkyl, is optionally substituted with one, two, or three substituents independently selected from alkyl, alkoxy, halo, haloalkoxy, hydroxyl, carboxy, or alkoxycarbonyl, e.g., dimethylamino, phenylmethylamino, and the like. When the R and R' groups are alkyl, the disubstituted amino group maybe referred to herein as dialkylamino.

The term "electron withdrawing group" refers to a chemical substituent that modifies the electrostatic forces acting on a nearby chemical reaction center by withdrawing negative charge from that chemical reaction center. Thus, electron withdrawing groups draw electrons away from a reaction center. As a result, the reaction center is fractionally more positive than it would be in the absence of the electron-withdrawing group. In some embodiments, the chemical reaction center is one of the two carbons forming the carbon-carbon double bond (olefin). In some embodiments, the chemical reaction center is the olefin carbon attached to EWG. The electron withdrawing group functions to draw charge or electrons away from this olefin carbon thereby making the olefin carbon electron deficient (relative to the absence of the electron withdrawing group). The electron deficient olefin carbon is thereby rendered more reactive toward electron rich chemical groups, such as the sulfhydryl of a kinase active site cysteine.

Some non-limiting examples of EWG include, but are not limited to, —N(R'$_2$), —N(R'$_3$)$^+$, —SO$_3$H, —SO$_3$R', —S(O$_2$)R', —S(O)R', —C(O)NH$_2$, —C(O)NHR$^g$, —C(O)NR$^f$R$^g$, —S(O$_2$)NH$_2$, —SO$_2$NHR$^i$, —SO$_2$NR$^h$R$^i$, —PO(OR')$_2$, —PO$_3$H$_2$, —PO(NR'$_2$)$_2$, —C≡N, —CH(haloalkyl), —C(O)X', —COOH, —COOR', —C(O)R', —C(O)H, —P(O)(OR')OR", halo, heteroaryl, or aryl; wherein X' is independently halogen (e.g. chloro or fluoro), R', R", R$^f$, R$^g$, R$^h$, and R$^i$ are independently hydrogen, alkyl, substituted alkyl, cycloalkyl, cycloalkyleneNR$^d$R$^e$ (where R$^d$ and R$^e$ are independently hydrogen, alkyl, or cycloalkyl) or R$^f$ and R$^g$ and R$^h$ and R$^i$ together with the nitrogen atom to which they are attached form heterocycloamino; and aryl and heteroaryl are substituted with one, two or three substituents independently selected from hydrogen, alkyl, alkoxy, hydroxyl, cyano, nitro, halo, haloalkyl, haloalkoxy, alkylthio, alkylsulfonyl, carboxy, alkoxycarbonyl, aminocarbonyl or aminosulfonyl.

Preferably, EWG is —CO—NR$^f$R$^g$, —SO$_2$NR$^h$R$^i$ (wherein R$^f$ and R$^h$ are independently hydrogen, alkyl, or cycloalkyl and R$^g$ and R$^i$ are independently hydrogen, alkyl, substituted alkyl, or cycloalkyleneNR$^d$R$^e$ (where R$^d$ and R$^e$ are independently hydrogen, alkyl, or cycloalkyl); or R$^f$ and R$^g$ and R$^h$ and R$^i$ together with the nitrogen atom to which they are attached form heterocycloamino), aryl or heteroaryl wherein each of the aforementioned ring is substituted with one, two or three substituents independently selected from hydrogen, alkyl, alkoxy, hydroxyl, cyano, nitro, halo, haloalkyl, haloalkoxy, alkylthio, alkylsulfonyl, carboxy, alkoxycarbonyl, aminocarbonyl or aminosulfonyl. Preferably, the heteroaryl ring is pyridinyl, pyrazolyl, indazolyl, indolyl, thienyl, pyrrolyl, imidazolyl, thiazolyl, benzothiazolyl, oxazolyl, benzimidazolyl, benzoxazolyl, isoxazolyl, benzisoxazolyl, triazolyl, benzotriazolyl, quinolinyl, isoquinolinyl, quinazolinyl, or pyrimidinyl, or pyridinyl N-oxide each optionally substituted as defined in previous paragraph.

Some non-limiting examples of EWG' include, but are not limited to, —CH(haloalkyl), —NR'—, —S(O$_2$)—, —S(O)—, —CO—, —NR'CO—, —NR'SO$_2$—, —(OR')(O)P—,

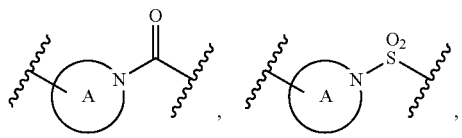

heteroaryl, or aryl; wherein each R' is independently hydrogen, alkyl, substituted alkyl, cycloalkyl; ring A is heterocycloamino where the carbonyl and sulfonyl groups are attached to —C(R$^{b'}$)=CHR$^c$ in the definition of R$^1$ and R$^5$ in compound of Formula (I); and heterocycloamino, aryl and heteroaryl are substituted with one, two or three substituents independently selected from hydrogen, alkyl, alkoxy, hydroxyl, cyano, nitro, halo, haloalkyl, haloalkoxy, alkylthio, alkylsulfonyl, carboxy, alkoxycarbonyl, aminocarbonyl or aminosulfonyl. Preferably, the heteroaryl ring is pyridinyl, pyrazolyl, indazolyl, indolyl, thienyl, pyrrolyl, imidazolyl, thiazolyl, benzothiazolyl, oxazolyl, benzimidazolyl, benzoxazolyl, isoxazolyl, benzisoxazolyl, triazolyl, benzotriazolyl, quinolinyl, isoquinolinyl, quinazolinyl, pyrimidinyl, or pyridinyl N-oxide each optionally substituted as defined in previous paragraph. In the groups above, the atom on the left is attached to Z and atom on the right is attached to —C(R$^{b'}$)=CHR$^c$ e.g., in —NR'CO—, —NR'— is attached to Z and CO is attached to —C(R$^{b'}$)=CHR$^c$ and in

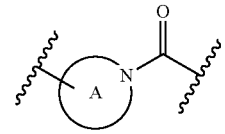

the carbonyl is attached to —C(R$^{b'}$)=CHR$^c$ and ring is attached to Z.

In some embodiments, a composition of the present disclosure comprises a compound corresponding to Formula (I) (or a pharmaceutically acceptable salt thereof) in which R$^1$ or R$^5$ is —Z-(EWG')-C(R$^{b'}$)=CHR$^c$ group, Z is a bond, and the ring in the compound of Formula (I) to which R$^1$ is attached i.e.,

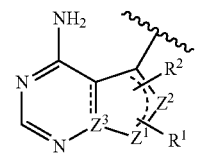

or the Ar ring to which R$^5$ is attached respectively, possesses an electron deficient π system. In such embodiments, Z and EWG' may each be bonds and the —C(R$^{b'}$)=CHR group is directly attached to the Ar or

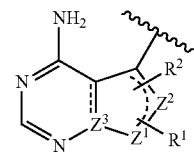

ring in the compound of Formula (I). In general, a ring has an electron deficient π system when it is substituted with an electron withdrawing group or the ring itself is electron deficient, e.g., a heteroaryl ring containing electronegative ring atoms such as nitrogen, oxygen or sulfur. For example, in the compounds of Formula (I), when Ar is phenyl, the phenyl ring can be electron deficient when it is substituted with an electron withdrawing group such as halo, cyano, or haloalkyl. By way of further example, the Ar ring can also be an electron deficient π system when it is heteroaryl, e.g., one of

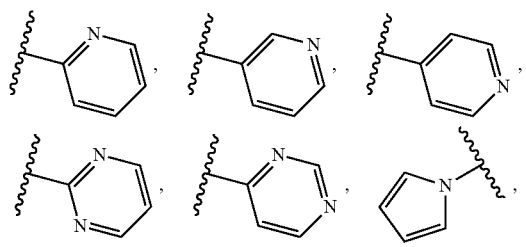

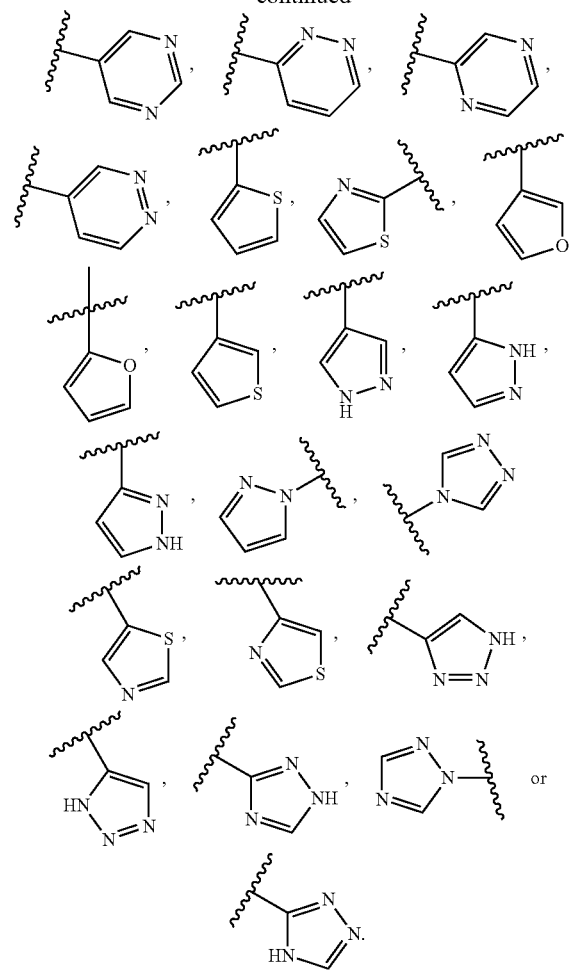

optionally substituted as defined above.

"Halo" means fluoro, chloro, bromo, or iodo, preferably fluoro or chloro.

"Haloalkyl" means alkyl radical as defined above, which is substituted with one or more halogen atoms, preferably one to five halogen atoms, preferably fluorine or chlorine, including those substituted with different halogens, e.g., —CH$_2$Cl, —CF$_3$, —CHF$_2$, —CH$_2$CF$_3$, —CF$_2$CF$_3$, —CF(CH$_3$)$_2$, and the like. When the alkyl is substituted with only fluoro, it is referred to in this application as fluoroalkyl.

"Haloalkoxy" means a —OR radical where R is haloalkyl as defined above e.g., —OCF$_3$, —OCHF$_2$, and the like. When R is haloalkyl where the alkyl is substituted with only fluoro, it is referred to in this application as fluoroalkoxy.

"Hydroxyalkyl" means a linear monovalent hydrocarbon radical of one to six carbon atoms or a branched monovalent hydrocarbon radical of three to six carbons substituted with one or two hydroxy groups, provided that if two hydroxy groups are present they are not both on the same carbon atom. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)-2-hydroxyethyl.

"Heterocyclyl" means a saturated or unsaturated monovalent monocyclic group of 4 to 8 ring atoms in which one or two ring atoms are heteroatom selected from N, O, or S(O)$_n$, where n is an integer from 0 to 2, the remaining ring atoms being C. The heterocyclyl ring is optionally fused to a (one) aryl or heteroaryl ring as defined herein provided the aryl and heteroaryl rings are monocyclic. The heterocyclyl ring fused to monocyclic aryl or heteroaryl ring is also referred to in this application as "bicyclic heterocyclyl" ring. Additionally, one or two ring carbon atoms in the heterocyclyl ring can optionally be replaced by a —CO— group. More specifically the term heterocyclyl includes, but is not limited to, pyrrolidino, piperidino, homopiperidino, 2-oxopyrrolidinyl, 2-oxopiperidinyl, morpholino, piperazino, tetrahydropyranyl, thiomorpholino, and the like. When the heterocyclyl ring is unsaturated it can contain one or two ring double bonds provided that the ring is not aromatic. When the heterocyclyl group contains at least one nitrogen atom, it is also referred to herein as heterocycloamino and is a subset of the heterocyclyl group. When the heterocyclyl group is a saturated ring and is not fused to aryl or heteroaryl ring as stated above, it is also referred to herein as saturated monocyclic heterocyclyl.

"Heterocyclylalkyl" means a -(alkylene)-R radical where R is heterocyclyl ring as defined above e.g., tetraydrofuranylmethyl, piperazinylmethyl, morpholinylethyl, and the like.

"Heterocycloamino" means a saturated or unsaturated monovalent monocyclic group of 4 to 8 ring atoms in which one or two ring atoms are heteroatom selected from N, O, or S(O)$_n$, where n is an integer from 0 to 2, the remaining ring atoms being C provided that at least one of the ring atoms is N. Additionally, one or two ring carbon atoms in the heterocycloamino ring can optionally be replaced by a —CO— group. When the heterocycloamino ring is unsaturated it can contain one or two ring double bonds provided that the ring is not aromatic. Unless otherwise stated, the heterocyloamino ring can optionally be substituted with one, two, or three substituents independently selected from alkyl, hydroxyl, alkoxy, amino, alkylamino, or dialkylamino.

"Heteroaryl" means a monovalent monocyclic or bicyclic aromatic radical of 5 to 10 ring atoms where one or more, preferably one, two, or three, ring atoms are heteroatom selected from N, O, or S, the remaining ring atoms being carbon. Representative examples include, but are not limited to, pyrrolyl, thienyl, thiazolyl, imidazolyl, furanyl, indolyl, isoindolyl, oxazolyl, isoxazolyl, benzothiazolyl, benzoxazolyl, quinolinyl, isoquinolinyl, pyridinyl, pyrimidinyl, pyrazinyl, pyridazinyl, triazolyl, tetrazolyl, and the like.

"Heteroalkylene" means a -(alkylene)- radical where one, two or three carbons in the alkylene chain is replaced by —O—, N(H, alkyl, or substituted alkyl), S, SO, SO$_2$, or CO.

"Heteroaralkyl" means an -alkylene- radical where R is heteroaryl as defined above.

"Monosubstituted amino" means a —NHR radical where R is alkyl, cycloalkyl, cycloalkylalkyl, acyl, sulfonyl, aryl, aralkyl, heteroaryl, heteroaralkyl, heterocyclyl, heterocyclylalkyl, or substituted alkyl, each as defined herein and wherein the aryl, heteroaryl, or heterocyclyl ring either alone or part of another group e.g., aralkyl, is optionally substituted with one, two, or three substituents independently selected from alkyl, alkoxy, halo, haloalkoxy, hydroxyl, carboxy, or alkoxycarbonyl, e.g., methylamino, phenylamino, hydroxyethylamino, and the like.

The present disclosure also includes the prodrugs of compounds of Formula (I). The term prodrug is intended to represent covalently bonded carriers, which are capable of releasing the active ingredient of Formula (I) when the prodrug is administered to a mammalian subject. Release of the active ingredient occurs in vivo. Prodrugs can be prepared by techniques known to one skilled in the art. These techniques generally modify appropriate functional groups in a given compound. These modified functional groups however regenerate original functional groups in vivo or by routine manipulation. Prodrugs of compounds of Formula (I) include compounds wherein a hydroxy, amino, carboxylic, or a similar group is modified. Examples of prodrugs include, but are not limited to esters (e.g., acetate, formate, and benzoate derivatives), carbamates (e.g., N,N-dimethylaminocarbonyl) of hydroxy or amino functional groups in compounds of Formula (I)), amides (e.g., trifluoroacetylamino, acetylamino, and the like), and the like. Prodrugs of compounds of Formula (I) are also within the scope of this disclosure.

The present disclosure also includes protected derivatives of compounds of Formula (I). For example, when compounds of Formula (I) contain groups such as hydroxy, carboxy, thiol or any group containing a nitrogen atom(s), these groups can be protected with a suitable protecting groups. A comprehensive list of suitable protective groups can be found in T. W. Greene, *Protective Groups in Organic Synthesis*, John Wiley & Sons, Inc. (1999), the disclosure of which is incorporated herein by reference in its entirety. The protected derivatives of compounds of Formula (I) can be prepared by methods well known in the art.

The present disclosure also includes polymorphic forms (amorphous as well as crystalline) and deuterated forms of compounds of Formula (I).

A "pharmaceutically acceptable salt" of a compound means a salt that is pharmaceutically acceptable and that possesses the desired pharmacological activity of the parent compound. Such salts include:

acid addition salts, formed with inorganic acids such as hydrochloric acid, hydrobromic acid, sulfuric acid, nitric acid, phosphoric acid, and the like; or formed with organic acids such as formic acid, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. It is understood that the pharmaceutically acceptable salts are non-toxic. Additional information on suitable pharmaceutically acceptable salts can be found in *Remington's Pharmaceutical Sciences*, 17th ed., Mack Publishing Company, Easton, Pa., 1985, which is incorporated herein by reference.

The compounds of the present disclosure may have asymmetric centers. Compounds of the present disclosure containing an asymmetrically substituted atom may be isolated in optically active or racemic forms. It is well known in the art how to prepare optically active forms, such as by resolution of materials. All chiral, diastereomeric, racemic forms are within the scope of this disclosure, unless the specific stereochemistry or isomeric form is specifically indicated.

Certain compounds of Formula (I) can exist as tautomers and/or geometric isomers. All possible tautomers and cis and trans isomers, as individual forms and mixtures thereof are within the scope of this disclosure. Additionally, as used herein the term alkyl includes all the possible isomeric forms of said alkyl group albeit only a few examples are set forth. Furthermore, when the cyclic groups such as aryl, heteroaryl, heterocyclyl are substituted, they include all the positional isomers albeit only a few examples are set forth. Furthermore, all polymorphic forms and hydrates of a compound of Formula (I) are within the scope of this disclosure.

"Oxo" or "carbonyl" means C=(O) group.

"Optional" or "optionally" means that the subsequently described event or circumstance may but need not occur, and that the description includes instances where the event or circumstance occurs and instances in which it does not. For example, "heterocyclyl group optionally substituted with an alkyl group" means that the alkyl may but need not be present, and the description includes situations where the heterocyclyl group is substituted with an alkyl group and situations where the heterocyclyl group is not substituted with alkyl.

A "pharmaceutically acceptable carrier or excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. "A pharmaceutically acceptable carrier/excipient" as used in the specification and claims includes both one and more than one such excipient.

"Sulfonyl" means a —SO$_2$R radical where R is alkyl, haloalkyl, aryl, aralkyl, heteroaryl, heteroaralkyl, heterocyclyl, heterocyclylalkyl, each as defined herein and wherein the aryl, heteroaryl, or heterocyclyl ring either alone or part of another group e.g., aralkyl, is optionally substituted with one, two, or three substituents independently selected from alkyl, alkoxy, halo, haloalkoxy, hydroxyl, carboxy, or alkoxycarbonyl, e.g., methylsulfonyl, phenylsulfonyl, benzylsulfonyl, pyridinylsulfonyl, and the like.

"Substituted alkyl" means alkyl group as defined herein which is substituted with one, two, or three substituents independently selected from hydroxyl, alkoxy, carboxy, cyano, alkoxycarbonyl, alkylthio, alkylsulfonyl, halo, haloalkoxy, —CONRR' or —NRR' (where each R is hydrogen, alkyl, hydroxyalkyl, or alkoxyalkyl, and each R' is hydrogen, alkyl, or cycloalkyl) or heterocyclyl (preferably heterocycloamino) optionally substituted with one or two groups independently selected from alkyl, hydroxyl, alkoxy, alkylthio, alkylsulfonyl, halo, or —CONRR' where R and R' are as defined above. When the alkyl group is substituted with only hydroxy, the group is also referred to herein as hydroxyalkyl and is a subset of substituted alkyl.

"Treating" or "treatment" of a disease includes:

(1) preventing the disease, i.e. causing the clinical symptoms of the disease not to develop in a mammal that may be exposed to or predisposed to the disease but does not yet experience or display symptoms of the disease;

(2) inhibiting the disease, i.e., arresting or reducing the development of the disease or its clinical symptoms; or (3) relieving the disease, i.e., causing regression of the disease or its clinical symptoms.

A "therapeutically effective amount" means the amount of a compound of Formula (I) that, when administered to a mammal for treating a disease, is sufficient to effect such treatment for the disease. The "therapeutically effective amount" will vary depending on the compound, the disease and its severity and the age, weight, etc., of the mammal to be treated.

The abbreviations appearing in the Embodiment E of the embodiments section shall have the following meanings:

I(a), I(b), I(c), I(d), and I(e) shall mean a compound corresponding to Formula I having the substituents described in subpart (a), subpart (b), subpart (d) and subpart (d), respectively, of Embodiment E.

A(a), A(b), A(c), A(d), and A(e) shall mean a compound corresponding to Formula I having the substituents described in Embodiment A and subpart (a), subpart (b), subpart (d) and subpart (d), respectively, of Embodiment E.

B(a), B(b), B(c), B(d), and B(e) shall mean a compound corresponding to Formula I having the substituents described in Embodiment B and subpart (a), subpart (b), subpart (d) or subpart (d), respectively, of Embodiment E.

C(a), C(b), C(c), C(d), and C(e) shall mean a compound corresponding to Formula I having the substituents described in Embodiment C and subpart (a), subpart (b), subpart (d) and subpart (d), respectively, of Embodiment E.

D(a), D(b), D(c), D(d), and D(e) shall mean a compound corresponding to Formula I having the substituents described in Embodiment D and subpart (a), subpart (b), subpart (d) and subpart (d), respectively, of Embodiment E.

I(a,c), I(a,d), I(a,e), I(b,c), I(b,d), and I(b,e) shall mean a compound corresponding to Formula I having the substituents described in subparts (a) and (c), subparts (a) and (d), subparts (a) and (e), subparts (b) and (c), subparts (b) and (d) and subparts (b) and (e), respectively, of Embodiment E.

A(a,c), A(a,d), A(a,e), A(b,c), A(b,d), and A(b,e) shall mean a compound corresponding to Formula I having the substituents described in Embodiment A and subparts (a) and (c), subparts (a) and (d), subparts (a) and (e), subparts (b) and (c), subparts (b) and (d) and subparts (b) and (e), respectively, of Embodiment E.

B(a,c), B(a,d), B(a,e), B(b,c), B(b,d), and B(b,e) shall mean a compound corresponding to Formula I having the substituents described in Embodiment B and subparts (a) and (c), subparts (a) and (d), subparts (a) and (e), subparts (b) and (c), subparts (b) and (d) and subparts (b) and (e), respectively, of Embodiment E.

C(a,c), C(a,d), C(a,e), C(b,c), C(b,d), and C(b,e) shall mean a compound corresponding to Formula I having the substituents described in Embodiment C and subparts (a) and (c), subparts (a) and (d), subparts (a) and (e), subparts (b) and (c), subparts (b) and (d) and subparts (b) and (e), respectively, of Embodiment E.

D(a,c), D(a,d), D(a,e), D(b,c), D(b,d), and D(b,e) shall mean a compound corresponding to Formula I having the substituents described in Embodiment D and subparts (a) and (c), subparts (a) and (d), subparts (a) and (e), subparts (b) and (c), subparts (b) and (d) and subparts (b) and (e), respectively, of Embodiment E.

I(a,i), I(b,i), I(c,i), I(d,i), and I(e,i) shall mean a compound corresponding to Formula I having the substituents described subparts (a) and (i), subparts (b) and (i), subparts (c) and (i), subparts (d) and (i), and subparts (e) and (i), respectively, of Embodiment E.

A(a,i), A(b,i), A(c,i), A(d,i), and A(e,i) shall mean a compound corresponding to Formula I having the substituents described in Embodiment A and subparts (a) and (i), subparts (b) and (i), subparts (c) and (i), subparts (d) and (i), and subparts (e) and (i), respectively, of Embodiment E.

B(a,i), B(b,i), B(c,i), B(d,i), and B(e,i) shall mean a compound corresponding to Formula I having the substituents described in Embodiment B and subparts (a) and (i), subparts (b) and (i), subparts (c) and (i), subparts (d) and (i), and subparts (e) and (i), respectively, of Embodiment E.

C(a,i), C(b,i), C(c,i), C(d,i), and C(e,i) shall mean a compound corresponding to Formula I having the substituents described in Embodiment C and subparts (a) and (i), subparts (b) and (i), subparts (c) and (i), subparts (d) and (i), and subparts (e) and (i), respectively, of Embodiment E.

D(a,i), D(b,i), D(c,i), D(d,i), and D(e,i) shall mean a compound corresponding to Formula I having the substituents described in Embodiment D and subparts (a) and (i), subparts (b) and (i), subparts (c) and (i), subparts (d) and (i), and subparts (e) and (i), respectively, of Embodiment E.

I(a,c,i), I(a,d,i), I(a,e,i), I(b,c,i), I(b,d,i), and I(b,e,i) shall mean a compound corresponding to Formula I having the substituents described in subparts (a), (c) and (i), subparts (a), (d) and (i), subparts (a), (e) and (i), subparts (b), (c) and (i), subparts (b), (d) and (i) and subparts (b), (e) and (i), respectively, of Embodiment E.

A(a,c,i), A(a,d,i), A(a,e,i), A(b,c,i), A(b,d,i), and A(b,e,i) shall mean a compound corresponding to Formula I having the substituents described in Embodiment A and subparts (a), (c) and (i), subparts (a), (d) and (i), subparts (a), (e) and (i), subparts (b), (c) and (i), subparts (b), (d) and (i) and subparts (b), (e) and (i), respectively, of Embodiment E.

B(a,c,i), B(a,d,i), B(a,e,i), B(b,c,i), B(b,d,i), and B(b,e,i) shall mean a compound corresponding to Formula I having the substituents described in Embodiment B and subparts (a), (c) and (i), subparts (a), (d) and (i), subparts (a), (e) and (i), subparts (b), (c) and (i), subparts (b), (d) and (i) and subparts (b), (e) and (i), respectively, of Embodiment E.

C(a,c,i), C(a,d,i), C(a,e,i), C(b,c,i), C(b,d,i), and C(b,e,i) shall mean a compound corresponding to Formula I having the substituents described in Embodiment C and subparts (a), (c) and (i), subparts (a), (d) and (i), subparts (a), (e) and (i), subparts (b), (c) and (i), subparts (b), (d) and (i) and subparts (b), (e) and (i), respectively, of Embodiment E.

D(a,c,i), D(a,d,i), D(a,e,i), D(b,c,i), D(b,d,i), and D(b,e,i) shall mean a compound corresponding to Formula I having the substituents described in Embodiment D and subparts (a), (c) and (i), subparts (a), (d) and (i), subparts (a), (e) and (i), subparts (b), (c) and (i), subparts (b), (d) and (i) and subparts (b), (e) and (i), respectively, of Embodiment E.

I(a,ii), I(b,ii), I(c,ii), I(d,ii), and I(e,ii) shall mean a compound corresponding to Formula I having the substituents described in subparts (a) and (ii), subparts (b) and (ii), subparts (c) and (ii), subparts (d) and (ii), and subparts (e) and (ii), respectively, of Embodiment E.

A(a,ii), A(b,ii), A(c,ii), A(d,ii), and A(e,ii) shall mean a compound corresponding to Formula I having the substituents described in Embodiment A and subparts (a) and (ii), subparts (b) and (ii), subparts (c) and (ii), subparts (d) and (ii), and subparts (e) and (ii), respectively, of Embodiment E.

B(a,ii), B(b,ii), B(c,ii), B(d,ii), and B(e,ii) shall mean a compound corresponding to Formula I having the substituents described in Embodiment B and subparts (a) and (ii), subparts (b) and (ii), subparts (c) and (ii), subparts (d) and (ii), and subparts (e) and (ii), respectively, of Embodiment E.

C(a,ii), C(b,ii), C(c,ii), C(d,ii), and C(e,ii) shall mean a compound corresponding to Formula I having the substituents described in Embodiment C and subparts (a) and (ii), subparts (b) and (ii), subparts (c) and (ii), subparts (d) and (ii), and subparts (e) and (ii), respectively, of Embodiment E.

D(a,ii), D(b,ii), D(c,ii), D(d,ii), and D(e,ii) shall mean a compound corresponding to Formula I having the substituents described in Embodiment D and subparts (a) and (ii), subparts (b) and (ii), subparts (c) and (ii), subparts (d) and (ii), and subparts (e) and (ii), respectively, of Embodiment E.

I(a,c,ii), I(a,d,ii), I(a,e,ii), I(b,c,ii), I(b,d,ii), and I(b,e,ii) shall mean a compound corresponding to Formula I having the substituents described in subparts (a), (c) and (ii), subparts (a), (d) and (ii), subparts (a), (e) and (ii), subparts (b), (c) and (ii), subparts (b), (d) and (ii) and subparts (b), (e) and (ii), respectively, of Embodiment E.

A(a,c,ii), A(a,d,ii), A(a,e,ii), A(b,c,ii), A(b,d,ii), and A(b,e,ii) shall mean a compound corresponding to Formula I having the substituents described in Embodiment A and subparts (a), (c) and (ii), subparts (a), (d) and (ii), subparts (a), (e) and (ii), subparts (b), (c) and (ii), subparts (b), (d) and (ii) and subparts (b), (e) and (ii), respectively, of Embodiment E.

B(a,c,ii), B(a,d,ii), B(a,e,ii), B(b,c,ii), B(b,d,ii), and B(b,e,ii) shall mean a compound corresponding to Formula I having the substituents described in Embodiment B and subparts (a), (c) and (ii), subparts (a), (d) and (ii), subparts (a), (e) and (ii), subparts (b), (c) and (ii), subparts (b), (d) and (ii) and subparts (b), (e) and (ii), respectively, of Embodiment E.

C(a,c,ii), C(a,d,ii), C(a,e,ii), C(b,c,ii), C(b,d,ii), and C(b,e,ii) shall mean a compound corresponding to Formula I having the substituents described in Embodiment C and subparts (a), (c) and (ii), subparts (a), (d) and (ii), subparts (a), (e) and (ii), subparts (b), (c) and (ii), subparts (b), (d) and (ii) and subparts (b), (e) and (ii), respectively, of Embodiment E.

D(a,c,ii), D(a,d,ii), D(a,e,ii), D(b,c,ii), and D(b,d,ii) and D(b,e,ii) shall mean a compound corresponding to Formula I having the substituents described in Embodiment D and subparts (a), (c) and (ii), subparts (a), (d) and (ii), subparts (a), (e) and (ii), subparts (b), (c) and (ii), subparts (b), (d) and (ii) and subparts (b), (e) and (ii), respectively, of Embodiment E.

EMBODIMENTS

Embodiment A

In one embodiment, a compound of Formula (I) as defined above (or a pharmaceutically acceptable salt thereof) in which the fused bicyclic moiety thereof has the structure:

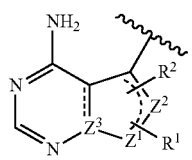

is:

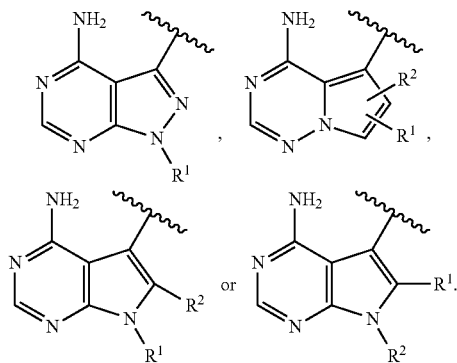

Preferably,

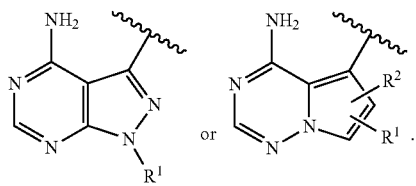

Preferably,

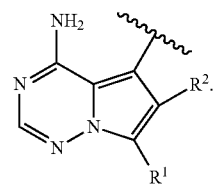

Preferably

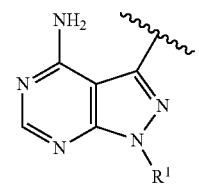

Preferably,

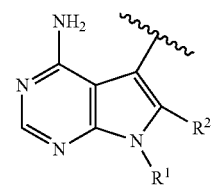

Embodiment B

In another embodiment, a compound of Formula (I) as defined in above (or a pharmaceutically acceptable salt thereof) or as more specifically defined in embodiment (A) an groups contained therein, in one group of compounds L is O, S, $SO_2$, NR, NHCO, CONH, or NHCONH; preferably O, S, NH, or N(methyl), or NHCONH; more preferably L is O or NHCONH. Within this embodiment, in one group of compounds L is O. Within this embodiment, in one group of compounds L is NHCONH, NHCO, or CONH, preferably NHCONH. Within this embodiment and groups contained therein, in one group of compounds $R^2$ is hydrogen, methyl, fluoro, or trifluoromethyl, preferably hydrogen.

Embodiment C

In another embodiment, a compound of Formula (I) as defined above (or a pharmaceutically acceptable salt thereof) or as more specifically defined in embodiments (A) and/or (B) and groups contained therein, in one group of compounds $R^3$ and $R^4$ are independently hydrogen, alkyl, alkoxy, cyano, halo, haloalkyl or haloalkoxy; preferably $R^3$ and $R^4$ are independently hydrogen, methyl, fluoro, methoxy, chloro, trifluoromethyl, or trifluoromethoxy. Preferably, $R^3$ and $R^4$ are independently hydrogen or fluoro. Preferably, in one group of compounds is a ring of fomula:

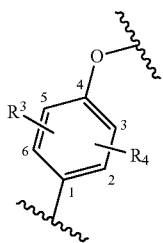

where R³ is hydrogen, methyl, ethyl, chloro, fluoro or trifluoromethyl, preferably methyl, ethyl, chloro or fluoro, more preferably, hydrogen, methyl, fluoro, or chloro, even more preferably hydrogen, chloro or fluoro, particularly preferably hydrogen or fluoro. Preferably, within groups in (C), in another group of compounds

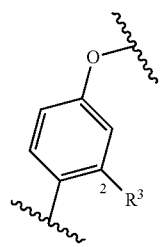

is a ring of formula

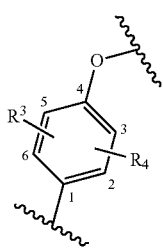

where R³ is alkyl or halo, preferably methyl, chloro or fluoro. Preferably, within groups in (C), in yet another group of compounds

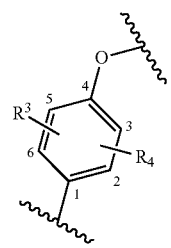

is a ring of formula

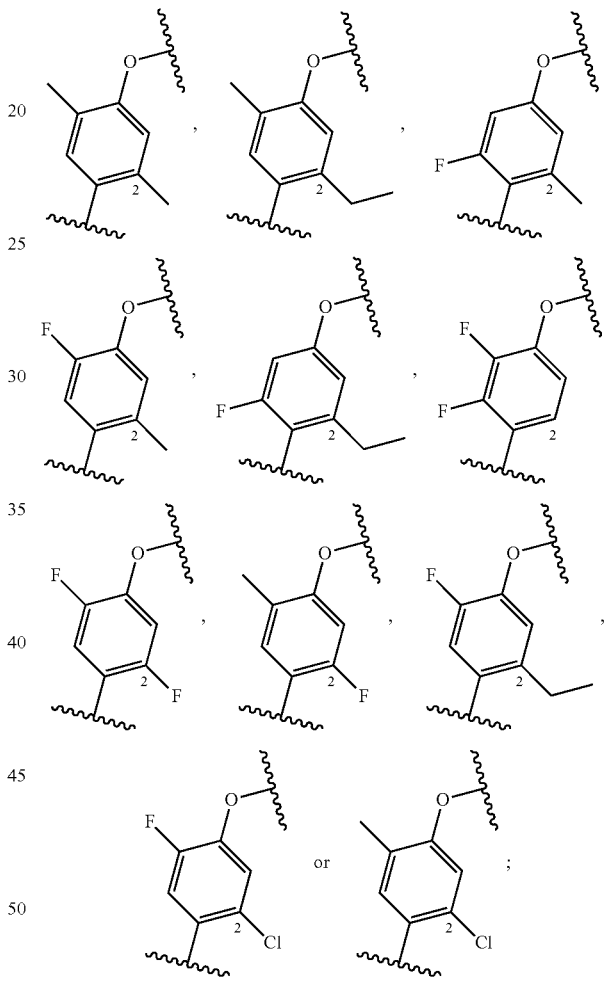

preferably,

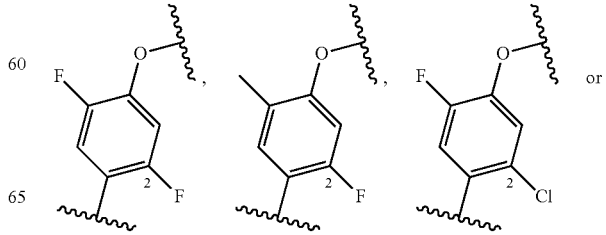

-continued

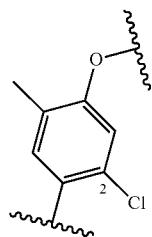

Embodiment D

In another embodiment, a compound of Formula (I) as defined above (or a pharmaceutically acceptable salt thereof) or as more specifically defined in embodiments (A), (B) and/or (C) and groups contained therein, in one group of compounds $R^6$ and $R^7$ are independently hydrogen, alkyl, alkoxy, halo, haloalkyl, haloalkoxy, or cyano. Preferably, $R^6$ and $R^7$ are independently hydrogen, methyl, methoxy, fluoro, chloro, trifluoromethyl, trifluoromethoxy, or cyano. Preferably,

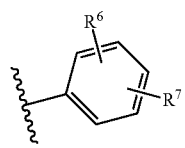

is a ring of formula:

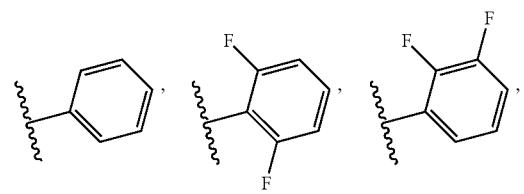

Preferably,

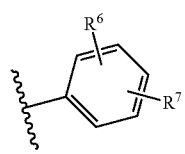

is a ring of formula:

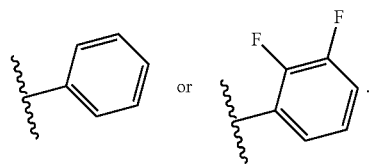 [SMILES: *c1ccccc1 ; *c1cccc(F)c1F]

Embodiment E

In another embodiment, a compound of Formula (I) as defined above (or a pharmaceutically acceptable salt thereof) or as more specifically defined in embodiments (A), (B), (C) and/or (D) and groups contained therein, in one group of compounds:

(a) $R^5$ is hydrogen, alkyl, alkoxy, halo, haloalkyl, haloalkoxy, or cyano. Preferably, $R^5$ is hydrogen, methyl, methoxy, fluoro, chloro, trifluoromethyl, trifluoromethoxy, or cyano; and $R^1$ is —P-Q-CH=C($R^b$)(EWG) where P is a bond, $NR^a$ (where $R^a$ is hydrogen or alkyl), —O—, —S—, —S(O)—, —S(O$_2$)—, or alkylene, Q is a bond, aryl or heteroaryl, $R^b$ is cyano, nitro, halo, haloalkyl, haloalkoxy, alkylthio, or alkylsulfonyl, EWG is an electron withdrawing group; and L is O.

(b) In another group of compounds $R^1$ is hydrogen, alkyl, alkoxy, halo, haloalkyl, haloalkoxy, or cyano. Preferably, $R^1$ is hydrogen, methyl, methoxy, fluoro, chloro, trifluoromethyl, trifluoromethoxy, or cyano; and $R^5$ is —P-Q-CH=C($R^b$)(EWG) where P is a bond, $NR^a$ (where $R^a$ is hydrogen or alkyl), —O—, —S—, —S(O)—, —S(O$_2$)—, alkylene or heteroalkylene, Q is a bond, aryl or heteroaryl, $R^b$ is cyano, nitro, halo, haloalkyl, haloalkoxy, alkylthio, or alkylsulfonyl, EWG is an electron withdrawing group; and L is NHCONH, NHCO, or CONH.

(c) Within the groups in embodiment E, in one group of compounds —P— is bond, $NR^a$, O, or methylene and Q is aryl or heteroaryl, preferably, Q is selected from:

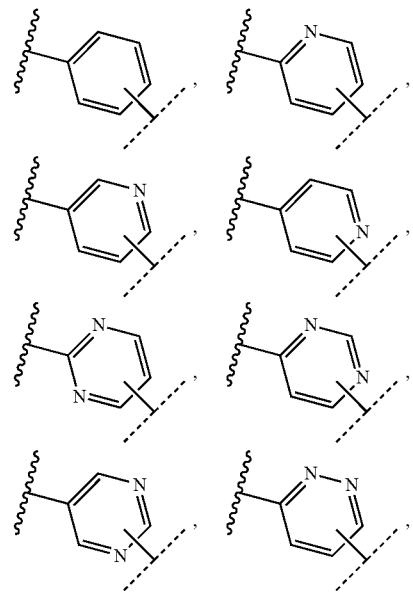

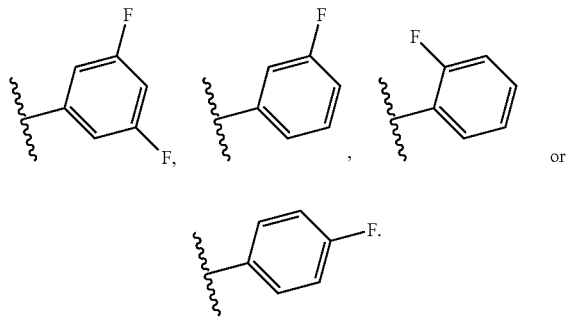

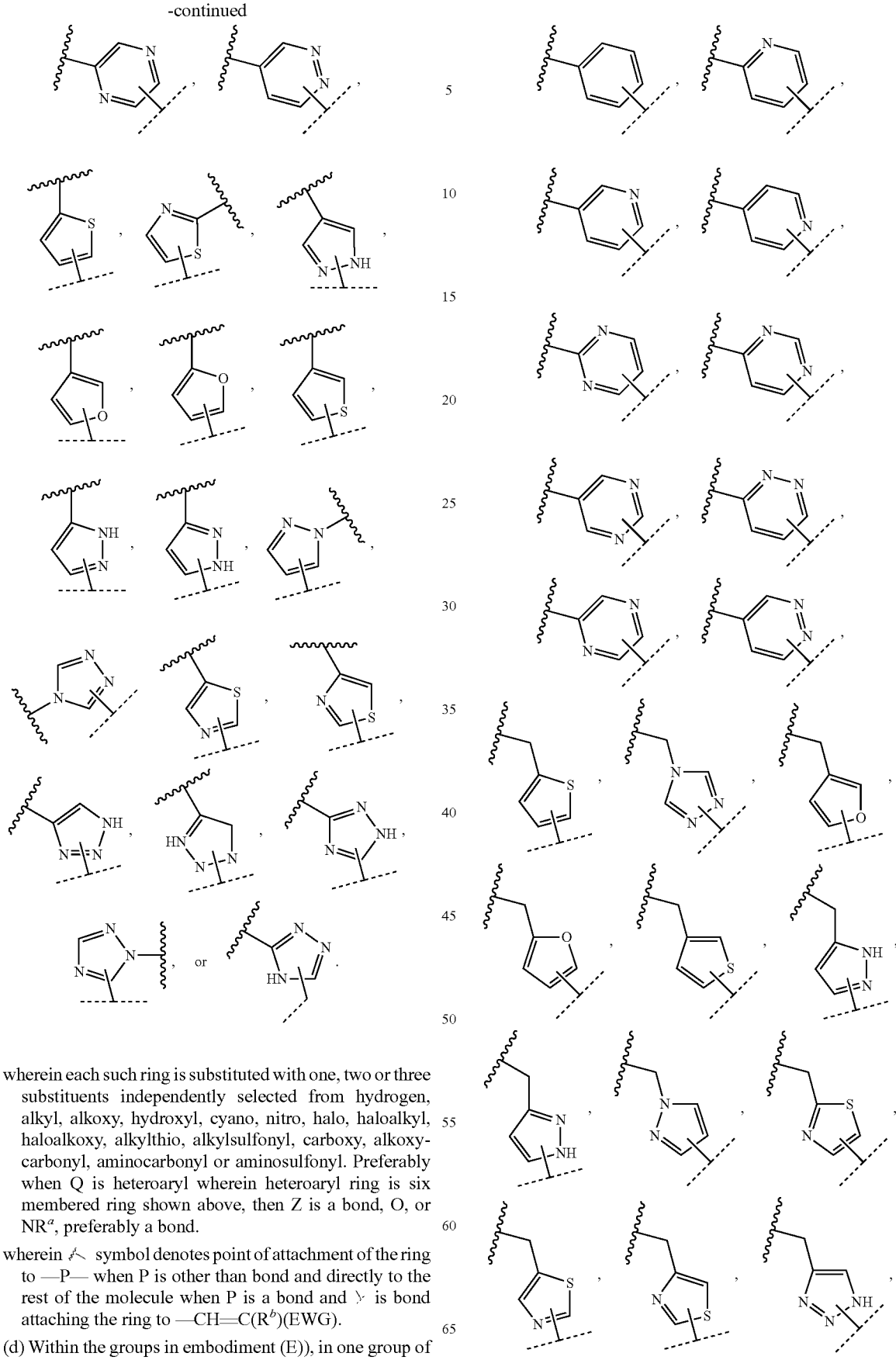

wherein each such ring is substituted with one, two or three substituents independently selected from hydrogen, alkyl, alkoxy, hydroxyl, cyano, nitro, halo, haloalkyl, haloalkoxy, alkylthio, alkylsulfonyl, carboxy, alkoxycarbonyl, aminocarbonyl or aminosulfonyl. Preferably when Q is heteroaryl wherein heteroaryl ring is six membered ring shown above, then Z is a bond, O, or NR$^a$, preferably a bond.

wherein ⌇ symbol denotes point of attachment of the ring to —P— when P is other than bond and directly to the rest of the molecule when P is a bond and ⌇ is bond attaching the ring to —CH═C(R$^b$)(EWG).

(d) Within the groups in embodiment (E)), in one group of compounds —P-Q- is selected from:

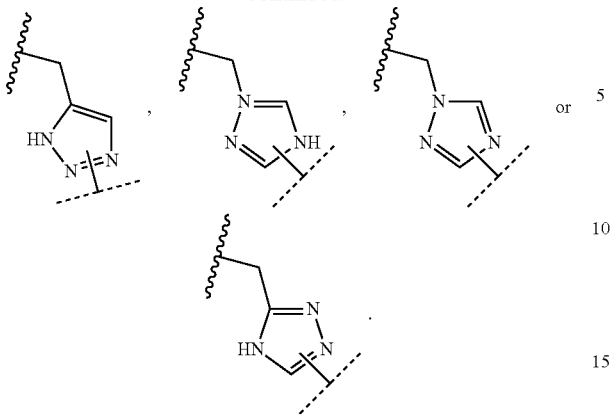

each substituted with one, two or three substituents independently selected from hydrogen, alkyl, alkoxy, hydroxyl, cyano, nitro, halo, haloalkyl, haloalkoxy, alkylthio, alkylsulfonyl, carboxy, alkoxycarbonyl, aminocarbonyl or aminosulfonyl.

(e) Within the groups in embodiment (E) in another group of compounds —P-Q- is selected from: phenyl, 2-, 3-, or 4-pyridyl substituted as defined above. Preferably, —P-Q- is selected from: unsubstituted phenyl, 2-, 3-, or 4-pyridyl.

(f) Within the groups in embodiment I(b), A(b), B(b), C(b), and D(b), in one group of compounds —P-Q- is a bond.

(i) Within the above groups in embodiment (E), e.g., Formula I, I(a), I(b), I(c), I(d), I(e), A(a), A(b), A(c), A(d), A(e), B(a), B(b), B(c), B(d), B(e), C(a), C(b), C(c), C(d), C(e), D(a), D(b), D(c), D(d), D(e), I(a,c), I(a,d), I(a,e), I(b,c), I(b,d), I(b,e), A(a,c), A(a,d), A(a,e), A(b,c), A(b,d), A(b,e), B(a,c), B(a,d), B(a,e), B(b,c), B(b,d), B(b,e), C(a,c), C(a,d), C(a,e), C(b,c), C(b,d), C(b,e), D(a,c), D(a,d), D(a,e), D(b,c), D(b,d), and D(b,e), and groups contained therein, in one group of compounds when Q is a six membered ring, then the —CH=C($R^b$)(EWG) group is attached to the carbon atom in the six membered ring that is preferably meta to the carbon atom that attaches the six membered ring to —P—.

(ii) Within the above groups in embodiment (E), e.g., Formula I, I(a), I(b), I(c), I(d), I(e), A(a), A(b), A(c), A(d), A(e), B(a), B(b), B(c), B(d), B(e), C(a), C(b), C(c), C(d), C(e), D(a), D(b), D(c), D(d), D(e), I(a,c), I(a,d), I(a,e), I(b,c), I(b,d), I(b,e), A(a,c), A(a,d), A(a,e), A(b,c), A(b,d), A(b,e), B(a,c), B(a,d), B(a,e), B(b,c), B(b,d), B(b,e), C(a,c), C(a,d), C(a,e), C(b,c), C(b,d), C(b,e), D(a,c), D(a,d), D(a,e), D(b,c), D(b,d), and D(b,e), and groups contained therein, in one group of compounds when Q is a five membered ring, then the —CH=C($R^b$)(EWG) group is attached to the atom in the five membered ring that is preferably ortho to the atom that attaches the five membered ring to —P—.

(iii) Within the above groups in embodiment (E), e.g., Formula I, I(a), I(b), I(c), I(d), I(e), A(a), A(b), A(c), A(d), A(e), B(a), B(b), B(c), B(d), B(e), C(a), C(b), C(c), C(d), C(e), D(a), D(b), D(c), D(d), D(e), I(a,c), I(a,d), I(a,e), I(b,c), I(b,d), I(b,e), A(a,c), A(a,d), A(a,e), A(b,c), A(b,d), A(b,e), B(a,c), B(a,d), B(a,e), B(b,c), B(b,d), B(b,e), C(a,c), C(a,d), C(a,e), C(b,c), C(b,d), C(b,e), D(a,c), D(a,d), D(a,e), D(b,c), D(b,d), D(b,e), I(a,i), I(b,i), I(c,i), I(d,i), I(e,i), A(a,i), A(b,i), A(c,i), A(d,i), A(e,i), B(a,i), B(b,i), B(c,i), B(d,i), B(e,i), C(a,i), C(b,i), C(c,i), C(d,i), C(e,i), D(a,i), D(b,i), D(c,i), D(d,i), D(e,i), I(a,c,i), I(a,d,i), I(a,e,i), I(b,c,i), I(b,d,i), I(b,e,i), A(a,c,i), A(a,d,i), A(a,e,i), A(b,c,i), A(b,d,i), A(b,e,i), B(a,c,i), B(a,d,i), B(a,e,i), B(b,c,i), B(b,d,i), B(b,e,i), C(a,c,i), C(a,d,i), C(a,e,i), C(b,c,i), C(b,d,i), C(b,e,i), D(a,c,i), D(a,d,i), D(a,e,i), D(b,c,i), D(b,d,i), D(b,e,i), I(a,ii), I(b,ii), I(c,ii), I(d,ii), I(e,ii), A(a,ii), A(b,ii), A(c,ii), A(d,ii), A(e,ii), B(a,ii), B(b,ii), B(c,ii), B(d,ii), B(e,ii), C(a,ii), C(b,ii), C(c,ii), C(d,ii), C(e,ii), D(a,ii), D(b,ii), D(c,ii), D(d,ii), D(e,ii), I(a,c,ii), I(a,d,ii), I(a,e,ii), I(b,c,ii), I(b,d,ii), I(b,e,ii), A(a,c,ii), A(a,d,ii), A(a,e,ii), A(b,c,ii), A(b,d,ii), A(b,e,ii), B(a,c,ii), B(a,d,ii), B(a,e,ii), B(b,c,ii), B(b,d,ii), B(b,e,ii), C(a,c,ii), C(a,d,ii), C(a,e,ii), C(b,c,ii), C(b,d,ii), C(b,e,ii), D(a,c,ii), D(a,d,ii), D(a,e,ii), D(b,c,ii), D(b,d,ii) and D(b,e,ii), and groups contained therein, in one group of compounds $R^b$ is cyano.

(iv) Within the above groups in embodiment (E), e.g., Formula I, I(a), I(b), I(c), I(d), I(e), A(a), A(b), A(c), A(d), A(e), B(a), B(b), B(c), B(d), B(e), C(a), C(b), C(c), C(d), C(e), D(a), D(b), D(c), D(d), D(e), I(a,c), I(a,d), I(a,e), I(b,c), I(b,d), I(b,e), A(a,c), A(a,d), A(a,e), A(b,c), A(b,d), A(b,e), B(a,c), B(a,d), B(a,e), B(b,c), B(b,d), B(b,e), C(a,c), C(a,d), C(a,e), C(b,c), C(b,d), C(b,e), D(a,c), D(a,d), D(a,e), D(b,c), D(b,d), D(b,e), I(a,i), I(b,i), I(c,i), I(d,i), I(e,i), A(a,i), A(b,i), A(c,i), A(d,i), A(e,i), B(a,i), B(b,i), B(c,i), B(d,i), B(e,i), C(a,i), C(b,i), C(c,i), C(d,i), C(e,i), D(a,i), D(b,i), D(c,i), D(d,i), D(e,i), I(a,c,i), I(a,d,i), I(a,e,i), I(b,c,i), I(b,d,i), I(b,e,i), A(a,c,i), A(a,d,i), A(a,e,i), A(b,c,i), A(b,d,i), A(b,e,i), B(a,c,i), B(a,d,i), B(a,e,i), B(b,c,i), B(b,d,i), B(b,e,i), C(a,c,i), C(a,d,i), C(a,e,i), C(b,c,i), C(b,d,i), C(b,e,i), D(a,c,i), A(a,ii), A(b,ii), A(c,ii), A(d,ii), A(e,ii), B(a,ii), B(b,ii), B(c,ii), B(d,ii), B(e,ii), C(a,ii), C(b,ii), C(c,ii), C(d,ii), C(e,ii), D(a,ii), D(b,ii), D(c,ii), D(d,ii), D(e,ii), I(a,c,ii), I(a,d,ii), I(a,e,ii), I(b,c,ii), I(b,d,ii), I(b,e,ii), A(a,c,ii), A(a,d,ii), A(a,e,ii), A(b,c,ii), A(b,d,ii), A(b,e,ii), B(a,c,ii), B(a,d,ii), B(a,e,ii), B(b,c,ii), B(b,d,ii), B(b,e,ii), C(a,c,ii), C(a,d,ii), C(a,e,ii), C(b,c,ii), C(b,d,ii), C(b,e,ii), D(a,c,ii), D(a,d,ii), D(a,e,ii), D(b,c,ii), D(b,d,ii) and D(b,e,i), and groups contained therein, in another group of compounds $R^b$ is trifluoromethyl.

(v) Within the above groups in embodiment (E), e.g., Formula I, I(a), I(b), I(c), I(d), I(e), A(a), A(b), A(c), A(d), A(e), B(a), B(b), B(c), B(d), B(e), C(a), C(b), C(c), C(d), C(e), D(a), D(b), D(c), D(d), D(e), I(a,c), I(a,d), I(a,e), I(b,c), I(b,d), I(b,e), A(a,c), A(a,d), A(ae), A(b,c), A(b,d), A(b,e), B(a,c), B(a,d), B(a,e), B(b,c), B(b,d), B(b,e), C(a,c), C(a,d), C(a,e), C(b,c), C(b,d), C(b,e), D(a,c), D(ad), D(a,e), D(b,c), D(b,d), D(b,e), I(a,i), I(b,i), I(c,i), I(d,i), I(e,i), A(a,i), A(b,i), A(c,i), A(d,i), A(e,i), B(a,i), B(b,i), B(c,i), B(d,i), B(e,i), C(a,i), C(b,i), C(c,i), C(d,i), C(e,i), D(a,i), D(b,i), D(c,i), D(d,i), D(e,i), I(a,c,i), I(a,d,i), I(a,e,i), I(b,c,i), I(b,d,i), I(b,e,i), A(a,c,i), A(a,d,i), A(a,e,i), A(b,c,i), A(b,d,i), A(b,e,i), B(a,c,i), B(a,d,i), B(a,e,i), B(b,c,i), B(b,d,i), B(b,e,i), C(a,c,i), C(a,d,i), C(a,e,i), C(b,c,i), C(b,d,i), C(b,e,i), D(a,c,i), D(a,d,i), D(a,e,i), D(b,c,i), D(b,d,i), D(b,e,i), I(a,ii), I(b,ii), I(c,ii), I(d,ii), I(e,ii), A(a,ii), A(b,ii), A(c,ii), A(d,ii), A(e,ii), B(a,ii), B(b,ii), B(c,ii), B(d,ii), B(e,ii), C(a,ii), C(b,ii), C(c,ii), C(d,ii), C(e,ii), D(a,ii), D(b,ii), D(c,ii), D(d,ii), D(e,ii), I(a,c,ii), I(a,d,ii), I(a,e,ii), I(b,c,ii), I(b,d,ii), I(b,e,ii), A(a,c,ii), A(a,d,ii), A(a,e,ii), A(b,c,ii), A(b,d,ii), A(b,e,ii), B(a,c,ii), B(a,d,ii), B(a,e,ii), B(b,c,ii), B(b,d,ii), B(b,e,ii), C(a,c,ii), C(a,d,ii), C(a,e,ii), C(b,c,ii), C(b,d,ii), C(b,e,ii), D(a,c,ii), D(a,d,ii), D(a,e,ii), D(b,c,ii), D(b,d,ii) and D(b,e,i), and groups contained therein, in another group of compounds $R^b$ is nitro, methylthio or methylsulfonyl.

Embodiment F

In another embodiment, within the compound of Formula (I) as defined above and embodiments (A), (B), (C), (D), and/or (E) and groups contained therein, in one group of compounds:

EWG is —N(R'$_3$)$^+$, —SO$_3$H, —SO$_3$R', —S(O$_2$)R', —S(O)R', —C(O)NH$_2$, —C(O)NHR$^g$, —C(O)NR$^f$R$^g$, —S(O$_2$)NH$_2$, —SO$_2$NHR$^i$, —SO$_2$NR$^h$R$^i$, —PO(OR')$_2$, —PO$_3$H$_2$, —PO(NR'$_2$)$_2$, —C≡N, —CH(haloalkyl), —C(O)X', —COOH, —COOR', —C(O)R', —C(O)H, —P(O)(OR')OR", halo, heteroaryl, or aryl wherein X' is independently halogen (e.g. chloro of fluoro), and R', R", R$^f$, R$^g$, R$^h$, and R$^i$ are independently hydrogen, alkyl, substituted alkyl, cycloalkyl, cycloalkyleneNR$^d$R$^e$ (where R$^d$ and R$^e$ are independently hydrogen, alkyl, or cycloalkyl) or R$^f$ and R$^g$ and R$^h$ and R$^i$ together with the nitrogen atom to which they are attached form heterocycloamino; and heterocycloamino, aryl and heteroaryl are substituted with one, two or three substituents independently selected from hydrogen, alkyl, alkoxy, hydroxyl, cyano, nitro, halo, haloalkyl, haloalkoxy, alkylthio, alkylsulfonyl, carboxy, alkoxycarbonyl, aminocarbonyl or aminosulfonyl.

Preferably, EWG is —CO—NR$^f$R$^g$ or —SO$_2$NR$^h$R$^i$ (wherein R$^f$ and R$^h$ are independently hydrogen, alkyl, or cycloalkyl and R$^g$ and R$^i$ are independently hydrogen, alkyl, substituted alkyl, cycloalkyleneNR$^d$R$^e$ (where R$^d$ and R$^e$ are independently hydrogen, alkyl, or cycloalkyl; or R$^d$ and R$^e$ together with the nitrogen atom to which they are attached form heterocycloamino), or R$^f$ and R$^g$ and R$^h$ and R$^i$ together with the nitrogen atom to which they are attached form heterocycloamino) and aryl or heteroaryl wherein each of the aforementioned ring is substituted with one, two or three substituents independently selected from hydrogen, alkyl, alkoxy, hydroxyl, cyano, nitro, halo, haloalkyl, haloalkoxy, alkylthio, alkylsulfonyl, carboxy, alkoxycarbonyl, aminocarbonyl or aminosulfonyl. Preferably, the heteroaryl ring is pyridinyl, pyrazolyl, indazolyl, indolyl, thienyl, pyrrolyl, imidazolyl, thiazolyl, benzothiazolyl, oxazolyl, benzimidazolyl, benzoxazolyl, isoxazolyl, benzisoxazolyl, triazolyl, benzotriazolyl, quinolinyl, isoquinolinyl, quinazolinyl, or pyrimidinyl each substituted as defined above.

Within the groups in embodiment F, in one group of compounds EWG is pyridine-2-yl, pyridine-3-yl, pyridine-4-yl, pyrrol-1-yl, pyrazol-1-yl, or thiazol-2-yl.

Within the groups in embodiment F, in another group of compounds EWG is dimethylaminocarbonyl, methylaminocarbonyl, isopropylaminocarbonyl, tert-butylaminocarbonyl, or 3-hydroxy-1-methylpropylaminocarbonyl.

Within the groups in embodiment F, in yet another group of compounds EWG is azetidin-1-ylcarbonyl, 4-hydroxyazetidin-1-ylcarbonyl, pyrrolidin-1-ylcarbonyl, 4-ethylpiperazin-1-ylcarbonyl, or 2,6-dimethylmorpholine-4-ylcarbonyl.

Preferably, EWG is —CON(CH$_3$)$_2$, —CONHcyclopropyl, or

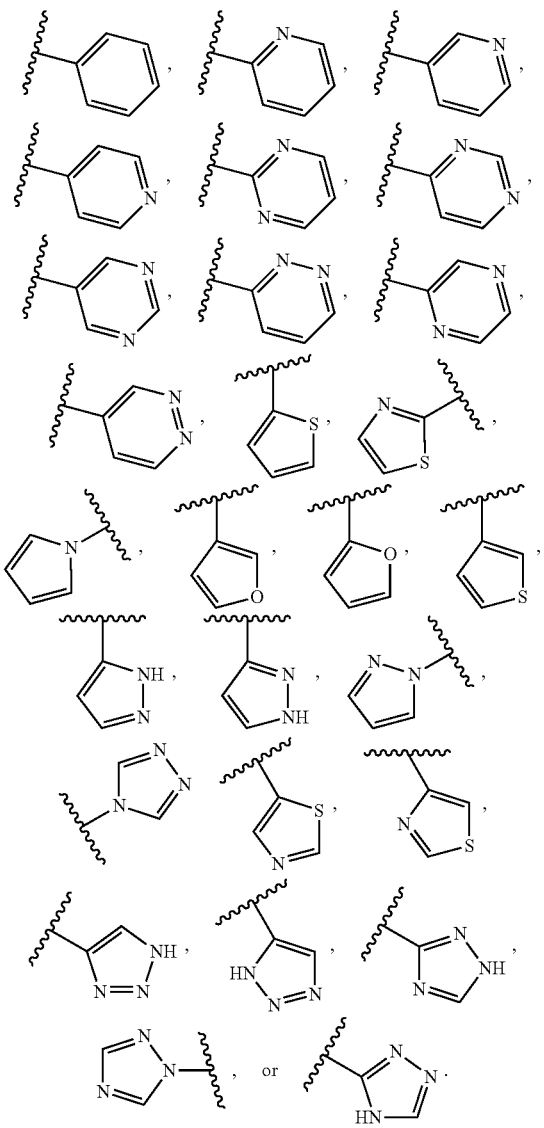

where A is heterocycloamino (such as piperazinyl or piperidinyl) optionally substituted with hydroxyl, methyl, methoxy, amino, methylamino or dimethylamino, preferably A is substituted at the 3 or 4 position of the piperidinyl and piperazinyl rings.

Preferably, EWG is aryl or heteroaryl ring heteroaryl wherein each of the aforementioned ring is substituted with one, two or three substituents independently selected from hydrogen, alkyl, alkoxy, hydroxyl, cyano, nitro, halo, haloalkyl, haloalkoxy, alkylthio, alkylsulfonyl, carboxy, alkoxycarbonyl, aminocarbonyl or aminosulfonyl.

Preferably, EWG is selected from:

and is substituted with one, two or three substituents independently selected from hydrogen, halo, haloalkyl, cyano, haloalkoxy, or alkylsulfonyl, preferably hydrogen, fluoro, cyano, trifluoromethyl, trifluoromethoxy, or cyano.

Embodiment G

In another embodiment, within the compound of Formula (I) as defined above and embodiments (A), (B), (C), (D), and/or (E) and groups contained therein, in one group of compounds:

EWG is:

(i) —C(O)NR$^f$R$^g$ where R$^f$ is hydrogen or alkyl and R$^g$ s substituted alkyl, preferably R$^g$ is (C$_2$-C$_6$)alkylene substituted with hydroxyl, alkoxy, alkylamino, dialkylamino or heterocycloamino or R$^f$ and R$^g$ together with the nitrogen atom to which they are attached form heterocycloamino. Preferably, R$^g$ is 2-hydroxyethyl, 2-methoxyethyl, 2-methylaminoethyl, or 2-dimethylaminoethyl; or R$^f$ and R$^g$ together with the nitrogen atom to which they are attached form pyrrolidinyl, piperidinyl, piperazinyl, or morpholinyl ring wherein the pyrrolidinyl, piperidinyl, and piperazinyl rings are optionally substituted with hydroxyl, methyl, methoxy, amino, methylamino or dimethylamino, preferably at the 3 or 4 position of the pyrrolidinyl, piperidinyl, and piperazinyl rings; or (ii) —COOR' where R is hydrogen or alkyl, preferably methyl, ethyl, isopropyl, or tert-butyl; or (iii) —SO$_2$alkyl, —SO$_2$NHalkyl, —SO$_2$N(alkyl)$_2$, —S(O)$_2$NR$^h$R$^i$ where R$^h$ and R$^i$ together with the nitrogen atom to which they are attached form heterocycloamino. Preferably EWG is methylsulfonyl, methylaminosulfonyl, dimethylaminosulfonyl or R$^h$ and R$^i$ together with the nitrogen atom to which they are attached form pyrrolidinyl, piperidinyl, piperazinyl, or morpholinyl ring wherein the pyrrolidinyl, piperidinyl, and piperazinyl rings are optionally substituted with hydroxyl, methyl, methoxy, amino, methylamino or dimethylamino, preferably the substituent is at the 3 or 4 position of the pyrrolidinyl, piperidinyl, and piperazinyl rings; or (iv) a 5 or six membered heteroaryl ring is substituted with one, two or three substituents independently selected from hydrogen, alkyl, alkoxy, hydroxyl, cyano, nitro, halo, haloalkyl, haloalkoxy, alkylthio, alkylsulfonyl, carboxy, alkoxycarbonyl, aminocarbonyl or aminosulfonyl. Preferably, the heteroaryl ring is selected from:

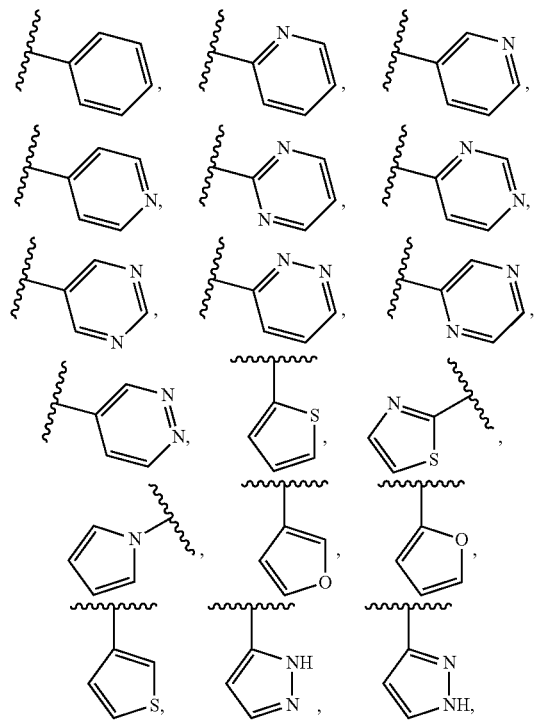

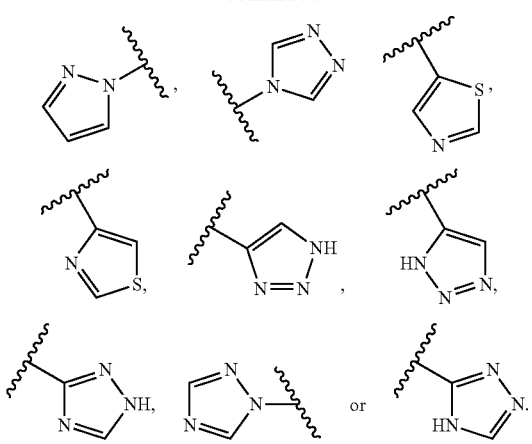

and is substituted with one, two or three substituents independently selected from hydrogen, halo, haloalkyl, cyano, haloalkoxy, or alkylsulfonyl, preferably hydrogen, fluoro, cyano, trifluoromethyl, trifluoromethoxy, or cyano.

(v) Preferably, EWG is —C(O)NR$^f$R$^g$ where R$^f$ is hydrogen or alkyl and R$^g$ is substituted alkyl, preferably R$^g$ is (C$_2$-C$_6$)alkylene substituted with hydroxyl, alkoxy, alkylamino, dialkylamino or heterocycloamino or R$^f$ and R$^g$ together with the nitrogen atom to which they are attached form heterocycloamino. Preferably, R$^g$ is 2-hydroxyethyl, 2-methoxyethyl, 2-methylaminoethyl, or 2-dimethylaminoethyl; or R$^f$ and R$^g$ together with the nitrogen atom to which they are attached form pyrrolidinyl, piperidinyl, piperazinyl, or morpholinyl ring wherein the pyrrolidinyl, piperidinyl, and piperazinyl rings are optionally substituted with hydroxyl, methyl, methoxy, amino, methylamino or dimethylamino, preferably at the 3 or 4 position of the pyrrolidinyl, piperidinyl, and piperazinyl rings.

(vi) Preferably, EWG is a 5 or six membered heteroaryl ring is substituted with one, two or three substituents independently selected from hydrogen, alkyl, alkoxy, hydroxyl, cyano, nitro, halo, haloalkyl, haloalkoxy, alkylthio, alkylsulfonyl, carboxy, alkoxycarbonyl, aminocarbonyl or aminosulfonyl. Preferably, the heteroaryl ring is selected from:

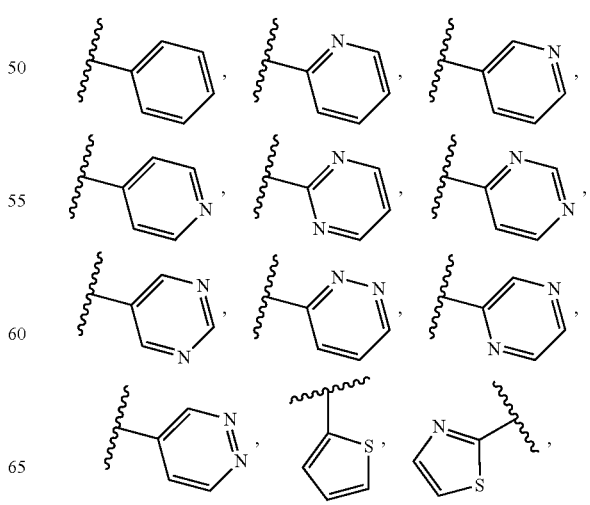

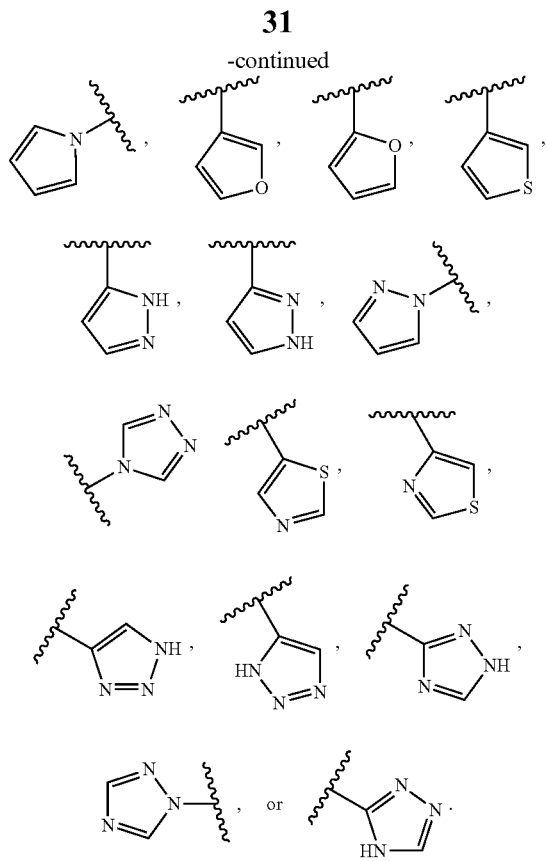

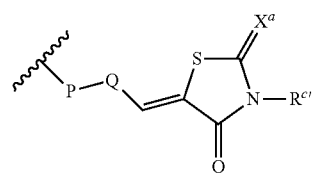

where $X^a$ is O, S, or N(H or alkyl) and $R^{c'}$ is hydrogen, alkyl, cycloalkyl, substituted alkyl or cycloalkyleneNR$^d$R$^e$ and L is O. Preferably, $X^a$ is O, and $R^{c'}$ is hydrogen, methyl, ethyl, propyl, cyclopropyl, or alkylene substituted with hydroxyl, alkoxy, alkylamino or dialkylamino. Preferably, $X^a$ is O, and $R^{c'}$ is hydrogen, methyl, ethyl, propyl, cyclopropyl, 2-hydroxyethyl, 2-methoxyethyl, 2-methylaminoethyl or 2-dimethylaminoethyl.

(b) In another group of compounds $R^1$ is hydrogen, alkyl, alkoxy, halo, haloalkyl, haloalkoxy, or cyano. Preferably, $R^1$ is hydrogen, methyl, methoxy, fluoro, chloro, trifluoromethyl, trifluoromethoxy, or cyano; and $R^5$ a group of formula (a)

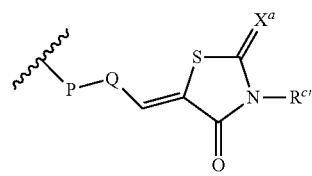

where $X^a$ is O, S, or N(H or alkyl) and $R^{c'}$ is hydrogen, alkyl, cycloalkyl, substituted alkylalkyl or cycloalkyleneNR$^h$R; and L is NHCONH, NHCO, or CONH. Preferably, $X^a$ is O, and $R^{c'}$ is hydrogen, methyl, ethyl, propyl, cyclopropyl, or alkylene substituted with hydroxyl, alkoxy, alkylamino or dialkylamino. Preferably, $X^a$ is O, and $R^{c'}$ is hydrogen, methyl, ethyl, propyl, cyclopropyl, 2-hydroxyethyl, 2-methoxyethyl, 2-methylaminoethyl or 2-dimethylaminoethyl.

Within embodiment (H) and groups contained therein, in one group of compounds —P-Q- are as described in embodiment (E) above, and groups contained therein i.e., (c), (d), (e), (i) and (ii) above or combinations thereof. Preferably, —P-Q- together is alkylene, heteroalkylene, aryl or heteroaryl, more preferably phenyl or heteroaryl wherein phenyl or heteroaryl is substituted as defined herein.

Within embodiment (H) and groups contained therein, in one group of compounds —P-Q- is a bond.

Within embodiment (H) and groups contained therein, in another group of compounds P is alkylene, preferably methylene and Q is a bond.

Embodiment I

In another embodiment, within the compound of Formula (I) as defined above and embodiments (A), (B), (C) and/or (D) and groups contained therein:

(a) in one group of compounds:

$R^1$ is hydrogen, alkyl, hydroxy, alkoxy, halo, haloalkyl, or haloalkoxy and $R^5$ is —Z-(EWG')-C($R^{b'}$)=CHR$^c$ where Z is bond, NR$^a$ (where R$^a$ is hydrogen or alkyl), —O—, S, SO, SO$_2$, alkylene, heteroalkylene, aryl or heteroaryl, EWG' is an electron withdrawing group, $R^{b'}$ is nitro, halo, haloalkoxy, alkylthio, or alkylsulfonyl and $R^c$ is alkyl, substituted alkyl, cycloalkyl, cycloalkyleneNR$^d$R$^e$ where $R^d$ and $R^e$ are independently hydrogen, alkyl, or cycloalkyl; and L is NHCONH, NHCO, or CONH.

and is substituted with one, two or three substituents independently selected from hydrogen, halo, haloalkyl, cyano, haloalkoxy, or alkylsulfonyl, preferably hydrogen, fluoro, cyano, trifluoromethyl, trifluoromethoxy, or cyano.

(vii) Preferably, EWG is —COOR' where R is hydrogen or alkyl, preferably methyl, ethyl, isopropyl, or tert-butyl; or —SO$_2$alkyl, —SO$_2$NHalkyl, —SO$_2$N(alkyl)$_2$, or —S(O)$_2$NR$^h$R$^i$ where $R^h$ and $R^i$ together with the nitrogen atom to which they are attached form heterocycloamino.

(viii) Preferably, EWG is methylsulfonyl, methylaminosulfonyl, dimethylaminosulfonyl or —S(O)$_2$NR$^h$R$^i$ where $R^h$ and $R^i$ together with the nitrogen atom to which they are attached form pyrrolidinyl, piperidinyl, piperazinyl, or morpholinyl ring wherein the pyrrolidinyl, piperidinyl, and piperazinyl rings are optionally substituted with hydroxyl, methyl, methoxy, amino, methylamino or dimethylamino, preferably the substituent is at the 3 or 4 position of the pyrrolidinyl, piperidinyl, and piperazinyl rings, Within embodiment (G) and groups contained therein i.e., (i)-(vii), in one group of compounds —P-Q- are as described in embodiment (E) above, and groups contained therein i.e., (c), (d), (e), (f), (i) and (ii) above or combinations thereof.

Embodiment H

In another embodiment, within the compound of Formula (I) as defined above and embodiments (A), (B), (C), and/or (D), and groups contained therein, in one group of compounds:

(a) $R^5$ is hydrogen, alkyl, alkoxy, halo, haloalkyl, haloalkoxy, or cyano. Preferably, $R^5$ is hydrogen, methyl, methoxy, fluoro, chloro, trifluoromethyl, trifluoromethoxy, or cyano; $R^1$ group of formula (a)

(b) In another group of compounds:

R⁵ is hydrogen, alkyl, hydroxy, alkoxy, halo, haloalkyl, or haloalkoxy and $R^1$ is —Z-(EWG')-C($R^{b'}$)=CHR$^c$ where Z is bond, NR$^a$ (where R$^a$ is hydrogen or alkyl), —O—, S, SO, SO₂, alkylene, aryl, heteroaryl, or heteroalkylene, EWG' is an electron withdrawing group, $R^{b'}$ is nitro, halo, haloalkyl, haloalkoxy, alkylthio, or alkylsulfonyl and R$^c$ is alkyl, substituted alkyl, cycloalkyl, cycloalkyleneNR$^d$R$^e$ where R$^d$ and R$^e$ are independently hydrogen, alkyl, or cycloalkyl and L is O.

(i) Within groups (a) and (b), in one group of compounds Z is bond, cycloalkylene, phenyl, heteroaryl, or alkylene and EWG' is —NR'CO— or —NR'SO₂—; wherein each R' is independently hydrogen or alkyl; $R^{b'}$ is nitro, fluoro, trifluoromethyl, 2,2,2-trifluoroethyl, trifluoromethoxy, 2,2,2-trifluoroethyloxy, methylsulfonyl or methylthio, preferably trifluoromethyl and R$^c$ is methyl, isopropyl, tert-butyl, cyclopropyl, trifluoromethyl, 2,2,2-trifluoroethyl, 1-methyl-1-methylaminoethyl, 1-methyl-1-dimethylaminoethyl, 1-methyl-1-aminoethyl, 1-methylaminocycloprop-1-ylene, or 1-dimethylaminocycloprop-1-ylene. Within groups in (i) in one group of compounds EWG' is —NHCO— and Z is

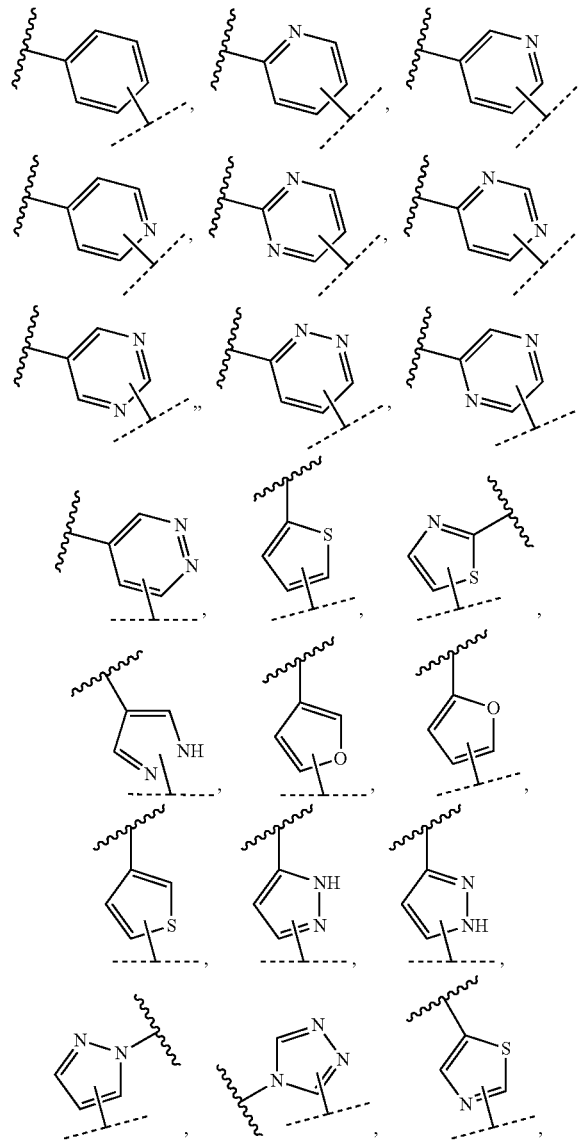

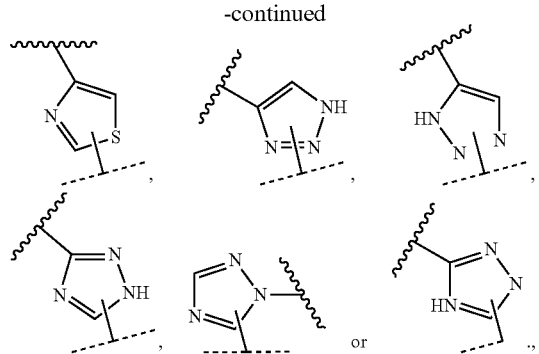

preferably phenyl. Preferably, —NHCO— is attached at the meta or para, preferably at meta position of phenyl ring the carbon atom attaching phenyl to Z to the rest of the molecule being carbon-1.

(ia) In one group of compounds, R⁵ is —C($R^{b'}$)=CHR$^c$ when in (I)(a) Ar is electron withdrawing; e.g. Ar is pyridinyl and —C($R^{b'}$)=CHR$^c$ is attached at carbon ortho to the N atom on the pyridinyl ring; $R^{b'}$ is nitro, fluoro, trifluoromethyl, 2,2,2-trifluoroethyl, trifluoromethoxy, 2,2,2-trifluoroethyloxy, methylsulfonyl or methylthio, preferably trifluoromethyl and R$^c$ is methyl, isopropyl, tert-butyl, cyclopropyl, trifluoromethyl, 2,2,2-trifluoroethyl, 1-methyl-1-methylaminoethyl, 1-methyl-1-dimethylaminoethyl, 1-methyl-1-aminoethyl, 1-methylaminocycloprop-1-ylene, or 1-dimethylaminocycloprop-1-ylene.

(ii) Within compounds groups (a) and (b), in one group of compounds Z is bond, NR$^a$, O or alkylene, preferably a bond or methylene, and EWG' is

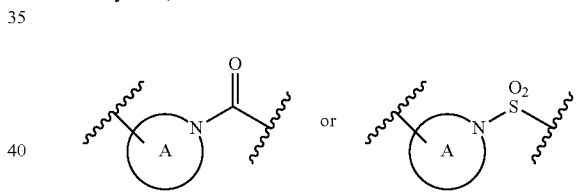

where ring A is heterocycloamino, preferably pyrrolidin-yl or piperidinyl, $R^{b'}$ is nitro, fluoro, trifluoromethyl, 2,2,2-trifluoroethyl, trifluoromethoxy, 2,2,2-trifluoroethyloxy, methylsulfonyl or methylthio, preferably trifluoromethyl and R$^c$ is methyl, isopropyl, tert-butyl, cyclopropyl, trifluoromethyl, 2,2,2-trifluoroethyl, 1-methyl-1-methylaminoethyl, 1-methyl-1-dimethylaminoethyl, 1-methyl-1-aminoethyl, 1-methylaminocycloprop-1-ylene, or 1-dimethylaminocycloprop-1-ylene. Preferably Z-EWG' is 3-piperidin-1-ylcarbonyl or —CH₂-2-pyrrolidin-1-ylcarbonyl (i.e., methylene is attached at 2-position of pyrrolidin-1-ylcarbonyl ring), $R^{b'}$ is nitro, fluoro, trifluoromethyl, 2,2,2-trifluoroethyl, trifluoromethoxy, 2,2,2-trifluoroethyloxy, methylsulfonyl or methylthio, preferably trifluoromethyl and R$^c$ is methyl, isopropyl, tert-butyl, cyclopropyl, trifluoromethyl, 2,2,2-trifluoroethyl, 1-methyl-1-methylaminoethyl, 1-methyl-1-dimethylaminoethyl, 1-methyl-1-aminoethyl, 1-methylaminocycloprop-1-ylene, or 1-dimethylaminocycloprop-1-ylene (iii) Within groups (a) and (b), in one group of compounds Z is bond, NR$^a$, O or alkylene and EWG' is heteroaryl, or aryl; wherein R$^a$ is independently hydrogen or alkyl; and aryl and heteroaryl are substituted with one, two or three substituents independently selected from hydrogen, alkyl, alkoxy, hydroxyl, cyano, nitro, halo, haloalkyl, haloalkoxy, alkylthio, alkylsulfonyl, carboxy, alkoxycarbonyl, aminocarbonyl or aminosulfonyl. Preferably, the aryl and heteroaryl rings are selected from:

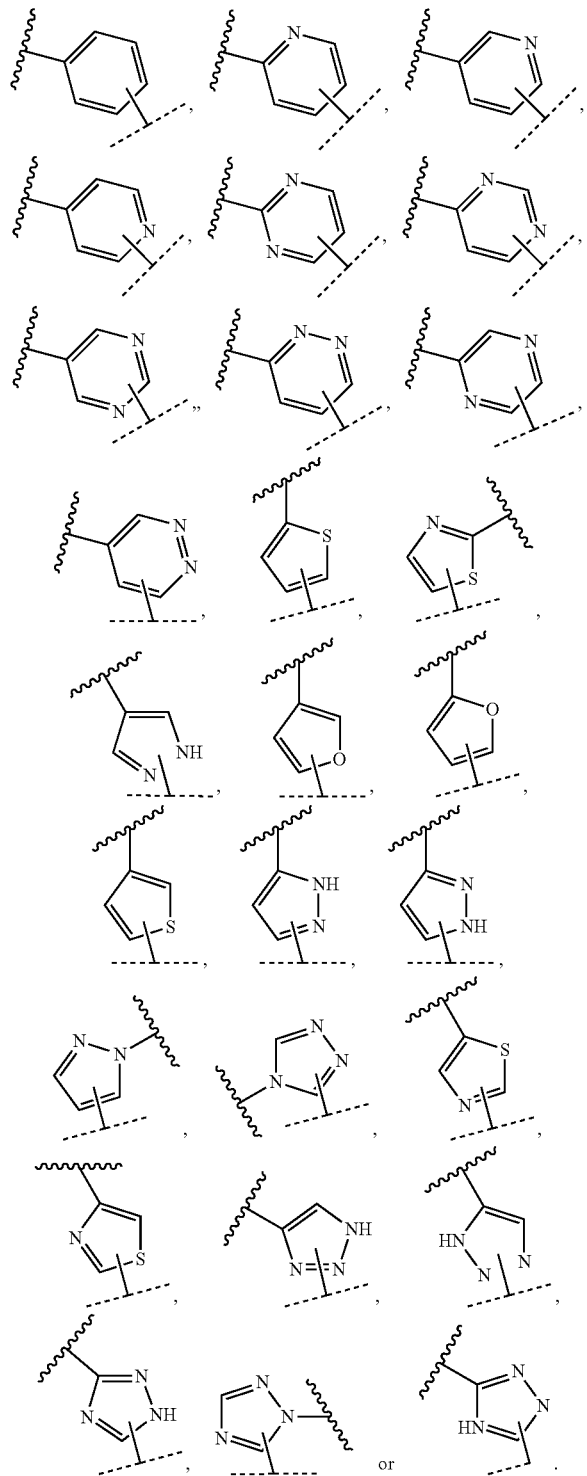

$R^{b'}$ is nitro, fluoro, trifluoromethyl, 2,2,2-trifluoroethyl, trifluoromethoxy, 2,2,2-trifluoroethyloxy, methylsulfonyl or methylthio, preferably trifluoromethyl and $R^c$ is methyl, isopropyl, tert-butyl, cyclopropyl, trifluoromethyl, 2,2,2-trifluoroethyl, 1-methyl-1-methylaminoethyl, 1-methyl-1-dim- ethylaminoethyl, 1-methyl-1-aminoethyl, 1-methylaminocycloprop-1-ylene, or 1-dimethylaminocycloprop-1-ylene.

Embodiment J

In another embodiment, within the compound of Formula (I) as defined above and embodiments (A), (B), (C) and/or (D) and groups contained therein:

(a) in one group of compounds:

$R^1$ is hydrogen, alkyl, hydroxy, alkoxy, halo, haloalkyl, or haloalkoxy and $R^5$ is a group of formula (b) and L is NHCONH, NHCO, or CONH.

(b) In another group of compounds:

$R^5$ is hydrogen, alkyl, hydroxy, alkoxy, halo, haloalkyl, or haloalkoxy and $R^1$ is a group of formula (b) and L is O.

Within groups (a) and (b) in embodiment (I), preferably, $X^a$ is O, and $R^{c'}$ is ethyl, propyl, cyclopropyl, or alkylene substituted with hydroxyl, alkoxy, alkylamino or dialkylamino. Preferably, $X^a$ is O, and $R^c$ is methyl, isopropyl, tert-butyl, cyclopropyl, trifluoromethyl, 2,2,2-trifluoroethyl, 1-methyl-1-methylaminoethyl, 1-methyl-1-dimethylaminoethyl, 1-methyl-1-aminoethyl, 1-methylaminocycloprop-1-ylene, or 1-dimethylaminocycloprop-1-ylene. Within embodiment (I) and groups contained therein, in one group of compounds —P-Q- are as described in embodiment (E) above, and groups contained therein i.e., (c), (d), (e), (i) and (ii) above or combinations thereof. Preferably, P is alkylene, preferably methylene and Q is a bond.

Embodiment K

In another embodiment, within the compound of Formula (I) as defined above and embodiments (A), (B), (C), (D), (E), (F), (G), (H) and/or (I) and groups contained therein, in one group of compounds the

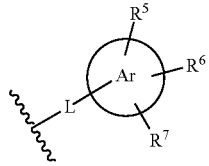

group is attached at the 4-position of the phenyl ring, the carbon atom of the phenyl ring attached to

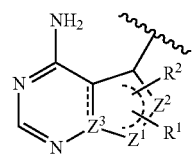

being carbon 1.

(i) Within the groups in embodiment K, in one group of compounds, Ar is phenyl.

(ii) Within groups in embodiment K, in another group of compounds when $R^5$ is not hydrogen, alkyl, alkoxy, halo, haloalkyl, haloalkoxy, or cyano, then, Ar is phenyl substituted at meta or para, preferably meta position with $R^5$, and $R^6$ is ortho or para to $R^5$.

(ii) Within groups in embodiment K, in another group of compounds when $R^5$ is not hydrogen, alkyl, alkoxy, halo, haloalkyl, haloalkoxy, or cyano, then, Ar is heteroaryl, preferably pyridyl substituted with $R^5$, and $R^6$ is ortho or para to $R^5$.

(iii) Within groups in embodiment K, in another group of compounds when $R^1$ is not hydrogen, alkyl, alkoxy, halo, haloalkyl, haloalkoxy, or cyano, then, Ar is phenyl substituted at meta and/or para with $R^5$ or $R^6$ which are preferably chloro or trifluoromethyl.

(iv) Within groups in embodiment K, in another group of compounds when $R^1$ is not hydrogen, alkyl, alkoxy, halo, haloalkyl, haloalkoxy, or cyano, Ar is heteroaryl, preferably pyridyl or pyrimidinyl optionally substituted with $R^5$-$R^7$.

Embodiment L

In yet another embodiment, the compound of Formula (I) has the structure (Ia) or (Ib) shown below:

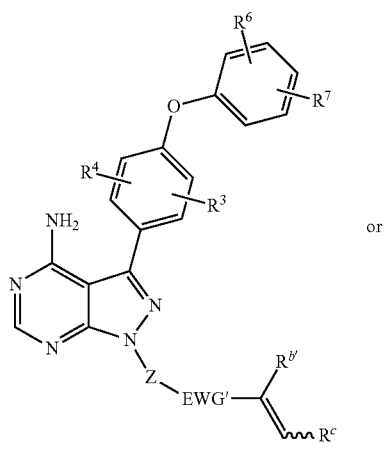

(Ia)

or

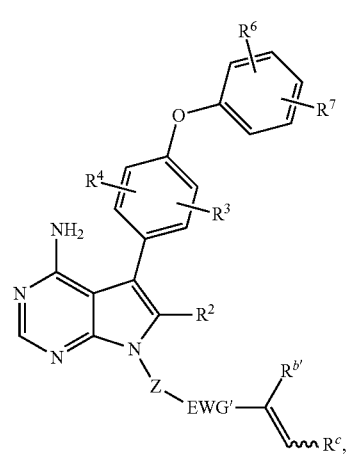

(Ib)

wherein:

$R^{b'}$ is fluoro or haloalkyl; preferably fluoro or trifluoromethyl;

$R^2$ is hydrogen or alkyl;

$R^3$ and $R^4$ are independently hydrogen, alkyl, haloalkyl, fluoro or chloro;

$R^6$ and $R^7$ are independently hydrogen or fluoro;

Z is a bond or alkylene;

EWG' is —NR'CO—, —NR'SO$_2$—,

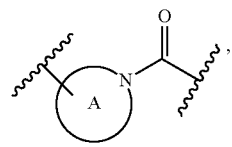

or a five membered heteroaryl ring where R' is hydrogen or alkyl and ring A is 2-pyrrolidinyl or 3-piperidinyl, each ring optionally substituted with one or two alkyl provided that (i) when Z is a bond then EWG' is 3-piperidinylcarbonyl optionally substituted with one or two alkyl and (iii) when Z is alkylene, then ring A is not 3-piperidinylcarbonyl optionally substituted with one or two alkyl; and $R^c$ is cycloalkyl, alkyl, or substituted alkyl.

(note: for the groups in the definition of EWG', left side of the group is attached to Z and right side is attached to —C($R^{b'}$)=$R^c$ e.g., in —NR'CO—, NR' is attached to Z and CO is attached to —C($R^{b'}$)=$R^c$).

(i) Within embodiment L in one group of compounds, the compound of Formula (I) has structure (Ia).

(ii) Within embodiment I, in another group of compounds the compound of Formula (I) has structure (Ib).

(a) Within the embodiment (L) and groups contained therein i.e., (i) and (ii), in one group of compounds:

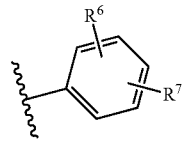

is a ring of formula:

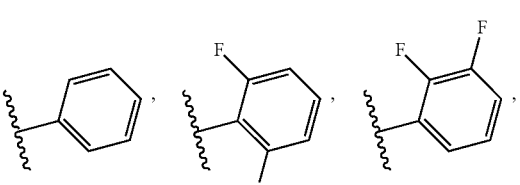

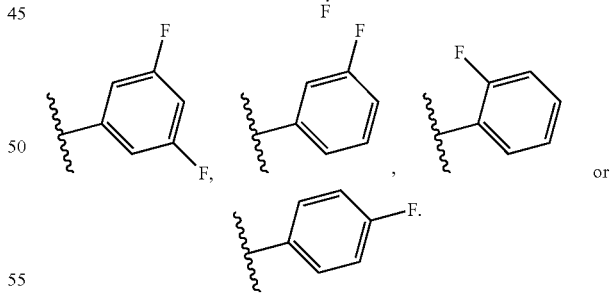

Preferably,

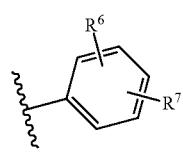

is a ring of formula:

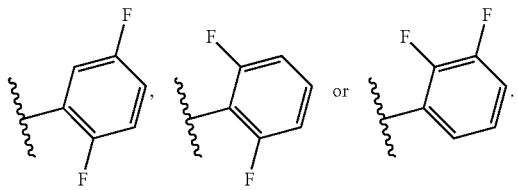

(b) Within embodiment (L) and groups contained therein, and subpart (a) of Embodiment (L) and groups contained therein, in one group of compounds:

$R^2$ is hydrogen or alkyl, preferably hydrogen or methyl, more preferably hydrogen;

$R^3$ and $R^4$ are independently hydrogen, methyl, ethyl, trifluoromethyl, fluoro or chloro. Preferably, within groups in (b), in one group of compounds

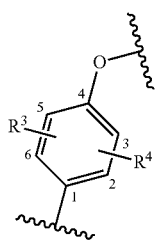

is a ring of formula:

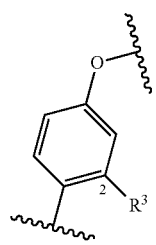

where $R^3$ is hydrogen, methyl, ethyl, chloro, fluoro or trifluoromethyl, preferably hydrogen, methyl, ethyl, chloro or fluoro, more preferably, methyl, ethyl, or chloro, even more preferably hydrogen, chloro or fluoro, particularly preferably hydrogen or fluoro. Preferably, within groups in (b), in another group of compounds

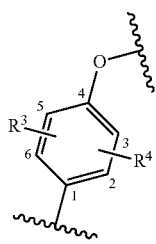

is a ring of formula

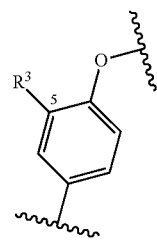

where $R^3$ is alkyl or halo, preferably methyl, chloro or fluoro. Preferably, within groups in (b), in yet another group of compounds

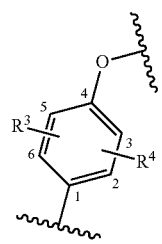

is a ring of formula

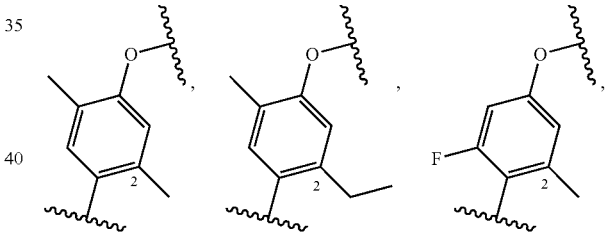

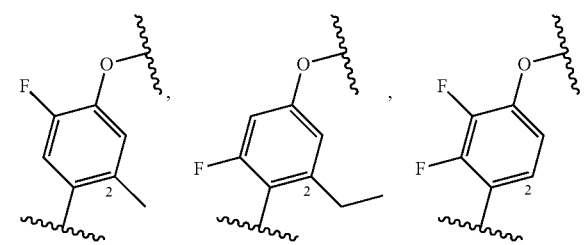

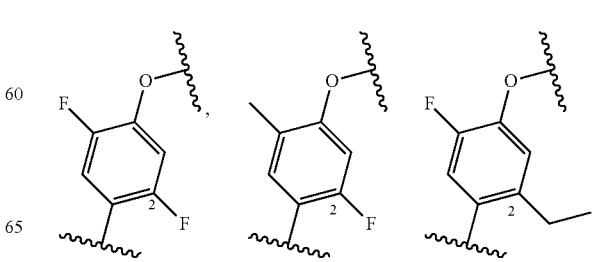

-continued

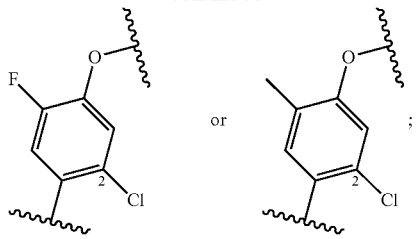

preferably,

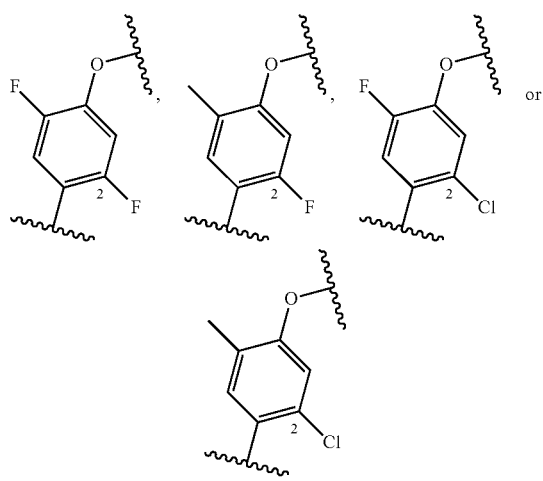

(c) Within embodiment (L) and groups contained therein, and subpart (a) and/or (b) of Embodiment (L) and groups contained therein, in one group of compounds:

Z is a alkylene;

EWG' is —NR'CO— or —NR'SO$_2$— where R' is hydrogen or alkyl, preferably hydrogen or methyl. Preferably, within groups in (c), in one group of compounds is —Z-EWG'- is -(alkylene)-NR'CO— or -(alkylene)-NR'SO$_2$— wherein Z is ethylene, —C(CH$_3$)$_2$—CH$_2$—, or —CH$_2$—C(CH$_3$)$_2$— and EWG' is —NHCO—, —N(CH$_3$)CO—, —NHSO$_2$—, or —N(CH$_3$)SO$_2$—, more preferably Z is ethylene, —C(CH$_3$)$_2$—CH$_2$—, or —CH$_2$—C(CH$_3$)$_2$— and EWG' is —NHCO—, —N(CH$_3$)CO—, —NHSO$_2$—, or —N(CH$_3$)SO$_2$—, even more preferably, EWG' is —NHCO—.

(d) Within embodiment (L) and groups contained therein, and subpart (a) and/or (b) of Embodiment (L) and groups contained therein, in another group of compounds:

Z is a bond or alkylene; and

EWG' is

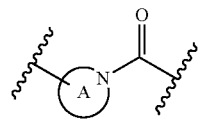

ring A is pyrrolinyl or piperidinyl, each ring optionally substituted with one or two alkyl, preferably methyl. Within the groups in subpart (d), in one group of compounds —Z-EWG'- is 3(R)-piperidin-1-carbonyl. Within the groups in subpart (d), in another group of compounds —Z-EWG'- is 2-CH$_2$-pyrrolidin-1-ylcarbonyl, 2-CH(CH$_3$)-pyrrolidin-1-ylcarbonyl; 2-CH$_2$-3,3-dimethylpyrrolidin-1-ylcarbonyl or 2-CH$_2$-4,4-dimethylpyrrolidin-1-ylcarbonyl the carbon atom of the pyrrolidinyl ring attached to —CH$_2$— having (R) stereochemistry.

(e) Within embodiment (L) and groups contained therein, and subpart (a) and/or (b) of Embodiment (L) and groups contained therein, in another group of compounds:

Z is alkylene; and

EWG' is a five membered heteroaryl ring, preferably Z is methylene, ethylene, —C(CH$_3$)$_2$CH$_2$—, —CH$_2$—C(CH$_3$)$_2$— and Z is oxazolyl, more preferably —Z-EWG'- is 2-C(R$^{b'}$)=CR$^c$-oxazol-5-yl.

(f) Within embodiment (L) and groups contained therein, and subpart (a) and/or (b) and/or (c) and/or (d) and/or (e) and groups contained therein, in one group of compounds R$^c$ is cycloalkyl, alkyl, or substituted alkyl, preferably, isopropyl, tert-butyl or 1-dimethylamino-1-methylethyl, more preferably cyclopropyl.

(g) Within embodiment (L) and groups contained therein, and subpart (a) and/or (b) and/or (c) and/or (d) and/or (e) and groups contained therein, in one group of compounds R$^c$ is cycloalkyl, preferably cyclopropyl.

(h) Within embodiment (L) and groups contained therein, and subpart (a) and/or (b) and/or (c) and/or (d) and/or (e) and groups contained therein, in one group of compounds R$^c$ is alkyl, preferably isopropyl or tert-butyl, more preferably isopropyl.

(i) Within embodiment (L) and groups contained therein, and subpart (a) and/or (b) and/or (c) and/or (d) and/or (e) and groups contained therein, in one group of compounds R$^c$ is substituted alkyl, preferably, alkyl substituted with alkoxy or NRR' (where R is hydrogen, alkyl, alkoxyalkyl or cycloalkyl and R' is hydrogen or alkyl), or heterocyclcyl which is optionally substituted with one or two groups independently selected from alkyl), preferably R$^c$ is —C(CH$_3$)$_2$NH$_2$, —C(CH$_3$)$_2$NHCH$_3$, —C(CH$_3$)$_2$N(CH$_3$)$_2$, —C(CH$_3$)$_2$NHCH$_2$CH$_3$, —C(CH$_3$)$_2$NHCH(CH$_3$)$_2$, —C(CH$_3$)$_2$NHcyclopropyl, —C(CH$_3$)$_2$NH(CH$_2$)$_2$OCH$_3$, —C(CH$_3$)$_2$OCH$_2$CH$_3$, —C(CH$_3$)$_2$morpholine-4-yl. Within groups in (i), in one group of compounds R$^c$ is —C(CH$_3$)$_2$NH$_2$, —C(CH$_3$)$_2$NHCH, —C(CH$_3$)$_2$N(CH$_3$)$_2$, —C(CH$_3$)$_2$NHCH$_2$CH$_3$, —C(CH$_3$)$_2$NHCH(CH$_3$)$_2$ or —C(CH$_3$)$_2$NH(CH$_2$)$_2$OCH$_3$. Within groups in (i), in another group of compounds R$^c$ is —C(CH$_3$)$_2$NHcyclopropyl. Within groups in (i), in yet another group of compounds R$^c$ is —C(CH$_3$)$_2$OCH$_2$CH$_3$. Within groups in (i), in yet another group of compounds R$^c$ is —C(CH$_3$)$_2$morpholine-4-yl. Within groups in (i), in yet another group of compounds R$^c$ is —C(CH$_3$)$_2$NH$_2$.

(j) Within embodiment (L) and groups contained therein, and subpart (a) and/or (b) and/or (c) and/or (d) and/or (e) and groups contained therein, in one group of compounds R$^c$ is cycloalkyleneNR$^d$R$^e$ (where R$^d$ and R$^e$ are independently hydrogen, or alkyl), preferably

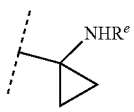

where R$^e$ is hydrogen, methyl, ethyl or isopropyl.

Embodiment M:

In another embodiment, the disclosure includes compounds of embodiments 1-20 below:

1. A compound of Formula (I):

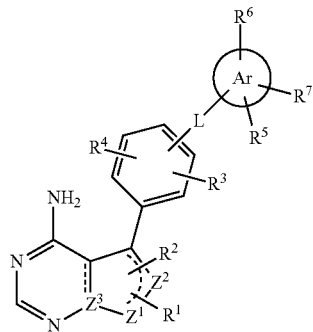

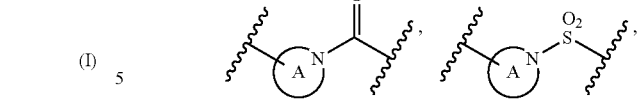

wherein:
dashed lines are independently an optional bond;

$Z^1$, $Z^2$, and $Z^3$ are —N— or CH, provide that at least one and not more than two of $Z^1$, $Z^2$, and $Z^3$ are simultaneously N;

L is O, CO, CH$_2$, S, SO, SO$_2$, NR, NRCO, CONR, NR'SO$_2$, SO$_2$NR', or NRCONR', where (each R and R' is independently hydrogen or alkyl, cycloalkyl);

Ar is aryl, heteroaryl, cycloalkyl or heterocyclyl;

one of $R^1$ and $R^5$ is hydrogen, alkyl, hydroxy, alkoxy, halo, haloalkyl, or haloalkoxy and the other of $R^1$ and $R^5$ is:

(i) —P-Q-CH=C($R^b$)(EWG) where P is a bond, NR$^a$ (where R$^a$ is hydrogen or alkyl), —O—, S, SO, SO$_2$, alkylene or heteroalkylene, Q is a bond, aryl or heteroaryl aryl wherein aryl or heteroaryl is optionally substituted with one or two substituents independently selected from hydrogen, halo, alkyl, alkoxy, alkylthio, haloalkyl, or haloalkoxy, R$^b$ is cyano, nitro, halo, haloalkyl, haloalkoxy, alkylthio, or alkylsulfonyl and EWG is —N(R'$_2$), —N(R'$_3$)$^+$, —SO$_3$H, —SO$_3$R', —S(O$_2$)R', —S(O)R', —C(O)NH$_2$, —C(O)NHR$^g$, —C(O)NR$^f$R$^g$, —S(O$_2$)NH$_2$, —SO$_2$NHR$^i$, SO$_2$NR$^h$R$^i$, —PO(OR')$_2$, —PO$_3$H$_2$, —PO(NR'$_2$)$_2$, —C≡N, —CH(haloalkyl), —C(O)X', —COOH, —COOR', —C(O)R', —C(O)H, —P(O)(OR')OR", halo, heteroaryl, or aryl; wherein X' is independently halogen (e.g. chloro or fluoro), R', R", R$^f$, R$^g$, R$^h$, and R$^i$ are independently hydrogen, alkyl, substituted alkyl, cycloalkyl, cycloalkyleneNR$^d$R$^e$ (where R$^d$ and R$^e$ are independently hydrogen, alkyl, or cycloalkyl) or R$^f$ and R$^g$ and R$^h$ and R$^i$ together with the nitrogen atom to which they are attached form heterocycloamino; and aryl and heteroaryl are substituted with one, two or three substituents independently selected from hydrogen, alkyl, alkoxy, hydroxyl, cyano, nitro, halo, haloalkyl, haloalkoxy, alkylthio, alkylsulfonyl, carboxy, alkoxycarbonyl, aminocarbonyl or aminosulfonyl; or (ii) —Z-(EWG')-C(R$^{b'}$)=CHR$^c$ where Z is bond, NR$^a$ (where R$^a$ is hydrogen or alkyl), —O—, S, SO, SO$_2$, alkylene, cycloalkylene, heteroalkylene, —(Z$^a$)$_{n1}$-aryl, or —(Z$^a$)$_{n1}$-heteroaryl (wherein n1 is 0 or 1, Z$^a$ is NR$^a$ (where R$^a$ is hydrogen or alkyl), —O—, S, SO, SO$_2$, alkylene, or heteroalkylene and aryl or heteroaryl is optionally substituted with one or two substituents independently selected from hydrogen, halo, alkyl, alkoxy, alkylthio, haloalkyl, or haloalkoxy), EWG' is a bond, —CH(haloalkyl), —NR'—, —S(O$_2$)—, —S(O)—, —CO—, —NR'CO—, —NR'SO$_2$—, —(OR')(O)P—, heteroaryl, or aryl; wherein each R' is independently hydrogen, alkyl, substituted alkyl, cycloalkyl; ring A is heterocycloamino where the carbonyl and sulfonyl groups are attached to —C(R$^{b'}$)=CHR$^c$; and heterocycloamino, aryl and heteroaryl are substituted with one, two or three substituents independently selected from hydrogen, alkyl, alkoxy, hydroxyl, cyano, nitro, halo, haloalkyl, haloalkoxy, alkylthio, alkylsulfonyl, carboxy, alkoxycarbonyl, aminocarbonyl or aminosulfonyl, R$^{b'}$ is nitro, halo, haloalkyl, haloalkoxy, alkylthio, or alkylsulfonyl and R$^c$ is alkyl, substituted alkyl, haloalkoxy, cycloalkyl, cycloalkyleneNR$^d$R$^e$ where R$^d$ and R$^e$ are independently hydrogen, alkyl, or cycloalkyl; or (iii) a group of formula (a) or (b);

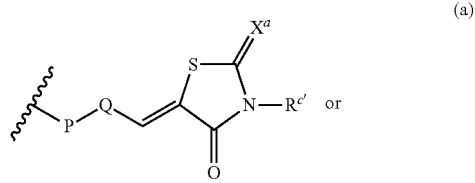

(a)

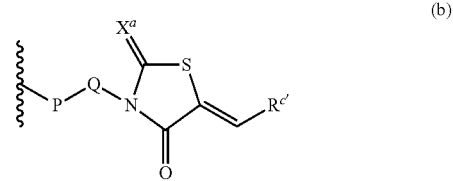

(b)

where P and Q are as defined above, X$^a$ is O, S, or N(H or alkyl) and R$^{c'}$ is hydrogen, alkyl, substituted alkyl, haloalkoxy, cycloalkyl, or cycloalkyleneNR$^d$R$^e$ where R$^d$ and R$^e$ are independently hydrogen, alkyl, or cycloalkyl;

$R^2$ is hydrogen, alkyl, hydroxy, alkoxy, cyano, halo or haloalkyl;

$R^3$ and $R^4$ are independently hydrogen, alkyl, cycloalkyl, hydroxy, alkoxy, cyano, halo, haloalkyl or haloalkoxy; and $R^6$ and $R^7$ are independently hydrogen, alkyl, hydroxy, alkoxy, halo, haloalkyl, haloalkoxy, carboxy, alkoxycarbonyl, cyano, —CONH$_2$, amino, monosubstituted and disubstituted amino;

or a pharmaceutically acceptable salt thereof; provided that the compound of Formula (I) is not:

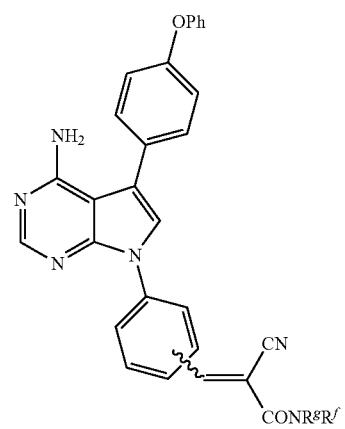

where $R^g$ is hydrogen or alkyl and $R^f$ is hydrogen, alkyl, hydroxyalkyl, or $R^g$ and $R^h$ together with the nitrogen atom to which they are attached form piperazinyl or azetidinyl each optionally substituted with alkyl or hydroxyl; or a pharmaceutically acceptable salt thereof.

2. The compound or salt of embodiment 1 of Embodiment M wherein:

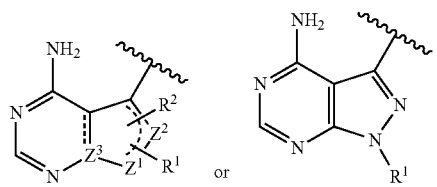

or

3. The compound or salt of embodiment 1 or 2 of Embodiment M wherein:

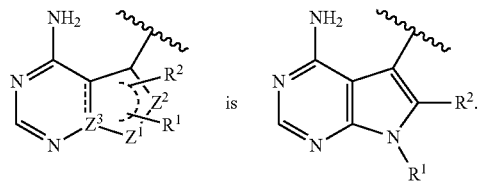 is

4. The compound or salt of any of the embodiments 1-3 of Embodiment M wherein L is O, S, NH, or N(methyl), NHCO, CONH, or NHCONH.

5. The compound or salt of any of the embodiments 1-4 of Embodiment M wherein $R^3$ and $R^4$ are independently hydrogen, methyl, fluoro, methoxy, chloro, trifluoromethyl, or trifluoromethoxy.

6. The compound or salt of any of the embodiments 1-5 of Embodiment M wherein $R^6$ and $R^7$ are independently hydrogen, methyl, methoxy, fluoro, chloro, trifluoromethyl, trifluoromethoxy, or cyano.

7. The compound or salt of any of the embodiments 1-6 of Embodiment M wherein $R^5$ is hydrogen, methyl, methoxy, fluoro, chloro, trifluoromethyl, trifluoromethoxy, or cyano; and $R^1$ is —P-Q-CH=C($R^b$)(EWG) where P is a bond, $NR^a$ (where $R^a$ is hydrogen or alkyl), —O—, S, SO, $SO_2$, or alkylene, Q is a bond, aryl or heteroaryl, $R^b$ is cyano, nitro, halo, haloalkyl, haloalkoxy, alkylthio, or alkylsulfonyl, and L is O.

8. The compound or salt of embodiment 7 of Embodiment M wherein:

—P— is a bond, $NR^a$, O, or methylene and Q is selected from:

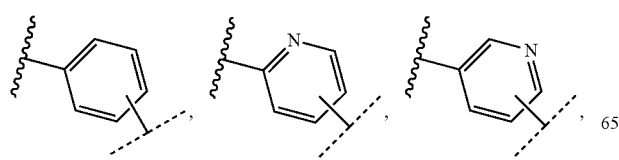

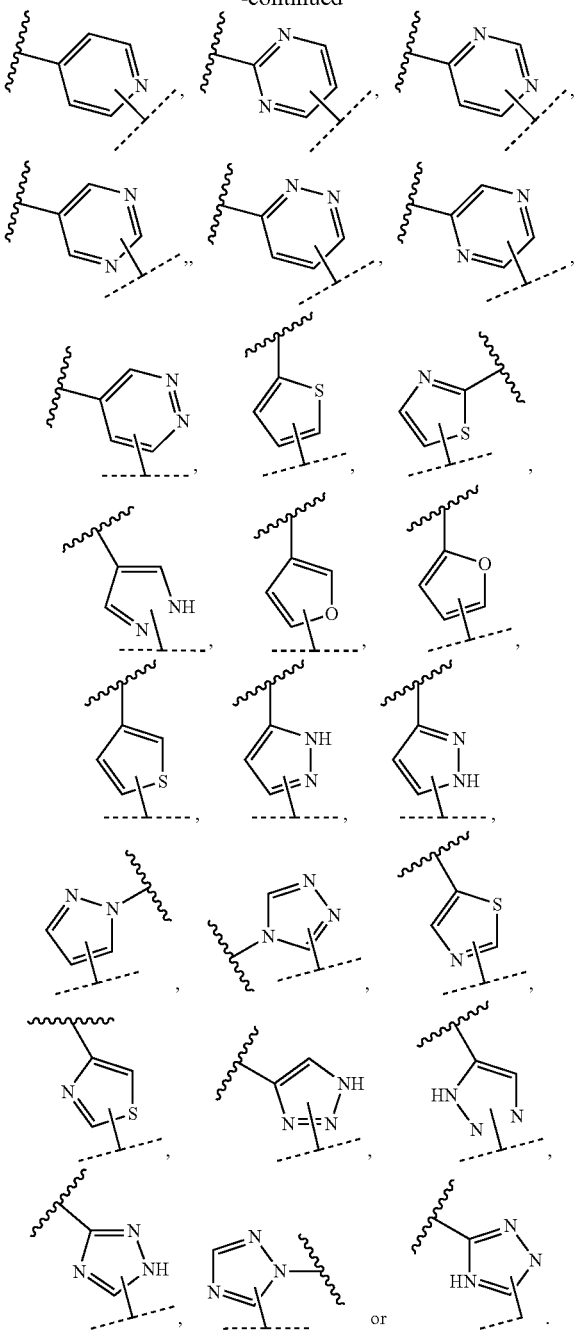

wherein each ring is substituted with one, two or three substituents independently selected from hydrogen, alkyl, alkoxy, hydroxyl, cyano, nitro, halo, haloalkyl, haloalkoxy, alkylthio, alkylsulfonyl, carboxy, alkoxycarbonyl, aminocarbonyl or aminosulfonyl.

9. The compound or salt of embodiment 7 or 8 of Embodiment M wherein $R^b$ is cyano.

10. The compound or salt of any of the embodiments 1-9 of Embodiment M wherein EWG is —CO—$NR^fR^g$ or —$SO_2NR^hR^i$ (wherein $R^f$ and $R^h$ are independently hydrogen, alkyl, or cycloalkyl and $R^g$ and $R^i$ are independently hydrogen, alkyl, substituted alkyl, cycloalkyleneNR$^d$R$^e$ (where $R^d$ and $R^e$ are independently hydrogen, alkyl, or cycloalkyl; or $R^d$ and $R^e$ together with the nitrogen atom to which they are attached form heterocycloamino), or R$^f$ and R$^g$ and R$^h$ and R$^i$ together with the nitrogen atom to which they are attached from heterocycloamino), aryl or heteroaryl wherein each of the aforementioned ring is substituted with one, two or three substituents independently selected from hydrogen, alkyl, alkoxy, hydroxyl, cyano, nitro, halo, haloalkyl, haloalkoxy, alkylthio, alkylsulfonyl, carboxy, alkoxycarbonyl, aminocarbonyl or aminosulfonyl.

11. The compound or salt of any of the embodiments 1-10 of Embodiment M wherein EWG is —CON(CH$_3$)$_2$— or

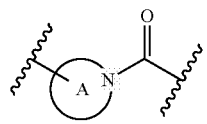

where ring A is heterocycloamino optionally substituted with hydroxyl, methyl, methoxy, amino, methylamino or dimethylamino.

12. The compound or salt of any of the embodiments 1-9 of Embodiment M wherein EWG is selected from

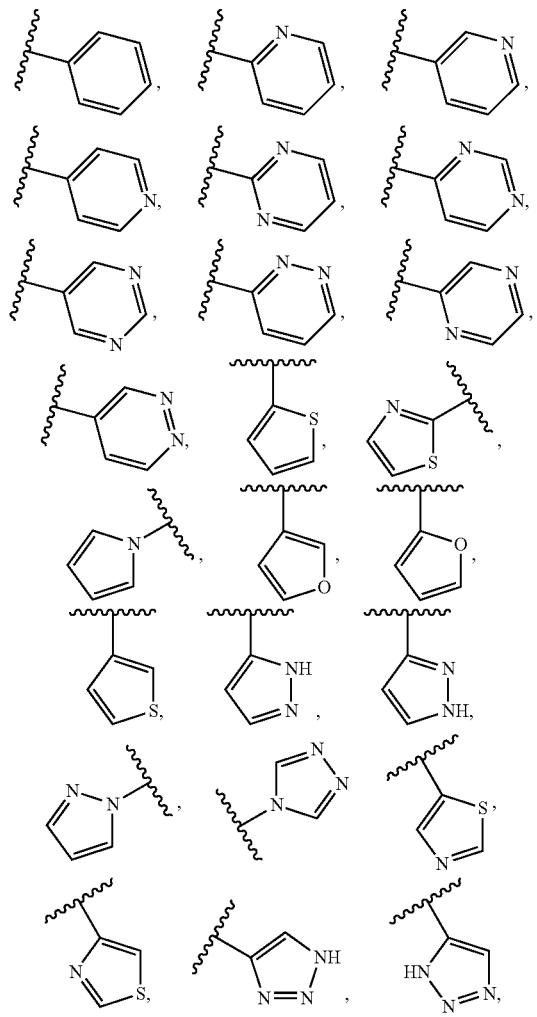

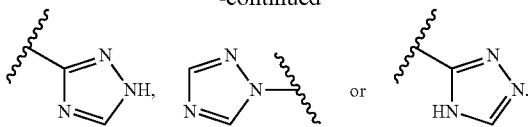

each ring independently selected from and is substituted with one, two or three substituents independently selected from hydrogen, halo, haloalkyl, cyano, haloalkoxy, or alkylsulfonyl, preferably hydrogen, fluoro, cyano, trifluoromethyl, trifluoromethoxy, or cyano.

13. The compound or salt of any of the embodiments 1-6 of Embodiment M wherein:
R$^5$ is hydrogen, alkyl, hydroxy, alkoxy, halo, haloalkyl, or haloalkoxy;
R$^1$ is —Z-(EWG')-C(R$^{b'}$)=CHR$^c$ where Z is bond, NR$^a$ (where R$^a$ is hydrogen or alkyl), —O—, S, SO, SO$_2$, alkylene, heteroalkylene, phenyl or heteroaryl, R$^{b'}$ is nitro, halo, haloalkyl, haloalkoxy, alkylthio, or alkylsulfonyl and R$^c$ is alkyl, substituted alkyl, cycloalkyl, cycloalkyleneNR$^d$R$^e$ where R$^d$ and R$^e$ are independently hydrogen, alkyl, or cycloalkyl; and
L is O.

14. The compound or salt of embodiment 13 of Embodiment M wherein:
Z is bond, NR$^a$, O or alkylene: EWG' is

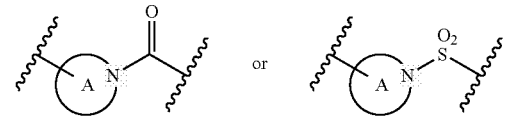

where ring A is heterocycloamino;
R$^{b'}$ is nitro, fluoro, trifluoromethyl, 2,2,2-trifluoroethyl, trifluoromethoxy, 2,2,2-trifluoroethyloxy, methylsulfonyl or methylthio, trifluoromethyl and R$^c$ is isopropyl, tert-butyl, cyclopropyl, trifluoromethyl, 2,2,2-trifluoroethyl, 1-methyl-1-methylaminoethyl, 1-methyl-1-dimethylaminoethyl, 1-methyl-1-aminoethyl, 1-methylaminocycloprop-1-ylene, or 1-dimethylaminocycloprop-1-ylene.

15. The compound or salt of embodiment 13 of Embodiment M wherein:
Z-EWG' is 3-piperidin-1-ylcarbonyl or 2-methylenepyrrolidin-1-ylcarbonyl;
R$^{b'}$ is nitro, fluoro, trifluoromethyl, 2,2,2-trifluoroethyl, trifluoromethoxy, 2,2,2-trifluoroethyloxy, methylsulfonyl or methylthio, trifluoromethyl and R$^c$ is isopropyl, tert-butyl, cyclopropyl, trifluoromethyl, 2,2,2-trifluoroethyl, 1-methyl-1-methylaminoethyl, 1-methyl-1-dimethylaminoethyl, 1-methyl-1-aminoethyl, 1-methylaminocycloprop-1-ylene, or 1-dimethylaminocycloprop-1-ylene.

16. The compound or salt of embodiment 13 of Embodiment M wherein:
Z is bond, NR$^a$, O or alkylene; EWG' is

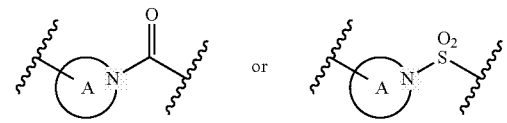

where ring A is heterocycloamino;
R$^{b'}$ is fluoro, trifluoromethyl, or 2,2,2-trifluoroethyl and R$^c$ is —C(CH$_3$)$_2$NH$_2$, —C(CH$_3$)$_2$NHCH$_3$, —C(CH$_3$)$_2$N(CH$_3$)$_2$, —C(CH$_3$)$_2$NHCH$_2$CH$_3$, —C(CH$_3$)$_2$NHCH(CH$_3$)$_2$, —C(CH$_3$)$_2$NHcyclopropyl, —C(CH$_3$)$_2$NH(CH$_2$)$_2$OCH$_3$, —C(CH$_3$)$_2$OCH$_2$CH$_3$, —C(CH$_3$)$_2$morpholine-4-yl.

17. The compound or salt of embodiment 13 of Embodiment M wherein:

Z-EWG' is 3-piperidin-1-ylcarbonyl or 2-methylenepyrrolidin-1-ylcarbonyl;

R$^{b'}$ is fluoro, trifluoromethyl, or 2,2,2-trifluoroethyl and R$^c$ is —C(CH$_3$)$_2$NH$_2$, —C(CH$_3$)$_2$NHCH$_3$, —C(CH$_3$)$_2$N(CH$_3$)$_2$, —C(CH$_3$)$_2$NHCH$_2$CH$_3$, —C(CH$_3$)$_2$NHCH(CH$_3$)$_2$, —C(CH$_3$)$_2$NHcyclopropyl, —C(CH$_3$)$_2$NH(CH$_2$)$_2$OCH$_3$, —C(CH$_3$)$_2$OCH$_2$CH$_3$, —C(CH$_3$)$_2$morpholine-4-yl.

18. The compound or salt of any of the embodiments 1-17 of Embodiment M, wherein

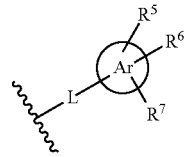

group is attached at the 4-position of the phenyl ring the carbon atom of the phenyl ring attached to

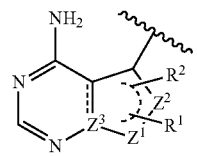

being carbon 1 and is selected from

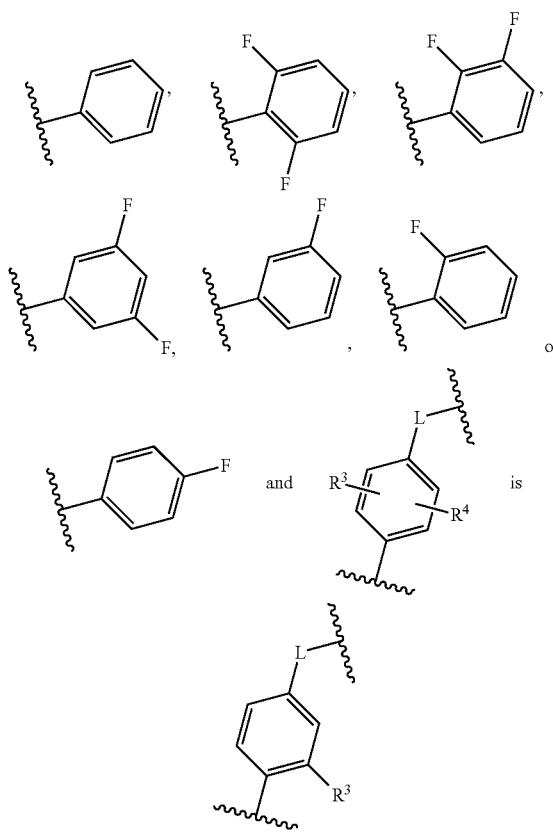

where R$^3$ is hydrogen or fluoro

GENERAL SYNTHETIC SCHEME

Compounds of this disclosure can be made by the methods depicted in the reaction schemes shown below.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this disclosure can be synthesized, and various modifications to these schemes can be made and will be suggested to one skilled in the art having referred to this disclosure. The starting materials and the intermediates, and the final products of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., more preferably from about 0° C. to about 125° C. and most preferably at about room (or ambient) temperature, e.g., about 20° C.

Compounds of Formula (I) where Z$^1$ is nitrogen, Z$^2$ is carbon or nitrogen and Z$^3$ is carbon Ar, R$^1$, R$^3$, R$^4$, R$^6$, R$^7$, and L, Ar are as defined above and R$^5$ is hydrogen, alkyl, hydroxy, alkoxy, halo, haloalkyl, or haloalkoxy can be prepared as illustrated and described in Scheme A below.

Scheme A

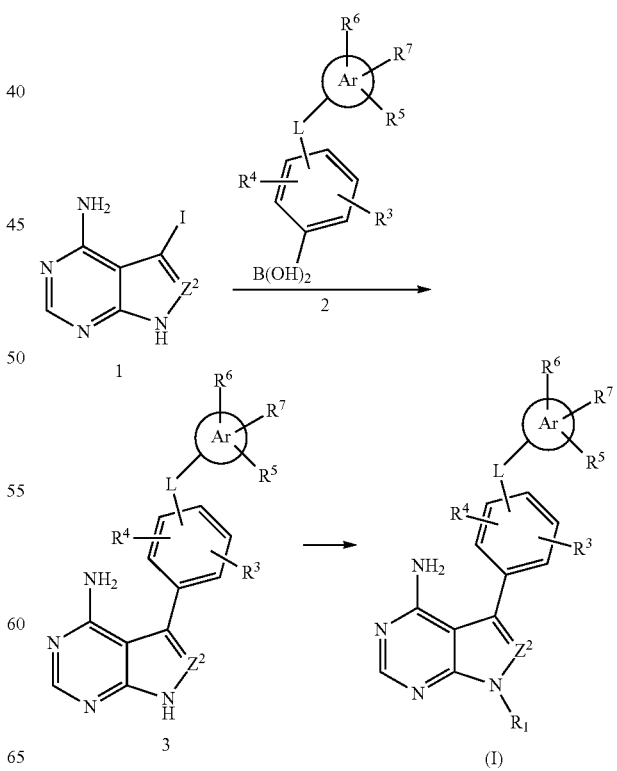

Coupling of an iodo compound of formula 1 where with a boronic acid compound of formula 2 or boronate esters thereof. Ar, $R^1$, $R^3$, $R^4$, $R^5$, $R^6$, $R^7$, L, and Ar are as defined above under Suzuki coupling reaction conditions provides a compound of formula 3. The Suzuki coupling reaction can be carried out in organic solvents (such as toluene, benzene, N,N-dimethylformamide (DMF), tetrahydrofuran, methanol, ethanol, acetonitrile, dimethoxyethane, acetone and the like) or water in the presence of base (such as sodium ethylate, sodium hydroxide, potassium hydroxide, sodium bicarbonate, potassium bicarbonate, potassium carbonate, sodium carbonate, triethylamine, and the like) and a palladium catalyst (such as tetrakis(triphenylphosphine)palladium, dichlorobis (triphenylphosphine)palladium, palladium acetate, and the like). The reaction is carried out at room temperature to 120° C. Compounds of formula 1 are either commercially available or can be readily prepared by methods well known in the art.

Treatment of a compound of formula 3 with a compound of formula $R^1$-LG where LG is a suitable leaving group such as halo, tosylate, mesylate, triflate, and the like provides a compound of Formula (I). The alkylation or arylation reaction is typically carried out in the presence of a base such as sodium hydride or potassium tert-butoxide, potassium carbonate, and the like, and a catalyst such as 18-crown-6 in a suitable solvent such as N-methylpyrolidone, dimethylformamide, tetrahydrofuran, toluene, and the like.

It will be recognized by a person skilled in the art that precursors to $R^1$ group can be substituted at any step in the synthetic procedure illustrated in Scheme A above and converted to $R^1$ group as defined above at alternate stages in the synthetic process based on feasibility of the transformations. Some such examples are described below:

1. Synthesis of compounds of Formula (I) when $R^1$=—P-Q-CH=C($R^b$)(EWG) and where $R^1$=a group of formula

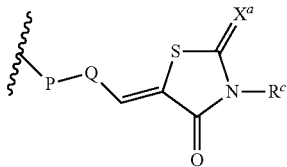

and where $R^1$=a group of formula

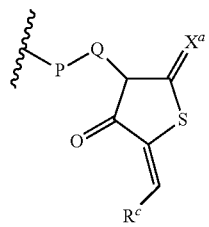

are illustrated and described below in Scheme A, methods (a) and (b) below.

Scheme A

Method (a)

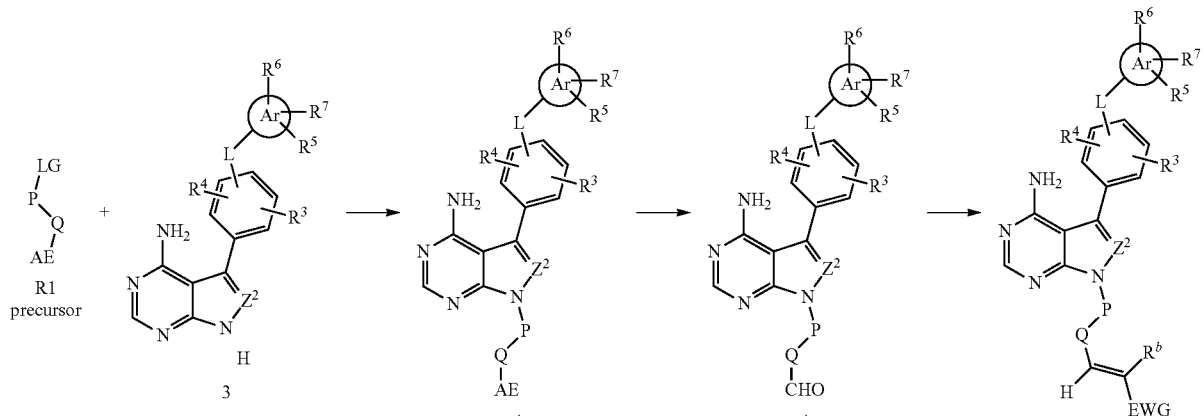

Method (b)

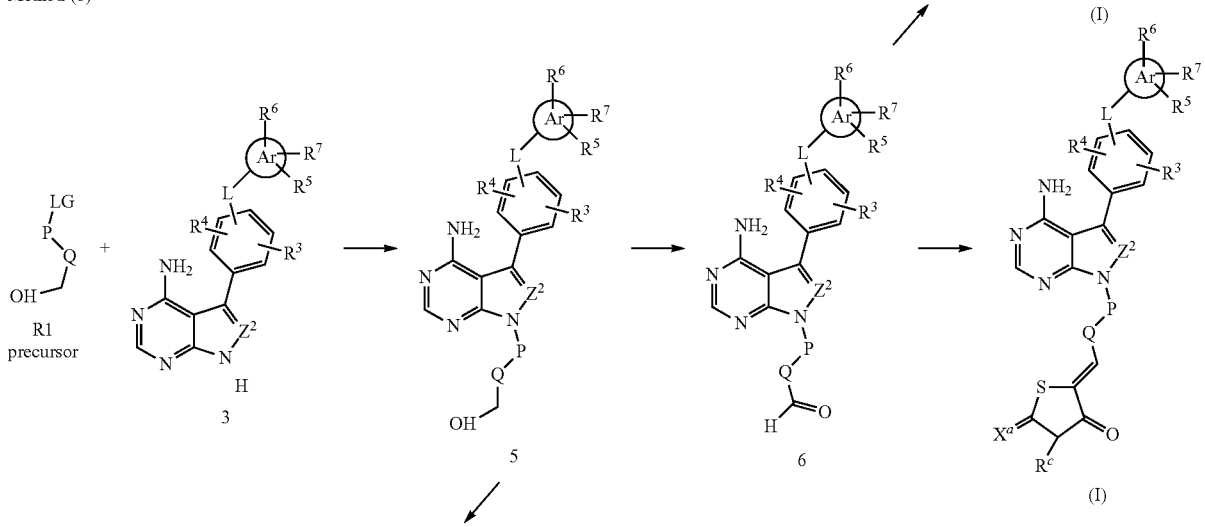

-continued

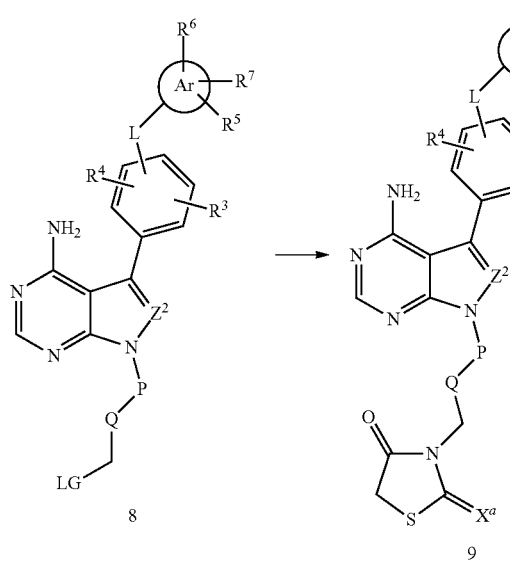

8

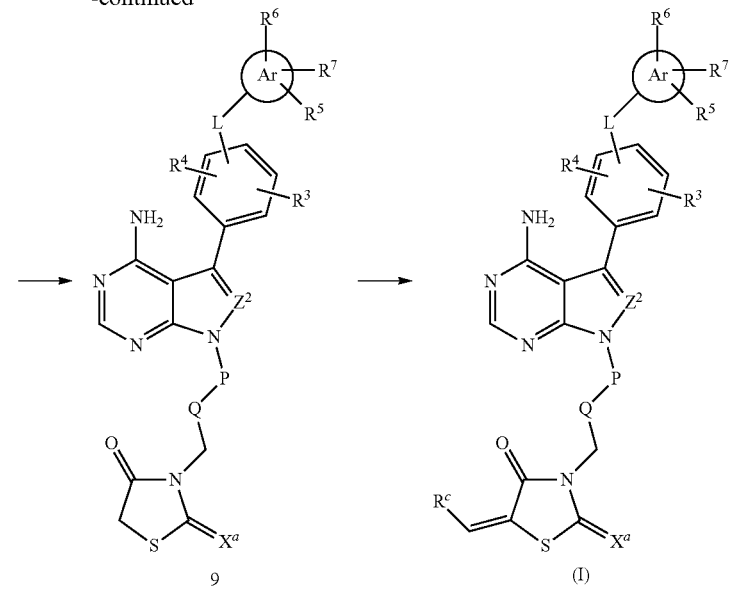

9 (I)

Method (a)

Compounds of Formula (I) where $R^1$=—P-Q-CH=C($R^b$) (EWG) can be prepared as shown in Method (a) above. Treatment of a $R^1$ precursor compound of formula LG-P-Q-AE where P and Q are as defined above and bearing a suitable leaving group (LG) such as halo, tosylate, mesylate, triflate and bearing a suitable aldehyde equivalent (AE) with a compound of formula 3 provides a compound of formula 4. The aldehyde equivalent (AE) is presented as a functional group that can be converted to the aldehyde in a simple transformation. Examples include: an acetal which can release the aldehyde under acidic conditions; a thioacetal which can release the aldehyde using mercuric or silver salts; incorporation of an alkene which can be oxidized with a mixture of osmium tetroxide and sodium periodate; cleavage of an alkene with ozone; deprotection of a primary alcohol and subsequent oxidation to the aldehyde. Several literature examples are known for generation of an aldehyde and selection of the appropriate aldehyde precursor is dependent on stability to other synthetic sequence transformations. The alkylation or arylation reaction is typically carried out as described in Scheme A above. Conversion of AE in formula (4) to the aldehyde (4a) can be achieved by any number of methods dependent on the form of AE as described above. A compound of formula 4a can then be reacted with a compound of formula $R^b$CH$_2$EWG where $R^b$ and EWG is as defined above under standard condensation reaction conditions such as using a base such as piperidine and the like, in the presence or absence of acetic acid and the like in solvents such as ethanol and the like at temperatures ranging from room temperature to reflux then provides a compound of Formula (I) where $R^1$=—P-Q-CH=C($R^b$)(EWG). Compounds of formula $R^b$CH$_2$EWG are either commercially available or they can be prepared by methods well known in the art. For example, 2-cyano-N,N-dimethylacetamide and 2-trifluoromethyl-N,N-dimethylacetamide are commercially available.

Method (b):

Alternatively, compounds of Formula (I) where $R^1$ is —P-Q-CH=C($R^b$)(EWG) can be prepared from an $R^1$ precursor compound of formula LG-P-Q-CH$_2$OH where P and Q are as defined above as shown in Method (b) above. Reaction of LG-P-Q-CH$_2$OH or hydroxyl protected derivative thereof with a compound of formula 3 under alkylation or arylation conditions provides a compound of formula 5. Oxidation of the alcoholic group provides the corresponding aldehyde of formula 6. The oxidation reaction can be carried out with oxalyl chloride, DMSO followed by triethyl amine at temperatures ranging from −78° C.-room temperature in solvents such as dichloromethane and the like (Swern oxidation conditions) or by Dess-Martin periodinane (DMP) and the like. Compound 6 can be converted to a compound of Formula (I) where $R^1$ is —P-Q-CH=C($R^b$)(EWG) as described in Method (a) above.

Alternatively, aldehyde of formula 6 can be condensed with 2,4-thiazolidenedione in the presence of ammonium acetate and acetic acid and at temperatures ranging from room temperature to 120° C. to yield compounds of Formula (I) where $R^1$ is a group of formula (a).

Alternatively, the hydroxyl group in the compound of formula 5 can be converted into a leaving group (LG) such as halo, tosylate, mesylate or triflate, and the like to provide a compound of formula 8 by methods well known in the art. For example, a compound of formula 8 where the leaving group is tosylate or mesylate can be prepared by reacting a compound of formula 5 with an agent such as toluenesulfonyl chloride or methanesulfonyl chloride respectively in the presence of a base such as pyridine, and the like and in an organic solvent such as dichloromethane, and the like, at temperatures from −20° C. to reflux. Alkylation of compounds of formula 8 with 2,4-thiazolidenedione in the presence of a base such as sodium hydride or potassium tert-butoxide, and the like in an organic solvent such as toluene or dimethylformamide, THF, and the like, at temperatures from 0° C. to 100° C. provides a compound of formula 9. Condensation of a compound 9 with an aldehyde of formula $R^cCHO$, such as cyclopropyl aldehyde or t-butyl aldehyde, and the like in an organic solvent such as ethanol and at temperatures ranging from 0° C. to reflux yield compounds of Formula (I) where $R^1$ is a group of formula (b).

2. Substitution of precursors to $R^1$ in the synthesis of compounds of Formula (I) when $R^1$ is Z-(EWG')-C($R^b$)=CHR$^c$ where Z is a bond or alkylene and EWG' is N-carbonylheterocycloamino is illustrated and described in method c below.

Method (c)

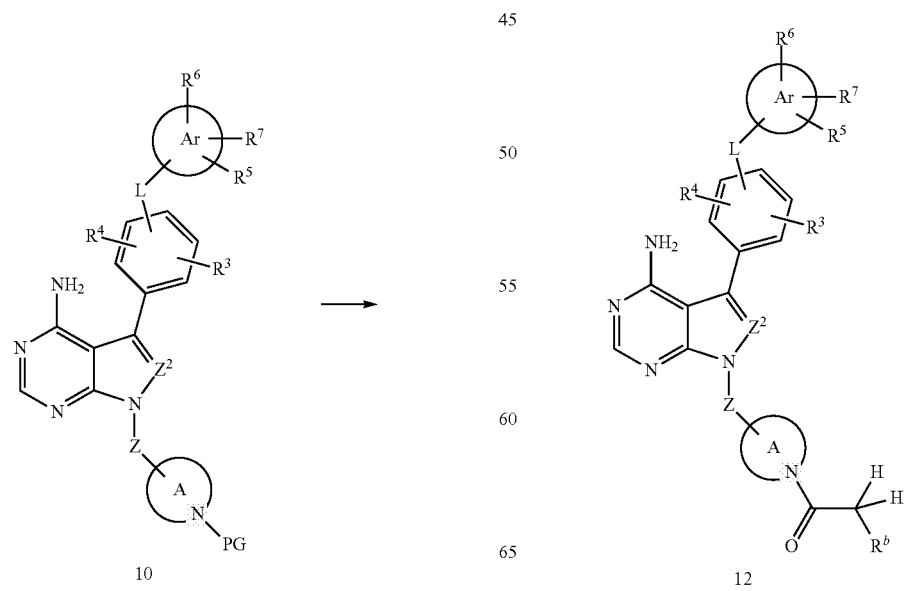

-continued

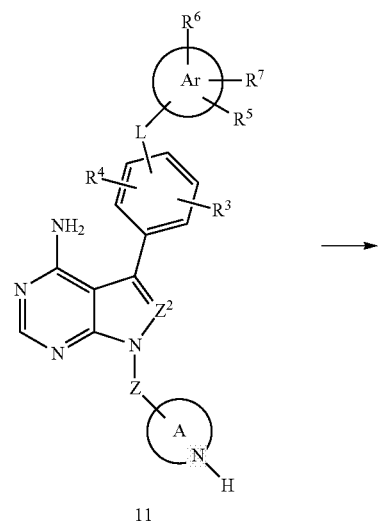

-continued

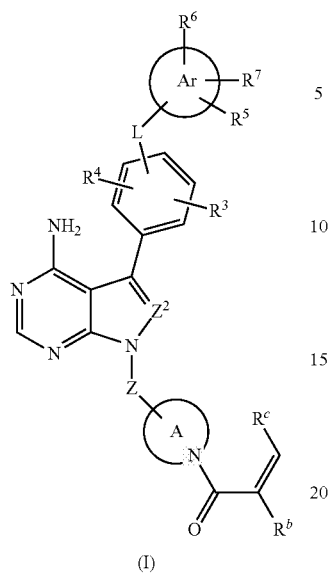
(I)

Treatment of a N-protected heterocycloamino R1 precursor compound (Suitable nitrogen protecting groups (PG) include t-butyloxycarbonyl (BOC), carbobenzyloxy (Cbz), or 2-trimethylsilyl-ethoxymethyl (SEM)) bearing an alcohol with a compound of formula 3 under Mitsunobu reaction conditions provides a compound of formula 10 where Ar, $R^3$, $R^4$, $R^5$, $R^6$, $R^7$, L, Ar, and $Z^2$ are as defined above. Removal of the amino protecting group can be effected using strong acid (TFA or HCL in the case of a Boc group, hydrogenolysis in the case of Cbz, or fluoride anion to remove the SEM), to provide the amine of formula 11. Coupling of compound of formula 11 with a compound of formula $R^bCH_2CO_2H$ such as 2-cyanoacetic acid or 2-trifluoromethylacetic acid, under standard amide coupling conditions such as carbon diimidazole (CDI) and the like or an acid derivative thereof provides a compound of formula 12. Subsequent condensation of a compound of formula 12 with aldehydes of formula $R^cCHO$ where $R^c$ is as defined above e.g., t-butyl or cyclopropyl aldehyde, under standard condensation reaction conditions such as using a base such as piperidine and the like, in the presence or absence of acetic acid and the like in solvents such as ethanol and the like at temperatures ranging from room temperature to reflux then provides a compound of Formula (I). It will recognized by a person of ordinary skill in the art that the EWG' moiety can be assembled at multiple points throughout the synthetic scheme and standard protecting group (PG) strategies can be employed as required.

Compounds of Formula (I) where $Z^1$ and $Z^3$ are nitrogen and $Z^2$ is carbon, Ar, $R^1$, $R^3$, $R^4$, $R^6$, $R^7$, and L, Ar are as defined above and $R^5$ is hydrogen, alkyl, hydroxy, alkoxy, halo, haloalkyl, or haloalkoxy can be prepared as illustrated and described in Scheme B by method (d) below.

Scheme B

Method (d):

Cross coupling (Suzuki) of a compound of formula 13 (available commercially) with an appropriately substituted boronic acid or boronate esters of formula 13 (as described in Scheme A) provides a compound of formula 15 where $R^1$ is as defined above. Halogenation of compound 15 with a suitable halogenating agent such as N-bromosuccinamide, bromine, and the like, in an organic solvent (such as DMF, dichloromethane, tetrahydrofuran, toluene, acetic acid, water and the like) at temperatures ranging from −78° C. to reflux temperature provides a compound of formula 16. Compound 16 is then coupled with a compound of formula 17 under Suzuki coupling reaction conditions to provide a compound of Formula (I) where Ar, R¹, R³, R⁴, R⁵, R⁶, R⁷, L, and Ar are as defined above.

It will be recognized by a person skilled in the art that precursors to R¹ can be substituted at any step in Scheme 2 above where R¹ exists and converted to R¹ at alternate stages in the synthetic process based on feasibility of the transformations. Some such transformations are described below:

1. Synthesis of a compound of Formula (I) wherein R¹ is —P-Q-CH=C(R$^b$)(EWG) or a group of formula

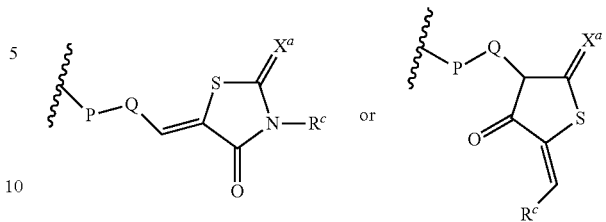

are illustrated and described in Methods (e) below.

Method (e):

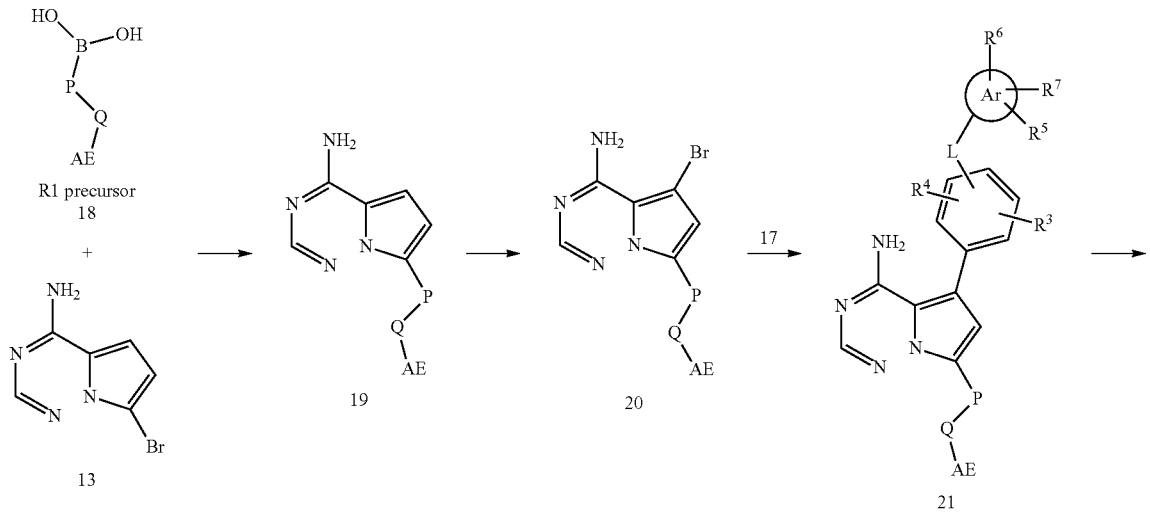

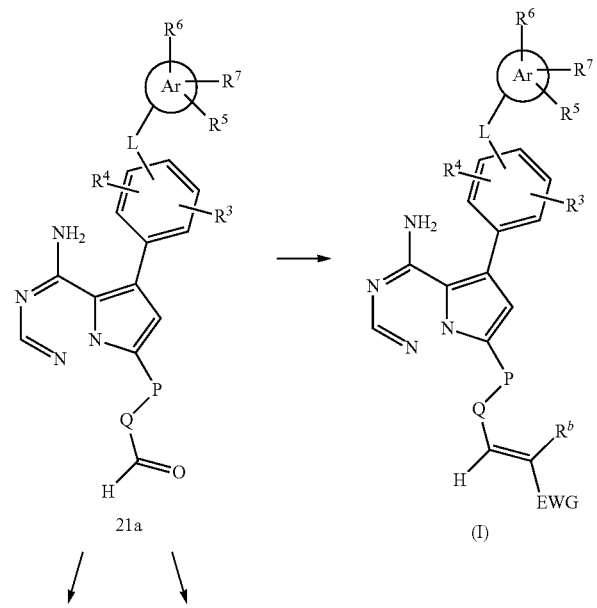

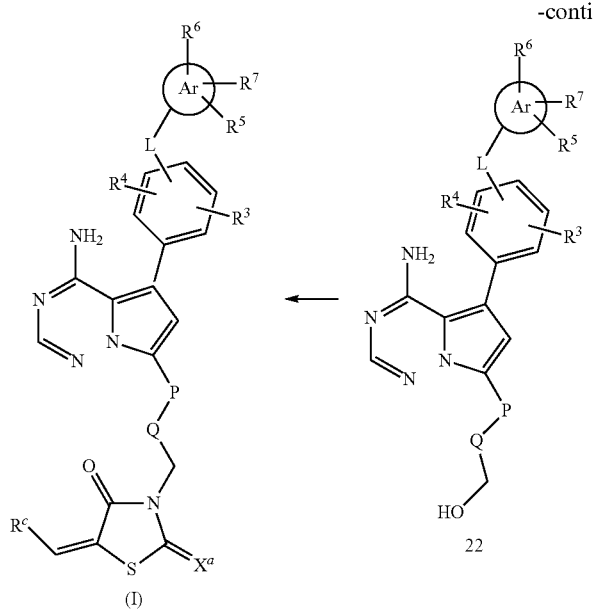

Cross coupling of a compound of formula 13 (available commercially) with a $R^1$ precursor compound of formula 18 bearing a suitable aldehyde equivalent (AE) under Suzuki conditions as described in Scheme A, provides a compound of formula 19 where P and Q are as defined above. Halogenation of compound 19 may be accomplished by treatment with a halogenating agent such as N-bromosuccinamide, bromine and the like in a suitable solvent (such as DMF, dichloromethane, tetrahydrofuran, toluene, acetic acid, water, and the like) and at temperatures ranging from −78° C. to reflux temperature provides a compound of formula 20 which can then be converted to a compound of formula 21 as described in Scheme A. Conversion of AE in formula 21 to the aldehyde 21a can be achieved by any number of methods dependent on the form of AE as described in Scheme A. Condensation of the aldehyde group in compound 21 $R^bCH_2EWG$ where Rb and EWG is as defined above under standard condensation reaction conditions then provides a compound of Formula (I) where $R^1=$—P-Q-CH=C$(R^b)$(EWG). Compounds of formula $R^bCH_2EWG$ are either commercially available or they can be prepared by methods well known in the art. For example, 2-cyano-N,N-dimethylacetamide and 2-trifluoromethyl-N,N-dimethylacetamide are commercially available.

Alternatively, compound 21 can be condensed with 2,4-thiazolidenedione in the presence of ammonium acetate and acetic acid at temperatures ranging from room temperature to 120° C. to yield compounds of formula (I) where $R^1$ is a group of formula (a) as defined above.

Alternatively, a $R^1$ precursor bearing an alcohol moiety of formula LG-P-Q-CH$_2$OH or a hydroxyl protected derivative thereof can be used in lieu of compound of formula 18. After LG-P-Q-CH$_2$OH is attached to compound 13, the hydroxyl group is oxidized to aldehyde to provide a compound of formula 19 and then covered to a compound of Formula (I) as described in Method (C) above. The hydroxy group can be readily oxidized to aldehyde using Swern or Dess-Martin conditions previously described.

Alternatively, the compound of formula 21 can be converted to a compound of formula 22 and then converted to a compound of Formula (I) where $R^1$ is a group of formula (b) as described above.

2. Substitution of precursors to $R^1$ in the synthesis of compounds of Formula (I) when $R^1$ is Z-(EWG')-C$(R^b)$=CHR$^c$ where Z is a bond or alkylene and EWG' is heterocycloamino is illustrated and described in method f below. The EWG' moiety can be assembled at multiple points in the synthetic scheme. Standard protecting group (PG) strategies employed by those skilled in the art can be employed as required.

Method (f):

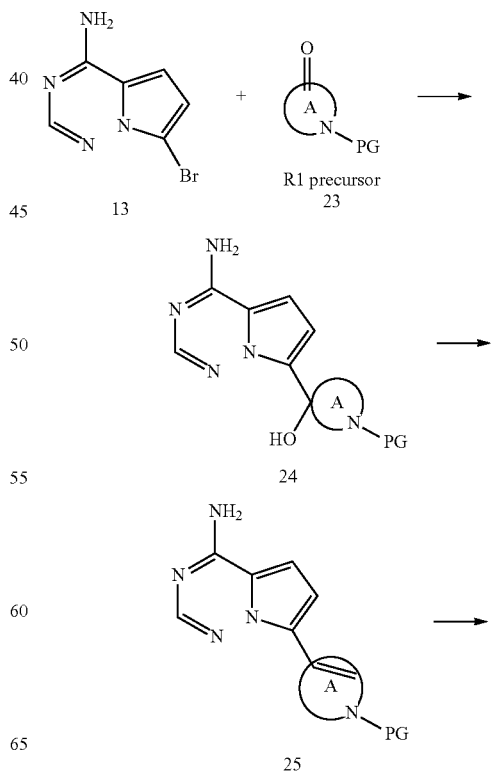

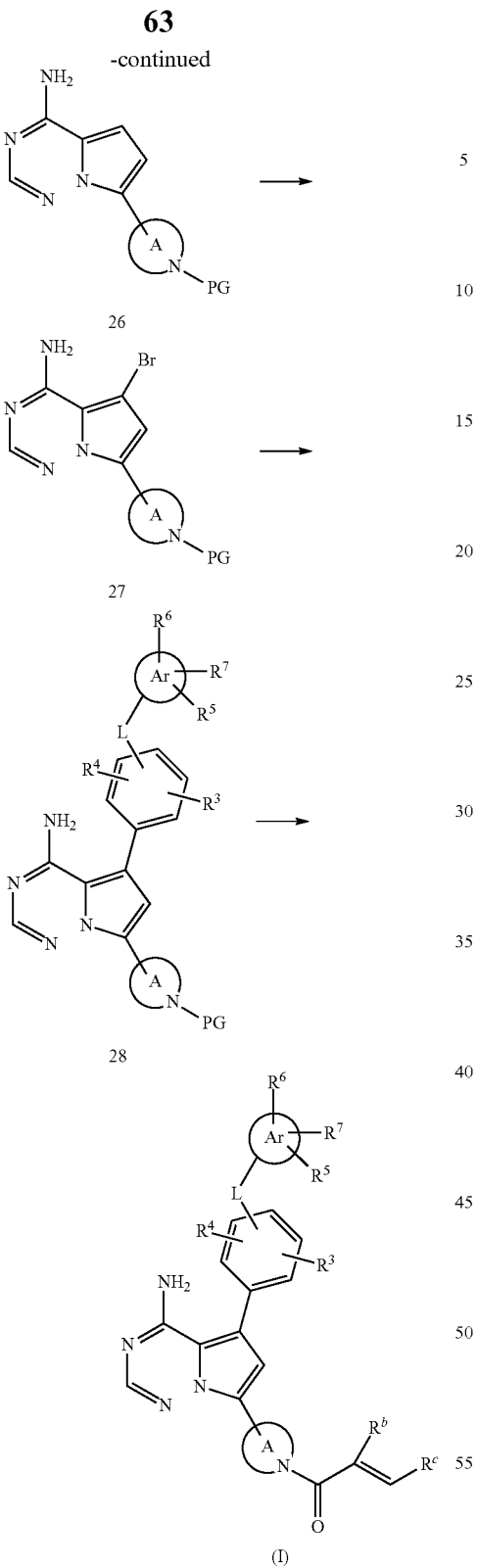

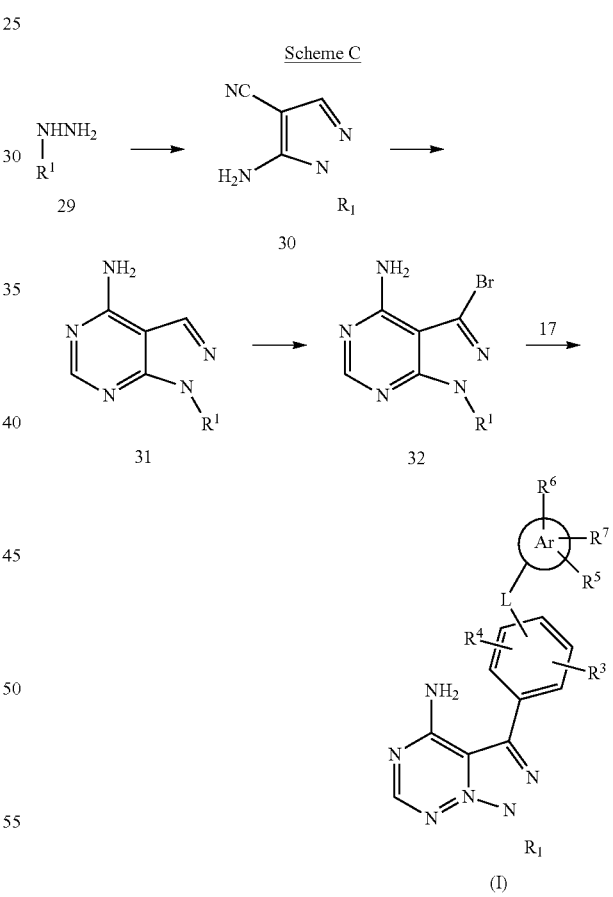

where PG is a suitable protecting group such as tert-butoxycarbonyl (Boc), benzyl (Bn) or 2-trimethylsilyl-ethoxymethyl (SEM)), provides a compound of formula 24 which is converted to a compound of formula 25 under dehydration reaction conditions e.g., treatment of compound 24 with acids such as trifluoroacetic anhydride or trifluoroacetic acid, and the like, in solvents such as pyridine, toluene, methanol, and the like and temperatures ranging from −20° C. to reflux. Reduction of the double bond in the compound of formula 25 with a suitable hydrogenation reaction conditions e.g., with platinum oxide or palladium hydroxide or palladium on carbon in alcoholic solvents such as methanol or ethanol, and the like in the presence or absence of acetic acid and under a hydrogen atmosphere provides a compound of formula 26.

Halogenation of a compound of formula 26 with a suitable halogenating agent as described in scheme B above provides a compound of formula 27 which can then be converted to a compound of Formula (I) as described in method c above.

Compounds of Formula (I) where $Z^1$ and $Z^2$ are nitrogen and $Z^3$ is carbon and $R^1$, $R^3$, $R^4$, $R^5$, $R^6$, $R^7$, L, and Ar are as defined above can be prepared as illustrated and described in Scheme C below.

Treatment of compound 13 with trimethylsilyl chloride in solvents such as tetrahydrofuran (THF) at temperatures ranging from 0° C. to room temperature prior to treatment by a Grignard reaction (for example by treatment with isopropyl magnesium chloride in THF at temperatures ranging from 0° C. to room temperature) and subsequent addition of $R^1$ precursor compound of formula 23 bearing a ketone moiety Reaction of a hydrazine compound of formula I where $R^1$ is as defined above with ethoxymethylene malonitrile in a suitable organic solvent such as ethanol and the like and at temperatures from 0° C. to reflux provide a compound of formula 30. Compound of formula I that are either commercially available or readily synthesized by methods that are well known in the art.

Treatment of compound 30 with formamide or formamidine in the absence of solvent or in solvents such as ethanol and the like at temperatures from room temperature to 200° C. provides a compound of formula 31. Halogenation of 31 under halogenating conditions described above provides the compound of formula 32 which can then be converted to a compound of Formula (I) as described in Scheme A above.

It will be recognized by a person skilled in the art that precursors to group $R^1$ can be substituted at any step in Scheme C above where $R^1$ exists and then converted to $R^1$ at alternate stages in the synthetic process based on feasibility of the transformations. Some such transformations are described below:

1. Synthesis of a compound of Formula (I) wherein $R^1$ is —P-Q-CH=C($R^b$)(EWG) or a group of formula

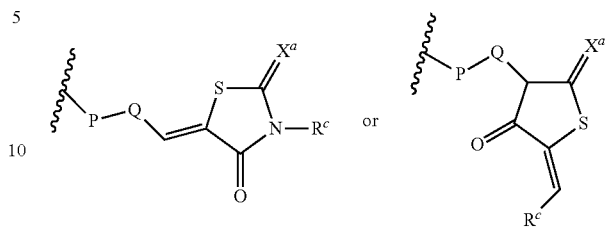

are illustrated and described in Methods (g) below.

Method (g):

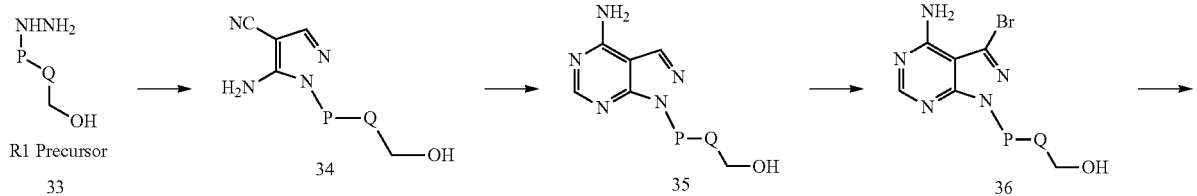

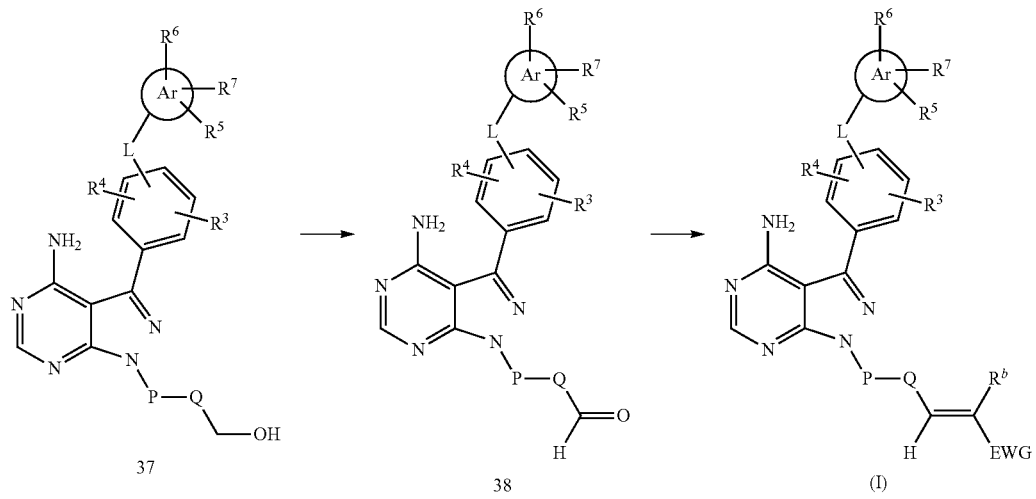

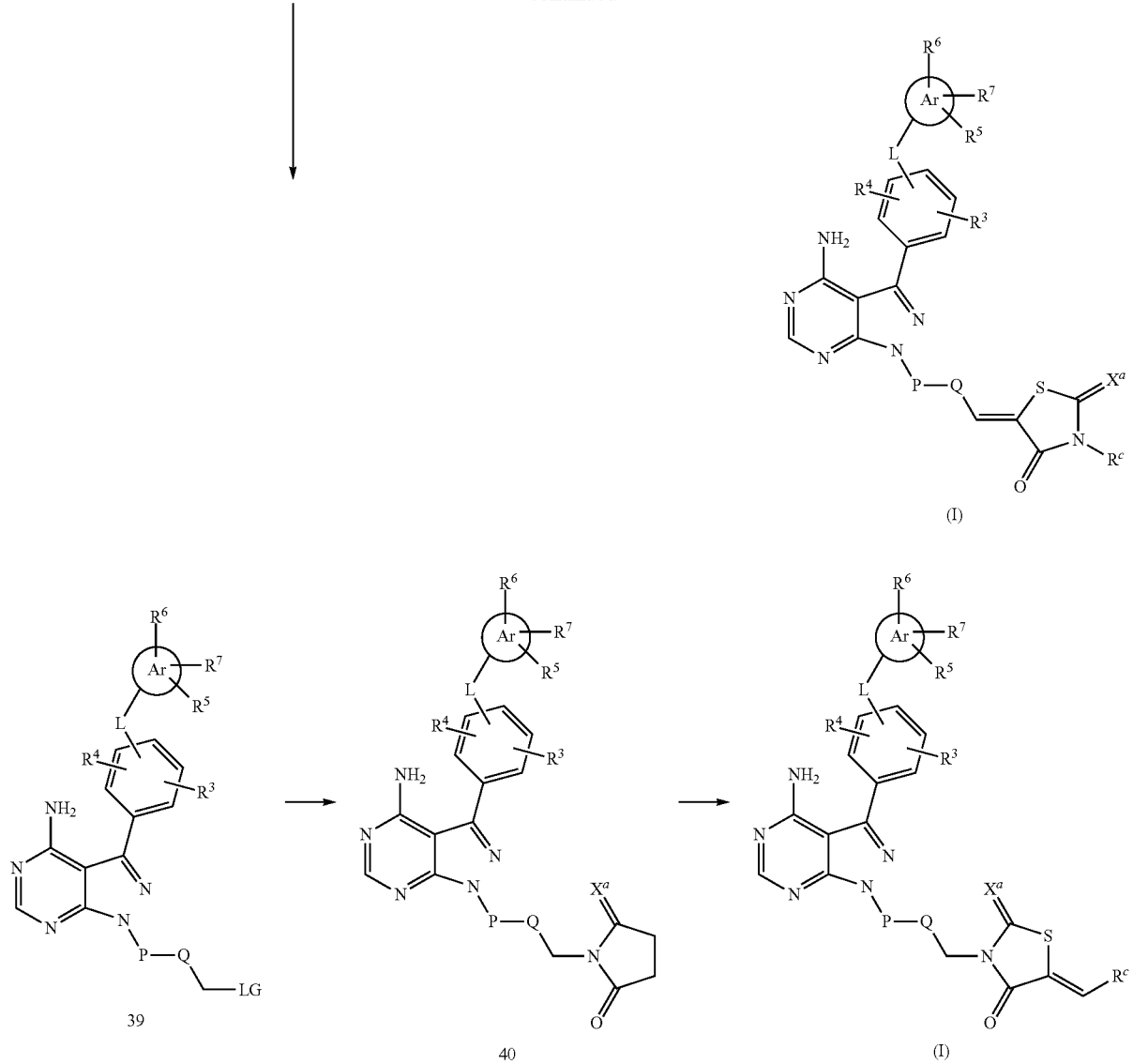

Treatment of a $R^1$ precursor containing hydrazines of formula 33 where P and Q are as defined above with ethoxymethylene malonitrile as described in Scheme C provides a compound of formula 34 which is converted to a compound of formula 36 as described in Scheme C. Coupling of compound 36 with a compound of formula 17 provides a compound of formula 37 which is converted to a compound of Formula (I) where $R^1$ is —P-Q-CH=C($R^b$)(EWG) or a group of formula 2. Substitution of precursors to $R^1$ in the synthesis of compounds of Formula (I) when $R^1$ is Z-(EWG')-C($R^b$)=CHR$^c$ where Z is a bond and EWG' is N-carbonylheterocycloamino is illustrated and described in method (h) below. The EWG' moiety can be assembled at multiple points in the synthetic scheme. Standard protecting group (PG) strategies employed by those skilled in the art can be employed as required.

Method (h):

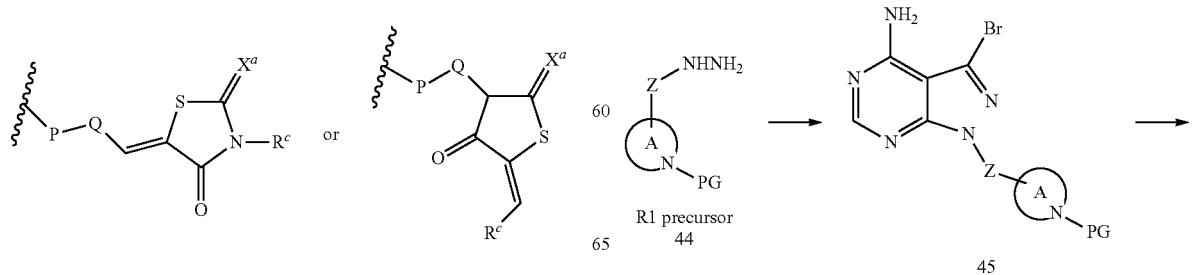

under reaction conditions described in Methods (a)-(c) above.

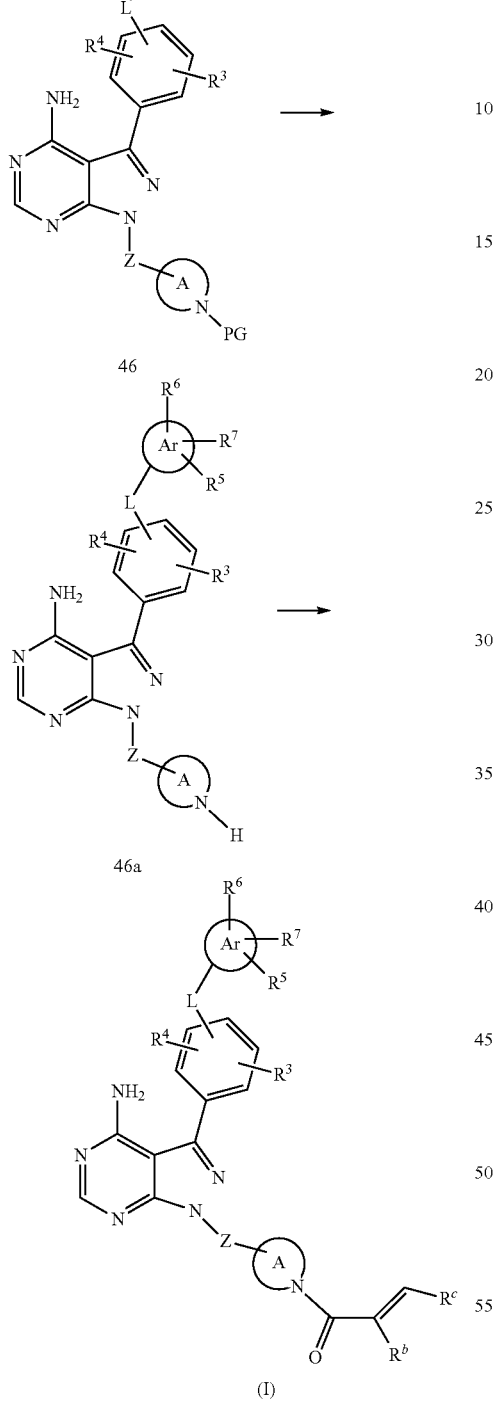

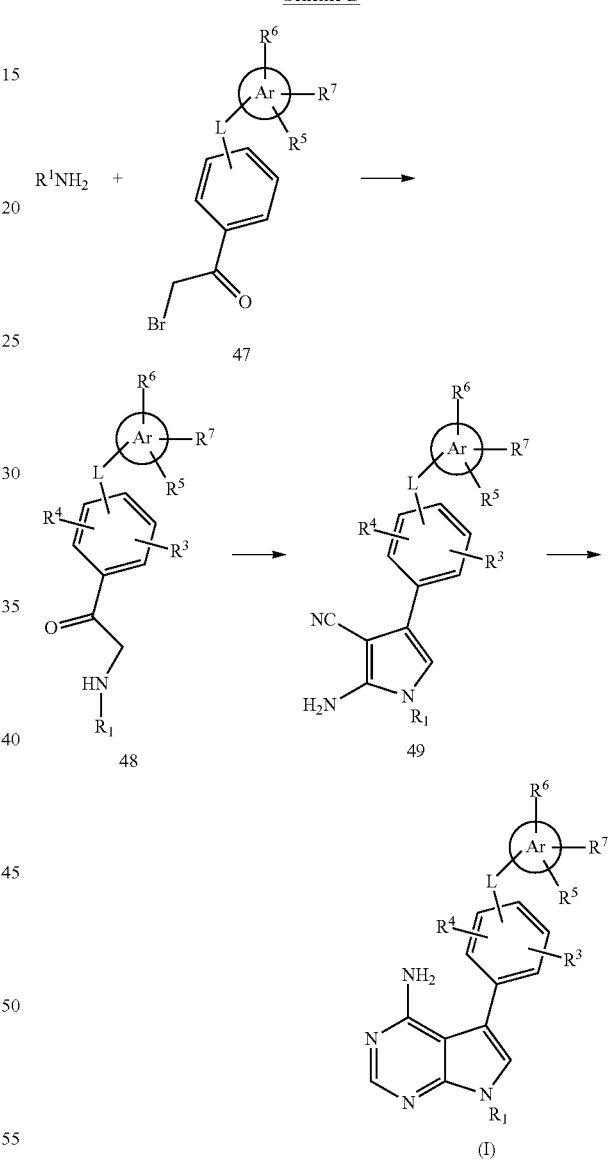

trifluoroacetic acid in dichloromethane at 0° C. to reflux for BOC and catalytic hydrogenation in ethyl alcohol for CBZ, provides a Compound 46a that can then be converted to a compound of Formula (I) by methods previously described in method c.

Compounds of Formula (I) where $Z^1$ is nitrogen and $Z^2$ and $Z^3$ are carbon and $R^1$, $R^3$, $R^4$, $R^5$, $R^6$, $R^7$, L, and Ar are as defined above can be prepared as illustrated and described in Scheme D below.

Substituting compound of formula 33 where Z is a bond or alkylene and where PG is a suitable nitrogen protecting group such as tert-butoxycarbonyl (Boc), benzyl (Bn) or 2-trimethylsilyl-ethoxymethyl (SEM)) with a compound of formula 44 followed by steps 2-5 in Method (g) above provides a compound of formula 46. Removal of the amine protecting group under standard conditions such as HCl in ethyl acetate or Alkylation of a compound of the formula $R^1H_2$ where $R^1$ is as defined above with a compound of formula 47 under standard alkylation reaction conditions (e.g., reacting in the presence of a base such as sodium hydride or potassium tert-butoxide, potassium carbonate, and the like, and a catalyst such as 18-crown-6 in a suitable solvent such as N-methylpyrolidone, dimethylformamide, tetrahydrofuran, toluene and the like) provides a compound of formula 48. Reaction of compound 48 with malonitrile and a base such as potassium hydroxide, sodium hydroxide, and the like in a suitable solvent such as methanol or ethanol and the like at temperatures from 0° C. to reflux provides a compound of formula 49 which is then converted to a compound of Formula (I) as described in Scheme C above.

As discussed previously, it will be recognized by a person skilled in the art that precursors to group R¹ can be substituted at any step in Scheme D above where R¹ exists and then converted to R¹ at alternate stages in the synthetic process based on feasibility of the transformations. For example, an amine of formula NH$_2$—P-Q-CH$_2$OH where —P-Q-OH is a precursor group for the R¹ group or an amine of formula

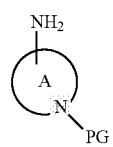

can be used instead R¹NH$_2$ in Scheme D above to give a compound of formula

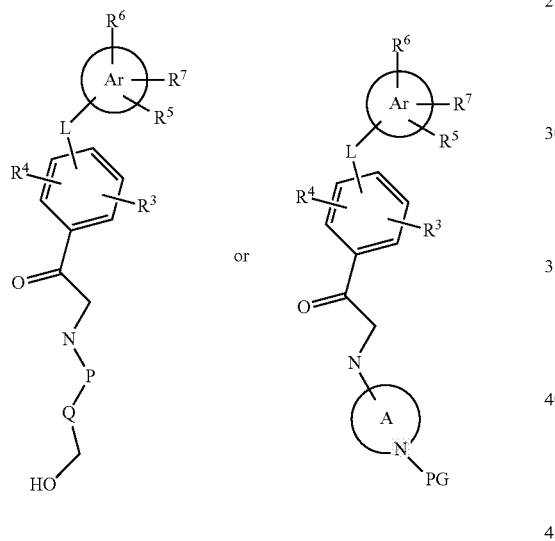

respectively, which is then converted to a compound of Formula (I)

R¹ is —P-Q-CH=C(R$^b$)(EWG) or a group of formula

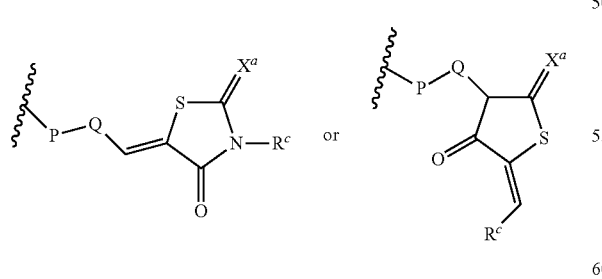

or -(heterocycloamino)-C(R$^b$)=CHR$^c$ following the procedures described in Scheme D and Methods (a)-(c) above.

Substitution of precursors to R¹ in the synthesis of compounds of Formula (I) when R¹ is Z-(EWG')-C(R$^b$)=CHR$^c$ where Z is heteroalkylene or aryl and EWG' is —NR'CO— is illustrated and described in Scheme E below.

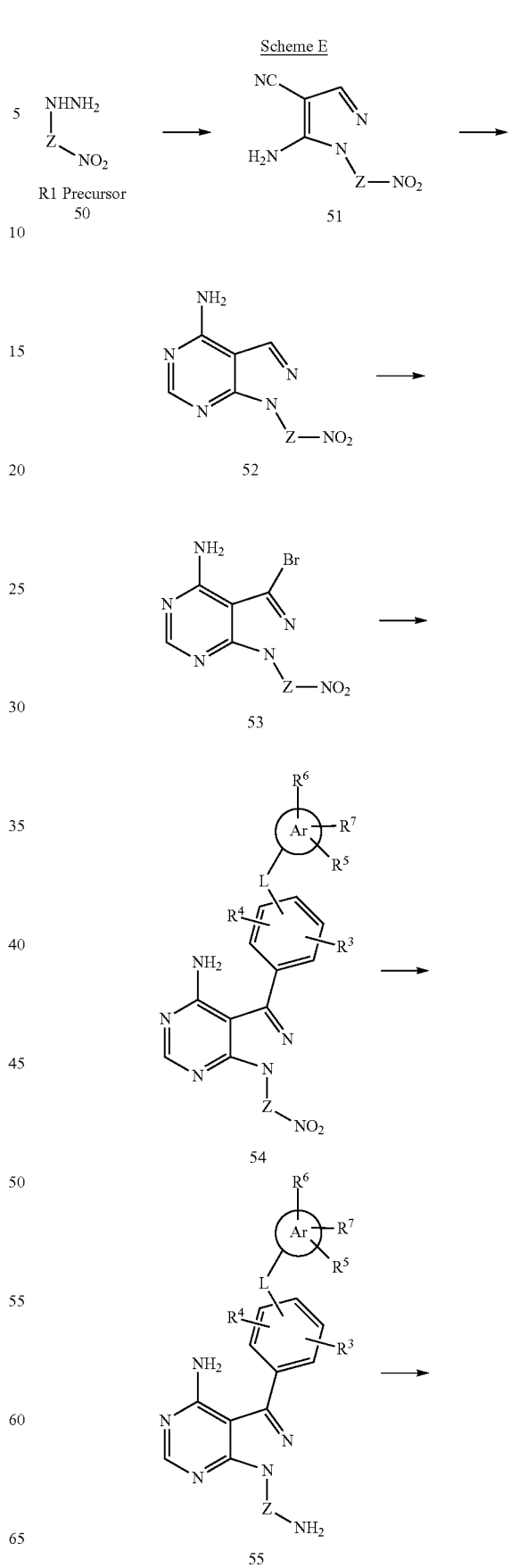

Scheme E

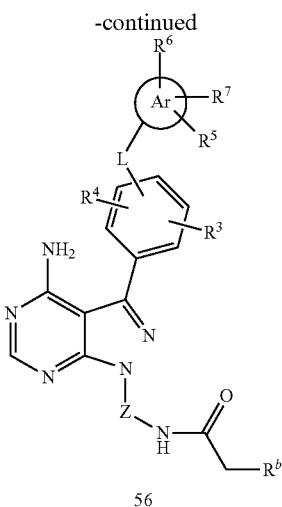

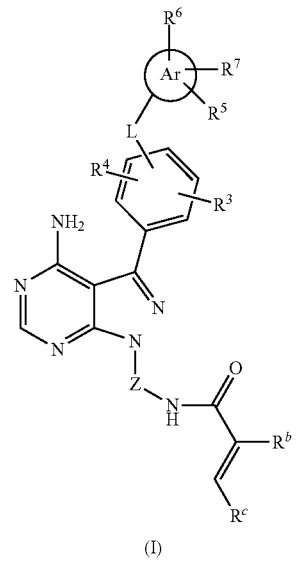

Treatment of a $R^1$ precursor containing hydrazines of formula 50 where Z is heteroalkylene or aryl and EWG' is —NR'CO— and $R^3$-$R^7$, L and Ar defined above with ethoxymethylene malonitrile as described in Scheme C provides a compound of formula 51 which is converted to a compound of formula 53 as described in Scheme C. Coupling of a bromo compound of formula 53 with a boronic acid compound or boronate esters thereof of formula 17 under Suzuki coupling reaction conditions as described in Scheme A provides a compound of formula 54. Reduction of nitro substituent of compound 54 may be accomplished by treatment with a reducing agent such as zinc powder and the like in a suitable solvent such as acetic acid and the like, or by catalytic hydrogenation to provide a compound of formula 55. Coupling of compounds of formula 55 with a compound of formula $R^b CH_2 CO_2 H$ such as 2-cyanoacetic acid or 2-trifluoromethylacetic acid, under standard amide coupling conditions such as carbon diimidazole (CDI) and the like or an acid derivative thereof provides a compound of formula 56. Subsequent condensation of a compound of formula 56 with aldehydes of formula $R^c$CHO where $R^c$ is as defined above e.g., t-butyl or cyclopropyl aldehyde, under standard condensation reaction conditions such as using a base such as piperidine and the like, in the presence or absence of acetic acid and the like in solvents such as ethanol and the like at temperatures ranging from room temperature to reflux then provides a compound of Formula (I). It will recognized by a person of ordinary skill in the art that the EWG' moiety can be assembled at multiple points throughout the synthetic scheme and standard protecting group (PG) strategies can be employed as required.

Utility

The compounds of Formula (I) are tyrosine kinase inhibitors, in particular Btk and hence are useful in the treatment of autoimmune disease, e.g., inflammatory bowel disease, arthritis, lupus, rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, Sjogren's syndrome, multiple sclerosis, Guillain-Barre syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, endometriosis, interstitial cystitis, neuromyotonia, scleroderma, or vulvodynia.

The compounds of Formula (I) are also useful in the treatment of In another embodiment of this aspect, the patient in need is suffering from a heteroimmune condition or disease, e.g., graft versus host disease, transplantation, transfusion, anaphylaxis, allergy, type I hypersensitivity, allergic conjunctivitis, allergic rhinitis, or atopic dermatitis.

In another embodiment of this aspect, the patient in need is suffering from an inflammatory disease, e.g., asthma, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, or vulvitis.

In another embodiment of this aspect, the patient is suffering from inflammatory skin disease which includes, by way of example, dermatitis, contact dermatitis, eczema, urticaria, rosacea, and scarring psoriatic lesions in the skin, joints, or other tissues or organs.

In yet another embodiment of this aspect, the subject in need is suffering from a cancer. In one embodiment, the cancer is a B-cell proliferative disorder, e.g., diffuse large B cell lymphoma, follicular lymphoma, chronic lymphocytic lymphoma, chronic lymphocytic leukemia, B-cell prolymphocytic leukemia, lymphoplamascytic lymphoma/Waldenstrom macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, burkitt lymphoma/leukemia, or lymphomatoid granulomatosis. In some embodiments, the compound of Formula (I) is administered in combination with another an anti-cancer agent e.g., the anti-cancer agent is an inhibitor of mitogen-activated protein kinase signaling, e.g., U0126, PD98059, PD184352, PD0325901, ARRY-142886, SB239063, SP600125, BAY 43-9006, wortmannin, or LY294002.

In yet another embodiment, the patient in need is suffering from a thromboembolic disorder, e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, or deep venous thrombosis.

In a fourth aspect, the disclosure is directed to use of compound of Formula (I) (and any embodiments thereof described herein) for use as a medicament. In one embodiment, the use of compound of Formula (I) is for treating inflammatory disease or proliferative diseases.

In a fifth aspect, is the use of a compound of Formula (I) in the manufacture of a medicament for treating an inflammatory disease in a patient in which the activity of Btk or other tyrosine kinases contributes to the pathology and/or symptoms of the disease. In one embodiment of this aspect, the tyrosine kinase protein is Btk. In another embodiment of this aspect, the inflammatory disease is respiratory, cardiovascular, or proliferative diseases. In any of the aforementioned aspects involving the treatment of proliferative disorders, including cancer, are further embodiments comprising administering the compound of Formula (I) in combination with at least one additional agent selected from the group consisting of alemtuzumab, arsenic trioxide, asparaginase (pegylated or non-), bevacizumab, cetuximab, platinum-based compounds such as cisplatin, cladribine, daunorubicin/doxorubicin/idarubicin, irinotecan, fludarabine, 5-fluorouracil, gemtuzamab, methotrexate, paclitaxel, Taxol™, temozolomide, thioguanine, or classes of drugs including hormones (an antiestrogen, an antiandrogen, or gonadotropin releasing hormone analogues, interferons such as alpha interferon, nitrogen mustards such as busulfan or melphalan or mechlorethamine, retinoids such as tretinoin, topoisomerase inhibitors such as irinotecan or topotecan, tyrosine kinase inhibitors such as gefinitinib or imatinib, or agents to treat signs or symptoms induced by such therapy including allopurinol, filgrastim, granisetron/ondansetron/palonosetron, dronabinol. When combination therapy is used, the agents can be administered simultaneously or sequentially.

Testing

The kinase inhibitory activity of the compounds of the present disclosure can be tested using the in vitro and in vivo assays described in Biological Examples 1-6 below.

Administration and Pharmaceutical Composition

In general, the compounds of this disclosure will be administered in a therapeutically effective amount by any of the accepted modes of administration for agents that serve similar utilities. Therapeutically effective amounts of compounds of Formula (I) may range from about 0.01 to about 500 mg per kg patient body weight per day, which can be administered in single or multiple doses. Preferably, the dosage level will be about 0.1 to about 250 mg/kg per day; more preferably about 0.5 to about 100 mg/kg per day. A suitable dosage level may be about 0.01 to about 250 mg/kg per day, about 0.05 to about 100 mg/kg per day, or about 0.1 to about 50 mg/kg per day. Within this range the dosage can be about 0.05 to about 0.5, about 0.5 to about 5 or about 5 to about 50 mg/kg per day. For oral administration, the compositions are preferably provided in the form of tablets containing about 1.0 to about 1000 milligrams of the active ingredient, particularly about 1.0, 5.0, 10, 15, 20, 25, 50, 75, 100, 150, 200, 250, 300, 400, 500, 600, 750, 800, 900, and 1000 milligrams of the active ingredient. The actual amount of the compound of this disclosure, i.e., the active ingredient, will depend upon numerous factors such as the severity of the disease to be treated, the age and relative health of the subject, the potency of the compound being utilized, the route and form of administration, and other factors.

In general, compounds of this disclosure will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of formula (I) in combination with at least one pharmaceutically acceptable excipient. Acceptable excipients are non-toxic, aid administration, and do not adversely affect the therapeutic benefit of the compound of formula (I). Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this disclosure in aerosol form. Inert gases suitable for this purpose are nitrogen, carbon dioxide, etc.

Other suitable pharmaceutical excipients and their formulations are described in Remington's Pharmaceutical Sciences, edited by E. W. Martin (Mack Publishing Company, 20th ed., 2000).

The level of the compound in a formulation can vary within the full range employed by those skilled in the art. Typically, the formulation will contain, on a weight percent (wt %)

basis, from about 0.01-99.99 wt % of a compound of formula (I) based on the total formulation, with the balance being one or more suitable pharmaceutical excipients. Preferably, the compound is present at a level of about 1-80 wt %.

The compounds of the present disclosure may be used in combination with one or more other drugs in the treatment of diseases or conditions for which compounds of the present disclosure or the other drugs may have utility, where the combination of the drugs together are safer or more effective than either drug alone. Such other drug(s) may be administered, by a route and in an amount commonly used therefore, contemporaneously or sequentially with a compound of the present disclosure. When a compound of the present disclosure is used contemporaneously with one or more other drugs, a pharmaceutical composition in unit dosage form containing such other drugs and the compound of the present disclosure is preferred. However, the combination therapy may also include therapies in which the compound of the present disclosure and one or more other drugs are administered on different overlapping schedules. It is also contemplated that when used in combination with one or more other active ingredients, the compounds of the present disclosure and the other active ingredients may be used in lower doses than when each is used singly.

Accordingly, the pharmaceutical compositions of the present disclosure also include those that contain one or more other active ingredients, in addition to a compound of the present disclosure.

The above combinations include combinations of a compound of the present disclosure not only with one other active compound, but also with two or more other active compounds. Likewise, compounds of the present disclosure may be used in combination with other drugs that are used in the prevention, treatment, control, amelioration, or reduction of risk of the diseases or conditions for which compounds of the present disclosure are useful. Such other drugs may be administered, by a route and in an amount commonly used therefore, contemporaneously or sequentially with a compound of the present disclosure. When a compound of the present disclosure is used contemporaneously with one or more other drugs, a pharmaceutical composition containing such other drugs in addition to the compound of the present disclosure is preferred. Accordingly, the pharmaceutical compositions of the present disclosure also include those that also contain one or more other active ingredients, in addition to a compound of the present disclosure. The weight ratio of the compound of the present disclosure to the second active ingredient may be varied and will depend upon the effective dose of each ingredient. Generally, an effective dose of each will be used.

Where the subject is suffering from or at risk of suffering from an autoimmune disease, an inflammatory disease, or an allergy disease, a compound of Formula (I) can be used in with one or more of the following therapeutic agents in any combination: immunosuppressants (e.g., tacrolimus, cyclosporin, rapamicin, methotrexate, cyclophosphamide, azathioprine, mercaptopurine, mycophenolate, or FTY720), glucocorticoids (e.g., prednisone, cortisone acetate, prednisolone, methylprednisolone, dexamethasone, betamethasone, triamcinolone, beclometasone, fludrocortisone acetate, deoxycorticosterone acetate, aldosterone), non-steroidal anti-inflammatory drugs (e.g., salicylates, arylalkanoic acids, 2-arylpropionic acids, N-arylanthranilic acids, oxicams, coxibs, or sulphonanilides), Cox-2-specific inhibitors (e.g., valdecoxib, celecoxib, or rofecoxib), leflunomide, gold thioglucose, gold thiomalate, aurofin, sulfasalazine, hydroxychloroquinine, minocycline, TNF-.alpha. binding proteins (e.g., infliximab, etanercept, or adalimumab), abatacept, anakinra, interferon-.beta., interferon-.gamma., interleukin-2, allergy vaccines, antihistamines, antileukotrienes, beta-agonists, theophylline, or anticholinergics.

Where the subject is suffering from or at risk of suffering from a B-cell proliferative disorder (e.g., plasma cell myeloma), the subject can be treated with a compound of Formula (I) in any combination with one or more other anti-cancer agents. In some embodiments, one or more of the anti-cancer agents are proapoptotic agents. Examples of anti-cancer agents include, but are not limited to, any of the following: gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec™), geldanamycin, 17-N-Allylamino-17-Demethoxygeldanamycin (17-AAG), flavopiridol, LY294002, bortezomib, trastuzumab, BAY 11-7082, PKC412, or PD184352, Taxol™, also referred to as "paclitaxel", which is a well-known anti-cancer drug which acts by enhancing and stabilizing microtubule formation, and analogs of Taxol™., such as Taxotere™. Compounds that have the basic taxane skeleton as a common structure feature, have also been shown to have the ability to arrest cells in the G2-M phases due to stabilized microtubules and may be useful for treating cancer in combination with the compounds described herein.

Further examples of anti-cancer agents for use in combination with a compound of Formula (I) include inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; mTOR inhibitors; and antibodies (e.g., rituxan).

Other anti-cancer agents that can be employed in combination with a compound of Formula (I) include Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer, carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril;

mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer agents that can be employed in combination with a compound of Formula (I) include: 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor, carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; fmasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor, leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; R.sub.11 retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur, tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor, translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor, urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Yet other anticancer agents that can be employed in combination with a compound of Formula (I) include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, etc.), or triazenes (decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

Examples of natural products useful in combination with a compound of Formula (I) include but are not limited to vinca alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents that can be employed in combination a compound of Formula (I) include, but are not limited to, nitrogen mustards (e.g., mechloroethamine, cyclophosphamide, chlorambucil, melphalan, etc.), ethylenimine and methylmelamines (e.g., hexamethlymelamine, thiotepa), alkyl sulfonates (e.g., busulfan), nitrosoureas (e.g., carmustine, lomusitne, semustine, streptozocin, etc.), or triazenes (decarbazine, etc.). Examples of antimetabolites include, but are not limited to folic acid analog (e.g., methotrexate), or pyrimidine analogs (e.g., fluorouracil, floxuridine, Cytarabine), purine analogs (e.g., mercaptopurine, thioguanine, pentostatin.

Examples of hormones and antagonists useful in combination a compound of Formula (I) include, but are not limited to, adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide). Other agents that can be used in the methods and compositions described herein for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Examples of anti-cancer agents which act by arresting cells in the G2-M phases due to stabilized microtubules and which can be used in combination with an irreversible Btk inhibitor compound include without limitation the following marketed drugs and drugs in development Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HCl), AC-7700 (Ajinomoto, also known as AVE-8062, AVE-8062A, CS-39-L-Ser-.HCl, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B. Laulimalide, SPA-2 (Parker Hughes Institute), SPA-1 (Parker Hughes Institute, also known as SPIKET-P), 3-IAABU (Cytoskelcton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, Inanocine (also known as NSC-698666), 3-1AABE (Cytoskeleton/Mt. Sinai School of Medicine), A-204197 (Abbott), T-607 (Tuiarlk, also known as T-900607), RPR-15781 (Aventis), Eleutherobins (such as Desmethyleleutherobin, Desactyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCl), Resverastatin phosphate sodium, BPR-OY-007 (National Health Research Institutes), and SSR-250411 (Sanofi).

Where the subject is suffering from or at risk of suffering from a thromboembolic disorder (e.g., stroke), the subject can be treated with a compound of Formula (I) in any combination with one or more other anti-thromboembolic agents. Examples of anti-thromboembolic agents include, but are not limited any of the following: thrombolytic agents (e.g., alteplase anistreplase, streptokinase, urokinase, or tissue plasminogen activator), heparin, tinzaparin, warfarin, dabigatran (e.g., dabigatran etexilate), factor Xa inhibitors (e.g., fondaparinux, draparinux, rivaroxaban, DX-9065a, otamixaban, LY517717, or YM150), ticlopidine, clopidogrel, CS-747 (prasugrel, LY640315), ximelagatran, or BIBR 1048.

SYNTHETIC EXAMPLES

The following preparations of compounds of Formula (I) and intermediates (References) are given to enable those skilled in the art to more clearly understand and to practice the present disclosure. They should not be considered as limiting the scope of the disclosure, but merely as being illustrative and representative thereof.

Reference A

Synthesis of (R)-3-(4-phenoxyphenyl)-1-(piperidin-3-yl)-1H-pyrazolo[3,4d]pyrimidin-4-amine

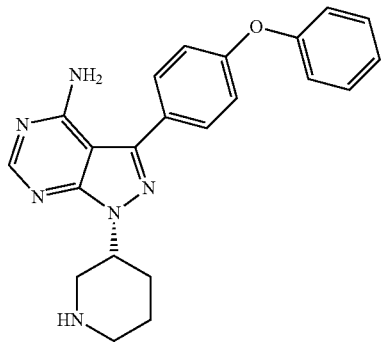

Step 1
A solution of 5-amino-1H-pyrazole-4-carbonitrile (10 g, 92.51 mmol, 1.00 equiv) in formamide (80 mL) was stirred under nitrogen at 165° C. for 5 h. The reaction mixture was cooled to room temperature and the solid was collected by filtration. The filter cake was washed first with 20 mL of water then 20 mL of methanol and dried to yield 9.5 g (76%) of 1H-pyrazolo[3,4-d]pyrimidin-4-amine as a white solid.
Step 2
A mixture of 1H-pyrazolo[3,4-d]pyrimidin-4-amine (150 g, 1.11 mol, 1.00 equiv) and N-iodo-succinimide (375 g, 1.67 mol, 1.58 equiv) in N,N-dimethylformamide (2.5 L) was stirred at 80° C. for 5 h. The reaction mixture was cooled to room temperature and then diluted with 10 L of water. The solid was collected by filtration, washed with 2×1 L of saturated aqueous sodium sulfite and dried under vacuum to give 150 g (52%) of 3-iodo-1H-pyrazolo[3,4-d]pyrimidin-4-amine as a yellow solid.
Step 3
To a stirred mixture of 3-iodo-1H-pyrazolo[3,4-d]pyrimidin-4-amine (5.9 g, 22.6 mmol, 1.00 equiv), (S)-tert-butyl 3-hydroxypiperidine-1-carboxylate (10 g, 50 mmol, 2.2 equiv) and triphenylphosphine (11.8 g, 45 mmol, 2.0 equiv) in tetrahydrofuran (300 mL) at 10° C. was added a solution of diisopropyl azodicarboxylate in tetrahydrofuran (30 mL) dropwise in 30 min. The resulting mixture was stirred at room temperature for 12 h and then concentrated under vacuum. The residue was purified on a silica gel column eluted with dichloromethane/methanol (100/1) to give 3 g (33%) of (R)-tert-butyl 3-(4-amino-3-iodo-1H-pyrazolo[3,4-d]pyrimidin-1-yl)piperidine-1-carboxylate as a yellow solid.
Step 4
A mixture of (R)-tert-butyl 3-[4-amino-3-iodo-1H-pyrazolo[3,4-d]pyrimidin-1-yl]piperidine-1-carboxylate (1 g, 2.25 mmol, 1.00 equiv), (4-phenoxyphenyl)boronic acid (530 mg, 2.48 mmol, 1.10 equiv), sodium carbonate (480 mg, 4.53 mmol, 2.01 equiv) and tetrakis(triphenylphosphine)palladium (78 mg, 0.07 mmol, 0.03 equiv) in 1,4-dioxane (60 mL) and water (15 mL) was stirred under nitrogen at 90° C. for 24 h. The reaction mixture was cooled to room temperature and then concentrated under vacuum. The residue was dissolved in 500 mL of dichloromethane. The resulting solution was washed with 200 mL of water, dried over anhydrous sodium sulfate and concentrated under vacuum. The residue was purified on a silica gel column eluted with dichloromethane/methanol (100/1) to give 700 mg (64%) of (R)-tert-butyl 3-[4-amino-3-(4-phenoxyphenyl)-1H-pyrazolo[3,4-d]pyrimidin-1-yl]piperidine-1-carboxylate as a yellow solid.
Step 5
A mixture of (R)-tert-butyl 3-[4-amino-3-(4-phenoxyphenyl)-1H-pyrazolo[3,4-d]pyrimidin-1-yl]piperidine-1-carboxylate (700 mg, 1.44 mmol, 1.00 equiv) in dichloromethane (100 mL) and trifluoroacetic acid (20 mL) was stirred at room temperature for 12 h. The reaction mixture was concentrated under vacuum to yield 580 mg of crude (R)-3-(4-phenoxyphenyl)-1-(piperidin-3-yl)-1H-pyrazolo[3,4-d]pyrimidin-4-amine as a yellow oil.

Reference B

Synthesis of (R)-3-(4-(3,4-dichlorophenoxy)-3-methoxyphenyl)-1-(piperidin-3-yl)-1H-pyrazolo[3,4-d]pyrimidin-4-amine

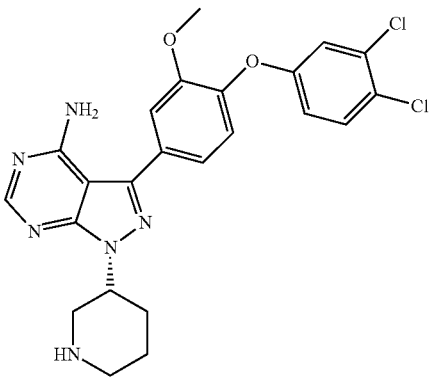

Step 1
A mixture of 3,4-dichlorophenol (38 g, 233.13 mmol, 1.00 equiv), 1-fluoro-2-methoxy-4-nitrobenzene (40 g, 233.75 mmol, 1.00 equiv) and potassium carbonate (64 g, 463.77 mmol, 1.99 equiv) in N,N-dimethylformamide (250 mL) was stirred overnight at 60° C. The resulting solution was diluted with 1000 mL of water, extracted with 3×200 mL of ethyl acetate and the organic layers combined. The resulting mixture was washed with 3×500 mL of brine. The mixture was dried over anhydrous sodium sulfate and concentrated under vacuum to yield 60 g (82%) of 1,2-dichloro-4-(2-methoxy-4-nitrophenoxy)benzene as a brown solid.

Step 2

A mixture of 1,2-dichloro-4-(2-methoxy-4-nitrophenoxy)benzene (60 g, 190.40 mmol, 1.00 equiv), Fe (53 g, 946.43 mmol, 4.97 equiv) and ammonium chloride (10 g, 188.68 mmol, 0.99 equiv) in tetrahydrofuran/water (1/2) (600 mL) was stirred overnight at 60° C. under an inert atmosphere of nitrogen. The mixture was filtered through Celite and the filtrate was concentrated under vacuum. The resulting solution was extracted with dichloromethane and the organic layers combined. The resulting mixture was washed with 3×500 mL of brine. The mixture was dried over anhydrous magnesium sulfate and concentrated under vacuum to give 40 g (74%) of 4-(3,4-dichlorophenoxy)-3-methoxyaniline as a light gray solid.

Step 3

A solution of sodium nitrite (14.4 g, 208.70 mmol, 1.98 equiv) in water (500 mL) was added dropwise into a solution of 4-(3,4-dichlorophenoxy)-3-methoxyaniline (30 g, 105.58 mmol, 1.00 equiv) in sulfuric acid (1000 mL) with stirring at 0° C. and the mixture was stirred for 30 min at 0° C. The above mixture was added dropwise to a solution of potassium iodide (1000 mL, 5%) in water with stirring at 50° C. The reaction was completed immediately. The reaction mixture was cooled to room temperature, extracted with ethyl acetate and the organic layers combined. The resulting mixture was washed with saturated aqueous sodium bicarbonate and brine. The mixture was dried over anhydrous sodium sulfate and concentrated under vacuum to give 24 g (crude) of 1,2-dichloro-4-(4-iodo-2-methoxyphenoxy)benzene as a red oil.

Step 4

A mixture of 1,2-dichloro-4-(4-iodo-2-methoxyphenoxy)benzene (93 g, 235.43 mmol, 1.00 equiv) in 1,4-dioxane (500 mL), potassium acetate (46 g, 469.39 mmol, 1.99 equiv), 4,4,5,5-tetramethyl-2-(4,4,5,5-tetramethyl-1,3,2-dioxaborolan-2-yl)-1,3,2-dioxaborolane (89 g, 350.39 mmol, 1.49 equiv) and Pd(dppf)Cl$_2$ (4.65 g) was stirred overnight at 90° C. under an inert atmosphere of nitrogen. The reaction mixture was cooled to room temperature and concentrated under vacuum. The residue was dissolved in 500 mL of ethyl acetate and washed with mL of water and brine. The mixture was dried over anhydrous sodium sulfate and concentrated under vacuum. The residue was applied onto a silica gel column with ethyl acetate/petroleum ether (1/100) to yield 10 g (11%) of 2-[4-(3,4-dichlorophenoxy)-3-methoxyphenyl]-4,4,5,5-tetramethyl-1,3,2-dioxaborolane as a light yellow oil.

2-[4-(3,4-Dichlorophenoxy)-3-methoxyphenyl]-4,4,5,5-tetramethyl-1,3,2-dioxaborolane was then covered to the title compound following the procedures described in Example 1, steps 4 and 5 above.

Reference C

Synthesis of 3-(4-phenoxyphenyl)-1-(pyrrolidin-2-ylmethyl)-1H-pyrazolo[3,4-d]pyrimidin-4-amine

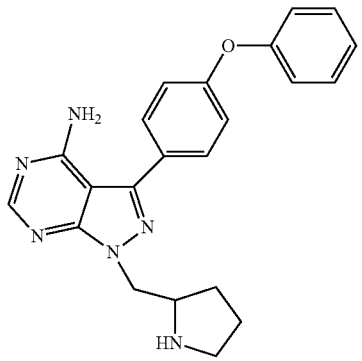 [SMILES: Nc1ncnc2c1c(-c1ccc(Oc3ccccc3)cc1)nn2CC1CCCN1]

Synthesized as described in Reference A above but using tert-butyl 2-(hydroxymethyl)-pyrrolidine-1-carboxylate instead of (S)-tert-butyl-3-hydroxypiperidine-1-carboxylate. MS (ESI, pos. ion) m/z: 522 (M+1).

Reference D

Synthesis of 1-((1r,4r)-4-aminocyclohexyl)-3-(4-phenoxyphenyl)-1H-pyrazolo[3,4-d]pyrimidin-4-amine

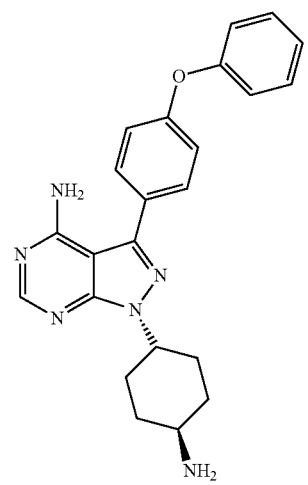

Synthesized as described in Reference A above except using tert-butyl(1r,4r)-4-hydroxycyclohexylcarbamate instead of (S)-tert-butyl 3-hydroxypiperidine-1-carboxylate.

Reference E

Synthesis of 4-(4-phenoxyphenyl)-1-(piperidin-4-yl)-1H-pyrazolo[3,4-d]pyrimidin-4-amine

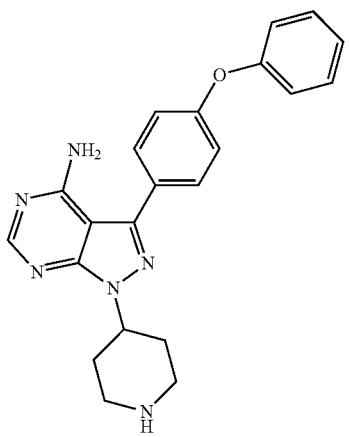 [SMILES: Nc1ncnc2c1c(-c1ccc(Oc3ccccc3)cc1)nn2C1CCNCC1]

Synthesized as described in Reference A above except using, tert-butyl-4-hydroxypiperidine-1-carboxylate instead

Reference F

Synthesis of (R)-N-(4-(4-amino-1-(piperidin-3-yl)-1H-pyrazolo[3,4-d]pyrimidin-3-yl)phenyl)-4-(trifluoromethyl)benzamide

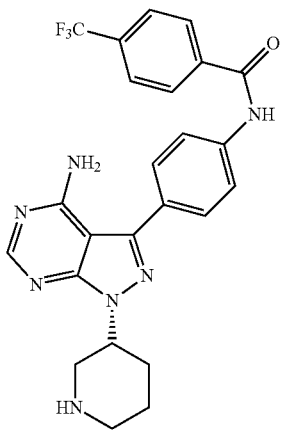

Step 1

A mixture of 3-iodo-1H-pyrazolo[3,4-d]pyrimidin-4-amine (5.9 g, 22.6 mmol, 1.00 equiv), (S)-tert-butyl3-hydroxypiperidine-1-carboxylate (10 g, 50 mmol, 2.2 equiv), triphenylphosphine (11.8 g, 45 mmol, 2 equiv) in tetrahydrofuran (300 mL) was stirred at 10° C. Diisopropyl azodicarboxylate in tetrahydrofuran (30 mL) was dropped in the mixture slowly in 30 min. The resulting mixture was stirred for 12 h at room temperature was and then concentrated under vacuum. The residue was loaded onto a silica gel column and eluted with dichloromethane/methanol (100/1) to give 3 g (33%) of (R)-tert-butyl 3-(4-amino-3-iodo-1H-pyrazolo[3,4-d]pyrimidin-1-yl)piperidine-1-carboxylate as yellow solid.

Step 2

Into a 250-mL 3-necked round-bottom flask purged and maintained with an inert atmosphere of nitrogen, was placed (R)-tert-butyl 3-[4-amino-3-iodo-1H-pyrazolo[3,4-d]pyrimidin-1-yl]piperidine-1-carboxylate (2 g, 4.50 mmol, 1.00 equiv), 4-borono-benzenaminium chloride (0.934 g), Pd(PPh$_3$)$_4$ (0.312 g), ethylene glycol dimethyl ether (100 mL), sodium carbonate (1.194 g), and water (20 mL). The resulting solution was stirred for 12 h at 80° C. in an oil bath. The resulting mixture was concentrated under vacuum and residue was loaded onto a silica gel column and eluted with dichloromethane/methanol (50:1) to give 1.5 g (81%) of (R)-tert-butyl 3-(4-amino-3-(4-aminophenyl)-1H-pyrazolo[3,4-d]pyrimidin-1-yl)piperidine-1-carboxylate as a brown solid.

Step 3

Into a 250-mL round-bottom flask, was placed (R)-tert-butyl 3-[4-amino-3-(4-aminophenyl)-1H-pyrazolo[3,4-d]pyrimidin-1-yl]piperidine-1-carboxylate (1.0 g, 2.44 mmol, 1.00 equiv), HATU (0.746 g), 4-(trifluoromethyl)benzoic acid (374 mg, 1.97 mmol, 0.81 equiv), triethylamine (500 mg, 4.94 mmol, 2.02 equiv), and N,N-dimethylformamide (50 mL). The resulting solution was stirred for 5 h at 25° C. The resulting mixture was quenched with water. The resulting solution was extracted with ethyl acetate and washed with sodium chloride (sat). The organic layers dried over anhydrous magnesium sulfate and concentrated under vacuum and the residue was loaded onto a silica gel column and eluted with dichloromethane/methanol (50:1 to give 1.15 g (81%) of tert-butyl 3-[4-amino-3-(4-[[4-(trifluoromethyl)benzene]amido]phenyl)-1H-pyrazolo[3,4-d]pyrimidin-1-yl]piperidine-1-carboxylate as a brown solid.

Step 4

Into a 250-mL round-bottom flask, was placed (R)-tert-butyl 3-[4-amino-3-(4-[[4-(trifluoromethyl)benzene]amido]phenyl)-1H-pyrazolo[3,4-d]pyrimidin-1-yl]piperidine-1-carboxylate (1.1 g, 1.89 mmol, 1.00 equiv), and dichloromethane (100 mL). This was followed by the addition of CF$_3$COOH (20 mL) dropwise with stirring at 25° C. over 10 min. The resulting solution was stirred for 3 h at 25° C. The resulting mixture was concentrated under vacuum to give 0.829 g (91%) of (R)-N-[4-[4-amino-1-(piperidin-3-yl)-1H-pyrazolo[3,4-d]pyrimidin-3-yl]phenyl]-4-(trifluoromethyl)benzamide as a brown oil. MS (ESI, pos. ion) m/z: 382 (M+1)

Reference G

Synthesis of 3-[4-(3-fluorophenoxy)phenyl]-1-[(2R)-pyrrolidin-2-ylmethyl]-1H-pyrazolo[3,4-d]pyrimidin-4-amine

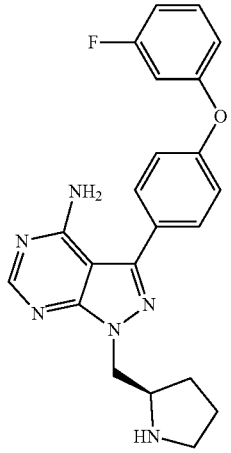 [SMILES: Nc1ncnc2c1c(-c1ccc(Oc3cccc(F)c3)cc1)nn2C[C@H]1CCCN1]

Step 1

Into a 100-mL 3-necked round-bottom flask purged and maintained under an inert atmosphere of nitrogen, was placed tert-butyl (2R)-2-([4-amino-3-iodo-1H-pyrazolo[3,4-d]pyrimidin-1-yl]methyl)pyrrolidine-1-carboxylate (300 mg, 0.68 mmol, 1.00 equiv), prepared as described in Example 1 except in the Mitsunobu reaction using (R)-tert-butyl 2-(hydroxymethyl)pyrrolidine-1-carboxylate instead of (S)-tert-butyl 3-hydroxypiperidine-1-carboxylate, 2-[4-(3-fluorophenoxy)phenyl]-4,4,5,5-tetramethyl-1,3,2-dioxaborolane (254 mg, 0.81 mmol, 1.20 equiv), tetrakis(triphenylphosphane) palladium (47 mg, 0.04 mmol, 0.06 equiv), ethylene glycol dimethyl ether (50 mL), sodium carbonate (180 mg, 1.70 mmol, 2.50 equiv), water (10 mL). The resulting solution was stirred for 12 h at 80° C. in an oil bath. The resulting mixture was concentrated under vacuum. The resulting solution was extracted with dichloromethane and the organic layers combined, dried and concentrated under vacuum. The residue was loaded on a silica gel column and eluted with dichloromethane/methanol (50/1) to give 0.27 g (79%) of tert-butyl (2R)-2-([4-amino-3-[4-(3-fluorophenoxy)phenyl]-1H-pyrazolo[3,4-d]pyrimidin-1-yl]methyl)pyrrolidine-1-carboxylate as a brown solid.

Step 2

Into a 100-mL round-bottom flask, was placed a solution of tert-butyl (2R)-2-([4-amino-3-[4-(3-fluorophenoxy)phenyl]-1H-pyrazolo[3,4-d]pyrimidin-1-yl]methyl)pyrrolidine-1-carboxylate (270 mg, 0.54 mmol, 1.00 equiv) in dichloromethane (50 mL). This was followed by the addition of trifluoroacetic acid (10 mL) dropwise with stirring over 10 min. The resulting solution was stirred for 3 h at 25° C. The resulting mixture was concentrated under vacuum to give 0.216 g (crude) of 3-[4-(3-fluorophenoxy)phenyl]-1-[(2R)-pyrrolidin-2-ylmethyl]-1H-pyrazolo[3,4-d]pyrimidin-4-amine as a brown oil.

Reference H

Synthesis of 3-[4-(2,6-difluorophenoxy)phenyl]-1-[(2R)-pyrrolidin-2-ylmethyl]-1H-pyrazolo[3,4-d]pyrimidin-4-amine

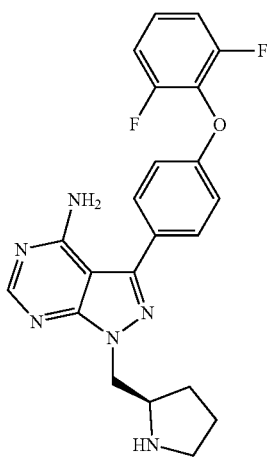 [SMILES: Nc1ncnc2c1c(-c1ccc(Oc3c(F)cccc3F)cc1)nn2C[C@H]1CCCN1]

Step 1

Into a 1000-mL, 2-necked round-bottom flask purged and maintained under an inert atmosphere of nitrogen, was placed 3-iodo-1H-pyrazolo[3,4-d]pyrimidin-4-amine (10 g, 38.31 mmol, 1.00 equiv), tert-butyl (2R)-2-(hydroxymethyl)pyrrolidine-1-carboxylate (15.4 g, 76.52 mmol, 2.00 equiv), $PPh_3$ (20.1 g, 76.63 mmol, 2.00 equiv), and N,N-dimethylformamide (400 mL). DIAD (15.5 g, 76.65 mmol, 2.00 equiv) was added dropwise over 30 min. The resulting solution was stirred for 12 h at 25° C. and then diluted with 1 L of water. The resulting solution was extracted with ethyl acetate and the organic layers combined and washed with brine. The mixture was dried over anhydrous sodium sulfate and concentrated under vacuum and the residue was placed on a silica gel column and eluted with chloroform/methanol (100/1) to give 1.2 g (6%) of tert-butyl (2R)-2-([4-amino-3-iodo-1H-pyrazolo[3,4-d]pyrimidin-1-yl]methyl)pyrrolidine-1-carboxylate as an off-white solid.

Step 2

Into a 500-mL 4-necked round-bottom flask, was placed a solution of sodium hydride (4.05 g, 168.75 mmol, 1.70 equiv) in N,N-dimethylformamide (200 mL). A solution of 1-fluoro-4-nitrobenzene (14 g, 99.22 mmol, 1.00 equiv) in N,N-dimethylformamide (50 mL) dropwise with stirring at 0° C. over 20 min. The resulting solution was stirred for 2 hr at room temperature. $Cu_2Cl_2$ (9.83 g, 100.31 mmol, 1.01 equiv) was added and a solution of 2,6-difluorophenol (15.5 g, 119.15 mmol, 1.20 equiv) in N,N-dimethylformamide (50 mL) was added dropwise with stirring at 25° C. over 10 min. The resulting solution was stirred for 12 h at 100° C. in an oil bath, diluted with 500 mL of water and extracted with ethyl acetate. The combined organic layers were washed with water and brine, dried over anhydrous sodium sulfate and concentrated under vacuum. The residue was placed on a silica gel column and eluted with ethyl acetate/petroleum ether (1/8) to give 20 g (80%) of 1,3-difluoro-2-(4-nitrophenoxy)benzene as a brown oil.

Step 3

Into a 500 mL, 3-necked round-bottom flask purged and maintained under an inert atmosphere of nitrogen, was placed a solution of 1,3-difluoro-2-(4-nitrophenoxy)benzene (20 g, 79.62 mmol, 1.00 equiv) in methanol (200 mL), Raney Nickel (2 g). A solution of hydrazine hydrate (12.67 g) in methanol (50 mL) was added dropwise with stirring in 15 min. The resulting solution was stirred for 12 h at 25° C., then filtrated and the filtrate was concentrated under vacuum. The residue was diluted with 200 mL of ethyl acetate, washed with water and brine, and dried over anhydrous sodium sulfate and concentrated under vacuum to give 16 g (91%) of 4-(2,6-difluorophenoxy)aniline as a black oil.

Step 4

Into a 250-mL 4-necked round-bottom flask, was placed 4-(2,6-difluorophenoxy)-aniline (8.84 g, 39.96 mmol, 1.00 equiv), hydrogen chloride (37%) (10.14 g, 277.81 mmol, 6.95 equiv) and water (20 mL). $NaNO_2$ (3.04 g, 44.06 mmol, 1.10 equiv) in water (10 mL) was added dropwise with stirring at 0° C. over 5 min., and the reaction mixture was stirred for 30 mins at 0° C. The reaction mixture was added into a solution of NaI (18 g, 120.00 mmol, 3.00 equiv) in water (20 mL) at 25° C. in batches over 5 min. The resulting solution was stirred for 2 h at 25° C. and then extracted with of ethyl acetate and the organic layers were combined. The combined organic layers were washed with water and brine, dried over anhydrous sodium sulfate and concentrated under vacuum to give 10.2 g (77%) of 1,3-difluoro-2-(4-iodophenoxy)benzene as a brown oil.

Step 5

Into a 100 mL 3-necked round-bottom flask purged and maintained in an inert atmosphere of nitrogen, was placed a solution of 1,3-difluoro-2-(4-iodophenoxy)benzene (2 g, 6.02 mmol, 1.00 equiv) in N,N-dimethylformamide (50 mL), 4,4,5,5-tetramethyl-2-(tetramethyl-1,3,2-dioxaborolan-2-yl)-1,3,2-dioxaborolane (1.68 g, 6.62 mmol, 1.10 equiv), potassium acetate (1.76 g, 17.93 mmol, 3.0 equiv), and $Pd(OAc)_2$ (68 mg, 0.30 mmol, 0.05 equiv). The resulting solution was stirred for 12 h at 85° C. in an oil bath. The reaction mixture was then quenched by the addition of 100 mL of water. The resulting solution was extracted with ethyl acetate and the organic layers combined and washed with water and brine. The organics were dried over anhydrous sodium sulfate and concentrated under vacuum. The residue was loaded onto a silica gel column and eluted with ethyl acetate/petroleum ether (1/8) to give 1.5 g (75%) of 2-[4-(2,6-difluorophenoxy)phenyl]-4,4,5,5-tetramethyl-1,3,2-dioxaborolane as a light yellow solid.

Step 6

Into a 100 mL, 3-necked round-bottom flask purged and maintained in an inert atmosphere of nitrogen, was placed a solution of tert-butyl (2R)-2-([4-amino-3-iodo-1H-pyrazolo[3,4-d]pyrimidin-1-yl]methyl)pyrrolidine-1-carboxylate (300 mg, 0.68 mmol, 1.00 equiv) in 1,4-dioxane/water (60/15 mL), 2-[4-(2,6-difluorophenoxy)phenyl]-4,4,5,5-tetramethyl-1,3,2-dioxaborolane (290 mg, 0.87 mmol, 1.3 equiv), sodium carbonate (180 mg, 1.68 mmol, 2.5 equiv), and tetrakis(triphenylphosphane)palladium (40 mg, 0.03 mmol, 0.05 equiv). The resulting solution was stirred for 12 h at 90° C. in an oil bath and then concentrated under vacuum. The resulting solution was diluted with 50 mL of dichloromethane, washed with water and brine. The organics were dried over anhydrous sodium sulfate and concentrated under vacuum. The residue was loaded onto a silica gel column and eluted with dichloromethane/methanol (20/1) to give 280 mg (79%) of tert-butyl (2R)-2-([4-amino-3-[4-(2,6-difluorophenoxy)phenyl]-1H-pyrazolo[3,4-d]pyrimidin-1-yl]methyl) pyrrolidine-1-carboxylate as a white solid.
Step 7

Into a 50 mL round-bottom flask, was placed a solution of tert-butyl (2R)-2-([4-amino-3-[4-(2,6-difluorophenoxy)phenyl]-1H-pyrazolo[3,4-d]pyrimidin-1-yl]methyl)-pyrrolidine-1-carboxylate (280 mg, 0.54 mmol, 1.00 equiv) in dichloromethane (10 mL). Trifluoroacetic acid (2 mg, 0.02 mmol, 0.03 equiv) was added dropwise with stirring at 25° C. The resulting solution was stirred for 3 h at 25° C. and then concentrated under vacuum. The resulting solution was diluted with 50 mL of dichloromethane, washed with ethyl acetate and H$_2$O, brine and concentrated under vacuum to give 200 mg (88%) of 3-[4-(2,6-difluorophenoxy)phenyl]-1-[(2R)-pyrrolidin-2-ylmethyl]-1H-pyrazolo[3,4-d]pyrimidin-4-amine as a white solid.

Reference I

Synthesis of 3-(2-fluoro-4-phenoxyphenyl)-1-[(2R)-pyrrolidin-2-ylmethyl]-1H-pyrazolo[3,4-d]pyrimidin-4-amine

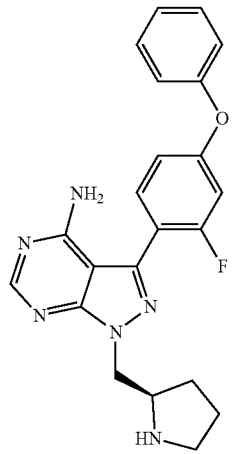 [SMILES: Nc1ncnc2c1c(-c1ccc(Oc3ccccc3)cc1F)nn2C[C@H]1CCCN1]

Step 1

Into a 250 mL round-bottom flask, was placed a solution of 4-bromo-3-fluorophenol (5 g, 26.18 mmol, 1.00 equiv) in dichloromethane (100 mL), phenylboronic acid (3.5 g, 28.70 mmol, 1.10 equiv), Cu(AcO) (5.7 g), triethylamine (5.3 g), and 4 A molecular sieves (15 g). The resulting solution was stirred overnight at room temperature. The solids were filtered out. The filtrate was dried over anhydrous sodium sulfate and concentrated under vacuum. The residue was loaded onto a silica gel column and eluted with ethyl acetate/petroleum ether (1:100-1:50). This resulted in 2 g (29%) of 1-bromo-2-fluoro-4-phenoxybenzene as a colorless oil.
Step 2

Into a 100 mL 3-necked round-bottom flask purged and maintained under an inert atmosphere of nitrogen, was placed a solution of 1-bromo-2-fluoro-4-phenoxybenzene (2 g, 7.49 mmol, 1.00 equiv) in tetrahydrofuran (20 mL). BuLi (1M) (8 mL) was added dropwise with stirring at −70 to −80° C. The resulting solution was stirred for 30 min at −70-80° C. in a liquid nitrogen bath. Tris(propan-2-yl)borate (1.7 g, 9.04 mmol, 1.21 equiv) was added dropwise with stirring at −70 to −80° C. The resulting solution was allowed to react, with stirring, for an additional 2 h while the temperature was maintained at −70 to −80° C. The reaction was then quenched by the addition of 100 mL of water, extracted with ethyl acetate and the organic layers were combined and dried over anhydrous sodium sulfate and concentrated under vacuum. The residue was loaded onto a silica gel column and eluted with ethyl acetate/petroleum ether (1:20) to give 1.6 g (92%) of (2-fluoro-4-phenoxyphenyl)-boronic acid as a white solid.
Step 3

Into a 100 mL, 3-necked round-bottom flask purged and maintained under an inert atmosphere of nitrogen, was placed tert-butyl (2R)-2-([4-amino-3-iodo-1H-pyrazolo[3,4-d]pyrimidin-1-yl]methyl)pyrrolidine-1-carboxylate (380 mg, 0.86 mmol, 1.00 equiv), (2-fluoro-4-phenoxyphenyl)boronic acid (240 mg, 1.03 mmol, 1.20 equiv), tetrakis-(triphenylphosphane) palladium (60 mg, 0.05 mmol, 0.06 equiv), dioxane (50 mL), sodium carbonate (228 mg, 2.15 mmol, 2.50 equiv) and water (10 mL). The resulting solution was stirred for 12 h at 80° C. in an oil bath. The resulting mixture was concentrated under vacuum and the resulting solution was extracted with dichloromethane and the organic layers combined, dried and concentrated under vacuum. The residue was loaded onto a silica gel column and eluted with dichloromethane/methanol (50/1) to give 0.347 g (80%) of tert-butyl (2R)-2-[[4-amino-3-(2-fluoro-4-phenoxyphenyl)-1H-pyrazolo[3,4-d]pyrimidin-1-yl]methyl]pyrrolidine-1-carboxylate as a brown solid.
Step 4

Into a 100 mL, round-bottom flask, was placed a solution of tert-butyl (2R)-2-[[4-amino-3-(2-fluoro-4-phenoxyphenyl)-1H-pyrazolo[3,4-d]pyrimidin-1-yl]methyl]pyrrolidine-1-carboxylate (347 mg, 0.69 mmol, 1.00 equiv) in dichloromethane (50 mL). Trifluoroacetic acid (10 mL) dropwise with stirring over 10 min and the resulting solution was stirred for 3 h at 25° C. The resulting mixture was concentrated under vacuum to give 0.278 g (crude) of 3-(2-fluoro-4-phenoxyphenyl)-1-[(2R)-pyrrolidin-2-ylmethyl]-1H-pyrazolo[3,4-d]pyrimidin-4-amine as brown oil.

Reference J

Synthesis of 3-[4-(2,3-difluorophenoxy)phenyl]-1-[(2R)-pyrrolidin-2-ylmethyl]-1H-pyrazolo[3,4-d]pyrimidin-4-amine bis(trifluoroacetic acid)

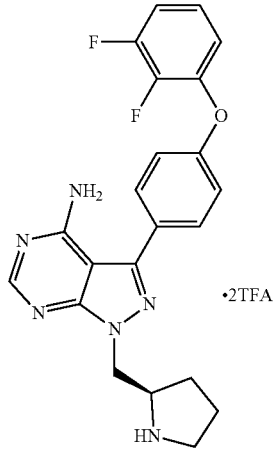 [SMILES: Nc1ncnc2c1c(-c1ccc(Oc3cccc(F)c3F)cc1)nn2C[C@H]1CCCN1]

Step 1

Into a 500 mL round-bottom flask, was placed a solution of (2,3-difluorophenyl)-boronic acid (30 g, 189.98 mmol, 1.00 equiv) in dichloromethane (250 mL). $H_2O_2$ (30 mL) was added dropwise with stirring. The resulting solution was stirred for 2 h at 25° C. The resulting mixture was washed with water and brine, dried over anhydrous magnesium sulfate and concentrated under vacuum to give 23 g (93%) of 2,3-difluorophenol as a brown oil.

Step 2

Into a 500 mL, 4-necked round-bottom flask purged and maintained under an inert atmosphere of nitrogen, was placed a solution of sodium hydride (6.8 g, 170.00 mmol, 1.70 equiv, 60%) in N,N-dimethylformamide (200 mL). A solution of 1-fluoro-4-nitrobenzene (14.1 g, 99.93 mmol, 1.00 equiv) in N,N-dimethylformamide (50 mL) was added dropwise with stirring at 0° C. in 15 min. The resulting solution was stirred for 2 h at room temperature. CuCl (10 g, 101.01 mmol, 1.00 equiv) was added and a solution of 2,3-difluorophenol (15.6 g, 119.91 mmol, 1.20 equiv) in N,N-dimethylformamide (50 mL) was added dropwise with stirring. The resulting solution was allowed to react, with stirring, for an additional 12 h while the temperature was maintained at 100° C. in an oil bath. The resulting solution was extracted with ether and the organic layers combined. The organic layers was washed with water and brine, dried over anhydrous sodium sulfate and concentrated under vacuum. The residue was loaded onto a silica gel column and eluted with ethyl acetate/petroleum ether (1:8) to give 21.2 g (84%) of 1,2-difluoro-3-(4-nitrophenoxy)benzene as a brown solid.

Step 3

Into a 500 mL, 3-necked round-bottom flask purged and maintained under an inert atmosphere of nitrogen, was placed a solution of 1,2-difluoro-3-(4-nitrophenoxy)benzene (21.2 g, 84.40 mmol, 1.00 equiv) in methanol (200 mL), and Raney Nickel (2 g). A solution of hydrazine hydrate (12.67 g, 3.00 equiv) in methanol (50 mL) was added dropwise with stirring in 15 min. The resulting solution was stirred for 12 h at 25° C. The solids were filtered out and the filtrate was concentrated under vacuum. The residue was diluted with 200 mL of ethyl acetate and washed with water and brine, dried over anhydrous sodium sulfate and concentrated under vacuum to give 16.3 g (87%) of 4-(2,3-difluorophenoxy)aniline as a black oil.

Step 4

Into a 250-mL 4-necked round-bottom flask, was placed 4-(2,3-difluorophenoxy)-aniline (8.84 g, 39.96 mmol, 1.00 equiv), hydrogen chloride (10.14 g, 100.01 mmol, 2.50 equiv), and water (20 mL). A solution of $NaNO_2$ (3.04 g, 44.06 mmol, 1.10 equiv) in water (10 mL) was added dropwise with stirring in portions at 0° C. The mixture was stirred at 0° C. for half an hour. To this was added urea (1 g, 16.65 mmol). The mixture was stirred at 0° C. for 20 min and poured into the solution of NaI (18 g, 120.00 mmol, 3.00 equiv) in water (20 mL) at room temperature. The resulting solution was stirred at room temperature for 1 h and then extracted with ethyl acetate. The organic layers combined and dried over anhydrous sodium sulfate and concentrated under vacuum to give 10.5 g (79%) of 1,2-difluoro-3-(4-iodophenoxy)benzene as a brown oil.

Step 5

Into a 100 mL, 3-necked round-bottom flask purged and maintained under an inert atmosphere of nitrogen, was placed a solution of 1,2-difluoro-3-(4-iodophenoxy)benzene (2 g, 6.02 mmol, 1.00 equiv) in N,N-dimethylformamide (50 mL), 4,4,5,5-tetramethyl-2-(tetramethyl-1,3,2-dioxaborolan-2-yl)-1,3,2-dioxaborolane (1.68 g, 6.62 mmol, 1.10 equiv), potassium acetate (68 mg, 0.69 mmol, 0.05 equiv), and Pd(OAC)$_2$ (1.76 g, 7.84 mmol, 3.00 equiv). The resulting solution was stirred for 12 h at 85° C. in an oil bath. The reaction was then diluted with 100 mL of water, extracted with ethyl acetate and the organic layers combined. The organics were washed with water and brine, dried over anhydrous sodium sulfate and concentrated under vacuum. The residue was loaded onto a silica gel column and eluted with ethyl acetate/petroleum ether (1/8) to give 1.5 g (75%) of 2-[4-(2,3-difluorophenoxy)phenyl]-4,4,5,5-tetramethyl-1,3,2-dioxaborolane as a light yellow solid.

Step 6

Into a 100 mL, 3-necked round-bottom flask purged and maintained under an inert atmosphere of nitrogen, was placed tert-butyl (2R)-2-([4-amino-3-iodo-1H-pyrazolo[3,4-d]pyrimidin-1-yl]methyl)pyrrolidine-1-carboxylate (300 mg, 0.68 mmol, 1.00 equiv), a solution of 2-[4-(2,3-difluorophenoxy)phenyl]-4,4,5,5-tetramethyl-1,3,2-dioxaborolane (290 mg, 0.87 mmol, 1.10 equiv) in Dioxane (9 mL), tetrakis(triphenylphosphane)palladium (40 mg, 0.03 mmol, 0.05 equiv), and a solution of sodium carbonate (179 mg, 1.67 mmol, 2.50 equiv) in water (3 mL). The resulting solution was stirred for 12 h at 100° C. in an oil bath. The resulting mixture was concentrated under vacuum, and the solution was diluted with 20 mL of ethyl acetate. The resulting mixture was washed with water and brine, dried over anhydrous sodium sulfate and concentrated under vacuum. The residue was loaded onto a silica gel column and eluted with dichloromethane/methanol (20/1) to give 250 mg (71%) of tert-butyl (2R)-2-([4-amino-3-[4-(2,3-difluorophenoxy)phenyl]-1H-pyrazolo[3,4-d]pyrimidin-1-yl]methyl)pyrrolidine-1-carboxylate as a white solid.

Step 7

Into a 100 mL, round-bottom flask, was placed a solution of tert-butyl (2R)-2-([4-amino-3-[4-(2,3-difluorophenoxy)phenyl]-1H-pyrazolo[3,4-d]pyrimidin-1-yl]methyl)-pyrrolidine-1-carboxylate (350 mg, 0.67 mmol, 1.00 equiv) in dichloromethane (10 mL). Trifluoroacetic acid (2 mL) dropwise with stirring and the resulting solution was stirred for 3 h at 25° C. The resulting mixture was concentrated under vacuum to give 200 mg (46%) of 3-[4-(2,3-difluorophenoxy)phenyl]-1-[(2R)-pyrrolidin-2-ylmethyl]-1H-pyrazolo[3,4-d]pyrimidin-4-amine bis(trifluoroacetic acid) salt as a brown solid.

Reference K

Synthesis of 3-[4-(3,5-difluorophenoxy)phenyl]-1-[(2R)-pyrrolidin-2-ylmethyl]-1H-pyrazolo[3,4-d]pyrimidin-4-amine

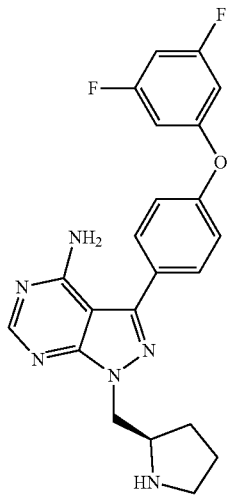 [SMILES: Nc1ncnc2c1c(-c1ccc(Oc3cc(F)cc(F)c3)cc1)nn2C[C@H]1CCCN1]

Step 1

Into a 250-mL round-bottom flask, was placed a solution of 4-(tetramethyl-1,3,2-dioxaborolan-2-yl)phenol (5 g, 22.72 mmol, 1.00 equiv) in dichloromethane (100 mL), (3,5-difluorophenyl)boronic acid (4 g, 25.33 mmol, 1.11 equiv), Cu(AcO)₂ (5 g), 4 A molecular sieves (15 g), triethylamine (4.6 g). The resulting solution was stirred for overnight at room temperature. The solids were filtered out. The filtrate was dried over anhydrous sodium sulfate and concentrated under vacuum. The residue was applied onto a silica gel column with ethyl acetate/petroleum ether (1:100-1:50). This resulted in 2 g (27%) of 2-[4-(3,5-difluorophenoxy)phenyl]-4,4,5,5-tetramethyl-1,3,2-dioxaborolane as a colorless oil.

Step 2

Into a 100 mL, 3-necked round-bottom flask purged and maintained with an inert atmosphere of nitrogen, was placed tert-butyl (2R)-2-([4-amino-3-iodo-1H-pyrazolo[3,4-d]pyrimidin-1-yl]methyl)pyrrolidine-1-carboxylate (250 mg, 0.56 mmol, 1.00 equiv), 2-[4-(3,5-difluorophenoxy)phenyl]-4,4,5,5-tetramethyl-1,3,2-dioxaborolane (226 mg, 0.68 mmol, 1.20 equiv), tetrakis(triphenylphosphane) palladium (39 mg, 0.03 mmol, 0.06 equiv), dioxane (50 mL), sodium carbonate (149 mg, 1.41 mmol, 2.50 equiv), and water (10 mL). The resulting solution was stirred for 12 h at 80° C. in an oil bath and then concentrated under vacuum. The resulting solution was extracted with dichloromethane and the organic layers combined, dried and concentrated under vacuum. The residue was loaded onto a silica gel column and eluted with dichloromethane/methanol (50/1) to give 0.237 g (81%) of tert-butyl (2R)-2-([4-amino-3-[4-(3,5-difluorophenoxy)phenyl]-1H-pyrazolo[3,4-d]pyrimidin-1-yl]methyl)pyrrolidine-1-carboxylate as a brown solid which was converted to title compound as described in Reference I above.

Reference L

Synthesis of 3-[4-(2-fluorophenoxy)phenyl]-1-(3-(R)-piperidin-3-yl)-1H-pyrazolo[3,4-d]-pyrimidin-4-amine

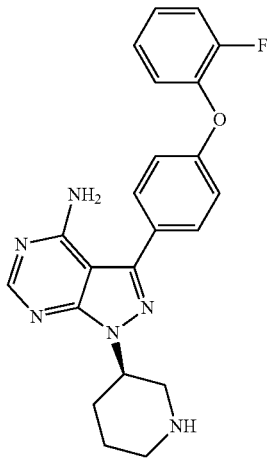 [SMILES: Nc1ncnc2c1c(-c1ccc(Oc3ccccc3F)cc1)nn2[C@@H]1CCCNC1]

Step 1

Into a 100 mL, 3-necked round-bottom flask purged and maintained with an inert atmosphere of nitrogen, was placed a solution of tert-butyl 3-[4-amino-3-iodo-1H-pyrazolo[3,4-d]pyrimidin-1-yl]piperidine-1-carboxylate (300 mg, 0.68 mmol, 1.00 equiv) in dioxane/H₂O(7/3=V/V) (30 mL), [4-(2-fluorophenoxy)phenyl]boronic acid (500 mg, 2.16 mmol, 6.99 equiv), sodium carbonate (200 mg, 1.89 mmol, 0.26 equiv), and Pd(PPh)₄ (500 mg, 0.43 mmol, 3.19 equiv). The resulting solution was stirred overnight at 100° C. in an oil bath an then concentrated under vacuum. The residue was loaded onto a silica gel column and eluted with dichloromethane/methanol (100:1) to give 0.2 g (59%) of tert-butyl 3-[4-amino-3-[4-(2-fluorophenoxy)phenyl]-1H-pyrazolo[3,4-d]pyrimidin-1-yl]piperidine-1-carboxylate as a light yellow solid.

Step 2

Into a 100 mL, round-bottom flask purged and maintained under an inert atmosphere of nitrogen, was placed a solution of tert-butyl 3-[4-amino-3-[4-(2-fluorophenoxy)phenyl]-1H-pyrazolo[3,4-d]pyrimidin-1-yl]piperidine-1-carboxylate (200 mg, 0.40 mmol, 1.00 equiv) in dichloromethane (20 mL), and trifluoroacetic acid (10 g, 87.70 mmol, 221.25 equiv). The resulting solution was stirred overnight at room temperature and then concentrated under vacuum. The pH value of the solution was adjusted to 8-10 with 10% aqueous sodium carbonate. The solution was extracted with dichloromethane and the organic layers were combined and dried over anhydrous sodium sulfate and concentrated under vacuum to give 0.1 g (62%) of 3-[4-(2-fluorophenoxy)phenyl]-1-(piperidin-3-yl)-1H-pyrazolo[3,4-d]pyrimidin-4-amine as a light yellow solid.

Reference M

Synthesis of 3-[4-(3-fluorophenoxy)phenyl]-1-[(3R)-piperidin-3-yl]-1H-pyrazolo[3,4-d]pyrimidin-4-amine

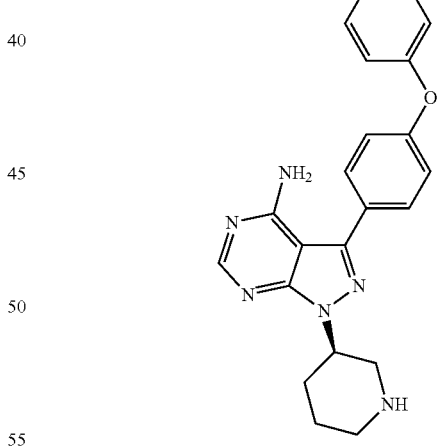

Step 1

Into a 250 mL round-bottom flask, was placed a solution of 4-(tetramethyl-1,3,2-dioxaborolan-2-yl)phenol (5 g, 22.72 mmol, 1.00 equiv) in dichloromethane (100 mL), (3-fluorophenyl)boronic acid (3.5 g, 25.01 mmol, 1.10 equiv), Cu(AcO)₂ (5 g), 4 A molecular sieves (15 g), and triethylamine (4.6 g). The resulting solution was stirred overnight at room temperature. The solids were filtered out and the filtrate was dried over anhydrous sodium sulfate and concentrated under vacuum. The residue was loaded onto a silica gel column and eluted with ethyl acetate/petroleum ether (1:100-1:

50) to give 1.8 g (25%) of 2-[4-(3-fluorophenoxy)phenyl]-4, 4,5,5-tetramethyl-1,3,2-dioxaborolane as a colorless oil.

Step 2

Into a 100 mL 3-necked round-bottom flask purged and maintained with an inert atmosphere of nitrogen, was placed tert-butyl (3R)-3-[4-amino-3-iodo-1H-pyrazolo[3,4-d]pyrimidin-1-yl]piperidine-1-carboxylate (300 mg, 0.68 mmol, 1.00 equiv), 2-[4-(3-fluorophenoxy)phenyl]-4,4,5,5-tetramethyl-1,3,2-dioxaborolane (255 mg, 0.81 mmol, 1.20 equiv), sodium carbonate (143 g, 1.35 mol, 1998.01 equiv), ethylene glycol dimethyl ether (50 mL), water (15 mL), and Pd(PPh$_3$)$_4$ (40 mg, 0.03 mmol, 0.05 equiv). The resulting solution was stirred overnight at 80° C. and then concentrated under vacuum. The residue was loaded onto a silica gel column and eluted with dichloromethane/methanol (100/1) to give 260 mg (76%) of tert-butyl (3R)-3-[4-amino-3-[4-(3-fluorophenoxy)phenyl]-1H-pyrazolo[3,4-d]pyrimidin-1-yl]piperidine-1-carboxylate as a yellow solid.

Step 3

Into a 100 mL round-bottom flask, was placed a solution of tert-butyl (3R)-3-[4-amino-3-[4-(3-fluorophenoxy)phenyl]-1H-pyrazolo[3,4-d]pyrimidin-1-yl]piperidine-1-carboxylate (260 mg, 0.52 mmol, 1.00 equiv) in dichloromethane (50 mL). Trifluoroacetic acid (10 mL) was added dropwise with stirring. The resulting solution was stirred for 12 h at room temperature and then concentrated under vacuum. The residue was diluted with 20 mL of water. The pH value of the solution was adjusted to >7 with sodium carbonate. The resulting solution was extracted with dichloromethane and the organic layers combined and dried over anhydrous sodium sulfate and concentrated under vacuum to give 180 mg (86%) of 3-[4-(3-fluorophenoxy)phenyl]-1-[(3R)-piperidin-3-yl]-1H-pyrazolo[3,4-d]pyrimidin-4-amine as a brown solid.

Reference N

Synthesis of 3-[4-(2,6-difluorophenoxy)phenyl]-1-[(3R)-piperidin-3-yl]-1H-pyrazolo[3,4-d]pyrimidin-4-amine

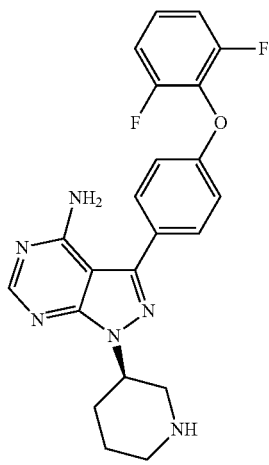 [SMILES: Nc1ncnc2c1c(-c1ccc(Oc3c(F)cccc3F)cc1)nn2[C@@H]1CCCNC1]

Step 1

Into a 250 mL 3-necked round-bottom flask purged and maintained under an inert atmosphere of nitrogen, was placed a solution of tert-butyl (3R)-3-[4-amino-3-iodo-1H-pyrazolo[3,4-d]pyrimidin-1-yl]piperidine-1-carboxylate (500 mg, 1.13 mmol, 1.00 equiv) in 1,4-dioxane/H2O (100/30 mL), 2-[4-(2,6-difluorophenoxy)phenyl]-4,4,5,5-tetramethyl-1,3,2-dioxaborolane (420 mg, 1.26 mmol, 1.1 equiv), sodium carbonate (240 mg, 2.26 mmol, 2.0 equiv), and Pd(PPh3)4 (65 mg, 0.06 mmol, 0.05 equiv). The resulting solution was stirred for 15 h at 90° C. in an oil bath and then concentrated under vacuum. The residue was diluted with water and extracted with dichloromethane and the organic layers combined. The organics were washed with brine, dried over anhydrous sodium sulfate and concentrated. The residue was loaded onto a silica gel column and eluted with dichloromethane/methanol (10/1) to give 500 mg (85%) of tert-butyl (3R)-3-[4-amino-3-[4-(2,6-difluorophenoxy)-phenyl]-1H-pyrazolo[3,4-d]pyrimidin-1-yl]piperidine-1-carboxylate as a white solid.

Step 2

Into a 100 mL round-bottom flask, was placed a solution of tert-butyl (3R)-3-[4-amino-3-[4-(2,6-difluorophenoxy)phenyl]-1H-pyrazolo[3,4-d]pyrimidin-1-yl]piperidine-1-carboxylate (450 mg, 0.86 mmol, 1.00 equiv) in dichloromethane (40 mL). CF$_3$COOH (10 mL) to added dropwise with stirring at 25° C. over 10 min and the resulting solution was stirred for 3 h at 25° C. and then concentrated under vacuum. The resulting solution was diluted with dichloromethane and washed with aqueous sodium bicarbonate and brine. The organics were dried over anhydrous sodium sulfate and concentrated under vacuum to give 410 mg of 3-[4-(2,6-difluorophenoxy)phenyl]-1-[(3R)-piperidin-3-yl]-1H-pyrazolo[3,4-d]pyrimidin-4-amine as a white solid.

Reference O

Synthesis of 3-[4-(2,5-difluorophenoxy)phenyl]-1-[(3R)-piperidin-3-yl]-1H-pyrazolo[3,4-d]pyrimidin-4-amine

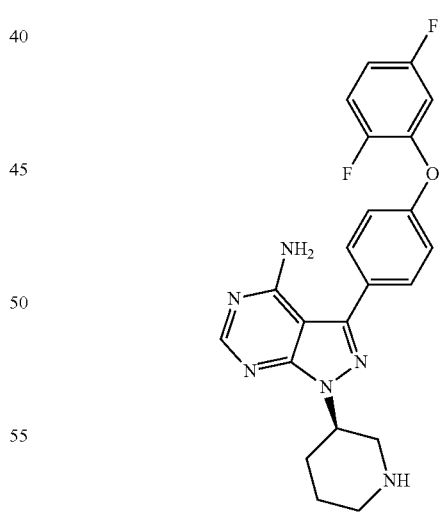

Step 1

Into a 500 mL 3-necked round-bottom flask, was placed a solution of sodium hydride (3.9 g, 162.50 mmol, 1.7 equiv) in N,N-dimethylformamide (200 mL). This was followed by the addition of a solution of 1-fluoro-4-nitrobenzene (13.6 g, 96.39 mmol, 1.00 equiv) in N,N-dimethylformamide (50 mL) dropwise with stirring at 0° C. over 20 min. The reaction mixture was stirred for 2 hr at 25° C. and then CuCl (9.6 g, 96.97 mmol, 1.0 equiv) was added, followed by addition of a solution of 2,5-difluorophenol (15.5 g, 119.15 mmol, 1.2 equiv) in N,N-dimethylformamide (50 mL) dropwise with stirring at 25° C. over 10 min. The resulting solution was stirred for 12 h at 100° C. in an oil bath and then diluted with water and washed with ether, water and brine. The reaction mixture was dried over anhydrous sodium sulfate and concentrated. The residue was loaded onto a silica gel column and eluted with ethyl acetate/petroleum ether (1/8) to give 19.5 g (81%) of 1,4-difluoro-2-(4-nitrophenoxy)benzene as a brown solid, Step 2

Into a 500 mL 3-necked round-bottom flask purged and maintained under an inert atmosphere of nitrogen, was placed a solution of 1,4-difluoro-2-(4-nitrophenoxy)benzene (19.5 g, 77.63 mmol, 1.00 equiv) in methanol (200 mL), and Raney Nickel (2 g). This was followed by the addition of a solution of hydrazine hydrate (11.66 g) in methanol (50 mL) dropwise with stirring at 25° C. over 15 min. The resulting solution was stirred for 12 h at 25° C. and then filtrated and the filtrate was concentrated under vacuum. The residue was diluted with ethyl acetate, washed with water and brine, dried over anhydrous sodium sulfate and concentrated under vacuum to give 16 g (93%) of 4-(2,5-difluorophenoxy)aniline as a black oil.

Step 3

Into a 250 mL 4-necked round-bottom flask, was placed 4-(2,5-difluorophenoxy)-aniline (9 g, 40.69 mmol, 1.00 equiv), hydrogen chloride (37%) (10.2 g, 100 mmol, 2.5 equiv) and water (20 mL). A solution of NaNO$_2$ (3.1 g, 44.93 mmol, 1.10 equiv) in water (10 mL) was added dropwise with stirring at 0° C. over 5 min. After stirring at 0° C. for 30 min., the mixture was added into a solution of NaI (18 g, 120.00 mmol, 3.0 equiv) in water (20 mL) dropwise with stirring at 25° C. The resulting solution was stirred for 12 h at 25° C. and then extracted with ethyl acetate and the organic layers combined. The combined organics were washed with water and brine, dried over anhydrous sodium sulfate and concentrated under vacuum to give 10.5 g (78%) of 1,4-difluoro-2-(4-iodophenoxy)benzene as brown oil.

Step 4

Into a 100 mL 3-necked round-bottom flask purged and maintained under an inert atmosphere of nitrogen, was placed a solution of 1,4-difluoro-2-(4-iodophenoxy)benzene (2 g, 6.02 mmol, 1.00 equiv) in N,N-dimethylformamide (50 mL), 4,4,5,5-tetramethyl-2-(tetramethyl-1,3,2-dioxaborolan-2-yl)-1,3,2-dioxaborolane (1.68 g, 6.62 mmol, 1.10 equiv), potassium acetate (1.76 g, 17.93 mmol, 3.0 equiv), and Pd(OAc)$_2$ (68 mg, 0.30 mmol, 0.05 equiv). The resulting solution was stirred for 12 h at 85° C. in an oil bath and then diluted with water. The resulting solution was extracted with ethyl acetate and the organic layers combined. The combined organics were washed with water and brine and dried over anhydrous sodium sulfate and concentrated. The residue was loaded onto a silica gel column and eluted with ethyl acetate/petroleum ether (1/8) to give 1.5 g (75%) of 2-[4-(2,5-difluorophenoxy)phenyl]-4,4,5,5-tetramethyl-1,3,2-dioxaborolane as a light yellow solid.

Step 5

Into a 250-mL 3-necked round-bottom flask purged and maintained under an inert atmosphere of nitrogen, was placed a solution of tert-butyl (3R)-3-[4-amino-3-iodo-1H-pyrazolo[3,4-d]pyrimidin-1-yl]piperidine-1-carboxylate (500 mg, 1.13 mmol, 1.00 equiv) in 1,4-dioxane/H2O (100/30 mL), 2-[4-(2,5-difluorophenoxy)phenyl]-4,4,5,5-tetramethyl-1,3,2-dioxaborolane (420 mg, 1.26 mmol, 1.1 equiv), sodium carbonate (240 mg, 2.26 mmol, 2.0 equiv) and Pd(PPh$_3$)$_4$ (65 mg, 0.06 mmol, 0.05 equiv). The resulting solution was stirred for 12 h at 90° C. in an oil bath and then concentrated under vacuum. The residue was diluted with water and the resulting solution was extracted with dichloromethane and the organic layers were combined. The combined organics were washed with brine, dried over anhydrous sodium sulfate and concentrated. The residue was loaded onto a silica gel and eluted with dichloromethane/methanol (10/1) to give 510 mg (87%) of tert-butyl (3R)-3-[4-amino-3-[4-(2,5-difluorophenoxy)phenyl]-1H-pyrazolo[3,4-d]pyrimidin-1-yl]piperidine-1-carboxylate as a white solid.

Step 6

Into a 100 mL round-bottom flask, was placed a solution of tert-butyl (3R)-3-[4-amino-3-[4-(2,5-difluorophenoxy)phenyl]-1H-pyrazolo[3,4-d]pyrimidin-1-yl]piperidine-1-carboxylate (450 mg, 0.86 mmol, 1.00 equiv) in dichloromethane (40 mL). This was followed by the addition of CF$_3$COOH (10 mL) dropwise with stirring at 25° C. over 5 min. The resulting solution was stirred for 3 h at 25° C. and then concentrated under vacuum. The residue was diluted with dichloromethane and the resulting mixture was washed with aqueous sodium bicarbonate and brine and dried over anhydrous sodium sulfate and concentrated under vacuum to give 400 mg (99%) of 3-[4-(2,5-difluorophenoxy)phenyl]-1-[(3R)-piperidin-3-yl]-1H-pyrazolo[3,4-d]pyrimidin-4-amine as a white solid.

Reference P

Synthesis of 1-[[(2S)-4,4-difluoropyrrolidin-2-yl]methyl]-3-(2-fluoro-4-phenoxyphenyl)-1H-pyrazolo[3,4-d]pyrimidin-4-amine trifluoroacetic acid salt

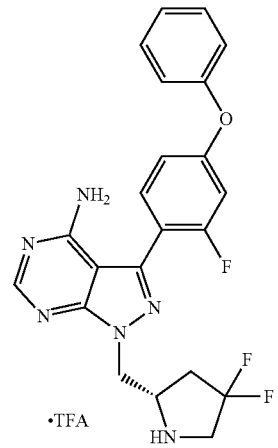 [SMILES: Nc1ncnc2c1c(-c1ccc(Oc3ccccc3)cc1F)nn2C[C@@H]1CC(F)(F)CN1]

Step 1

Into a solution of 1-tert-butyl 2-methyl (2S)-4,4-difluoropyrrolidine-1,2-dicarboxylate (900 mg, 3.39 mmol, 1.00 equiv) in tetrahydrofuran (15 mL) was added LiBH$_4$ (200 mg, 9.1 mmol, 2.7 equiv) in batches at 0° C. The resulting solution was stirred overnight at room temperature, then was diluted with EtOAc and washed with water and brine, dried over anhydrous sodium sulfate and concentrated to give 0.8 g of tert-butyl (2S)-4,4-difluoro-2-(hydroxymethyl)pyrrolidine-1-carboxylate as reddish oil.

Step 2

Under nitrogen, to a solution of 3-iodo-1H-pyrazolo[3,4-d]pyrimidin-4-amine (2.61 g, 10.00 mmol, 1.00 equiv), tert-butyl (2S)-4,4-difluoro-2-(hydroxymethyl)pyrrolidine-1-carboxylate (2.37 g, 9.99 mmol, 1.00 equiv) and TPP (4 g, 15.2 mmol, 1.50 equiv) in THF was added DIAD (3.00 g, 15.0 mmol, 1.50 equiv) at 0° C. in 30 min. The resulting solution was stirred overnight at room temperature. The mixture was then concentrated under vacuum and the residue was applied onto a silica gel column with dichloromethane/ethyl acetate (3/1) to give 1 g of tert-butyl (2S)-2-([4-amino-3-iodo-1H-pyrazolo[3,4-d]-pyrimidin-1-yl]methyl)-4,4-difluoropyrrolidine-1-carboxylate as a reddish oil.

Step 3

Under nitrogen atmosphere, a suspension of tert-butyl (2S)-2-([4-amino-3-iodo-1H-pyrazolo[3,4-d]pyrimidin-1-yl]methyl)-4,4-difluoropyrrolidine-1-carboxylate (800 mg, 1.67 mmol, 1.00 equiv), (2-fluoro-5-phenoxyphenyl)boronic acid (480 mg, 2.07 mmol, 1.20 equiv), Pd(dppf)Cl$_2$ (140 mg, 0.17 mmol, 0.10 equiv), sodium carbonate (0.53 g, 5.00 mmol, 3.00 equiv) in 1,4-dioxane/water (40/10 mL) was stirred at 80° C. overnight. The resulting mixture was concentrated under vacuum. The residue was submitted to silica gel column and eluting with ethyl acetate/petroleum ether (1:2 to 3:1) to give 0.6 g (67%) of tert-butyl (2S)-2-[[4-amino-3-(2-fluoro-4-phenoxyphenyl)-1H-pyrazolo[3,4-d]pyrimidin-1-yl]methyl]-4,4-difluoropyrrolidine-1-carboxylate as a reddish solid.

Step 4

To a solution of tert-butyl (2S)-2-[[4-amino-3-(2-fluoro-4-phenoxyphenyl)-1H-pyrazolo[3,4-d]pyrimidin-1-yl]methyl]-4,4-difluoropyrrolidine-1-carboxylate (600 mg, 1.11 mmol, 1.00 equiv) in dichloromethane (10 mL) was added trifluoroacetic acid (2 mL) dropwise. The resulting solution was stirred at room temperature for 2 h. The mixture was concentrated under vacuum to give 0.85 g (crude) of 1-[[(2S)-4,4-difluoropyrrolidin-2-yl]methyl]-3-(2-fluoro-4-phenoxyphenyl)-1H-pyrazolo[3,4-d]pyrimidin-4-amine trifluoroacetic acid salt as a brown semi-solid.

Reference Q

Synthesis of (R)-5-(4-phenoxyphenyl)-7-(piperidin-3-yl)-7H-pyrrolo[2,3-d]pyrimidin-4-amine

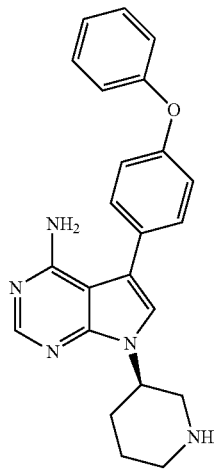 [SMILES: Nc1ncnc2c1c(-c1ccc(Oc3ccccc3)cc1)cn2[C@@H]1CCCNC1]

Step 1

To the solution of 4-chloro-7H-pyrrolo[2,3-d]pyrimidine (10 g, 65.12 mmol, 1.0 eq) and (S)-tert-butyl 3-hydroxypiperidine-1-carboxylate (13.0 g, 65.12 mmol, 1.0 eq) and PPh$_3$ (34.20 g, 130.24 mmol, 2.0 eq) in THF (400 mL) at 0° C. was added DEAD (22.68 g, 130.24 mmol, 2.0 eq). The resulted mixture was stirred and warmed to RT for 12 h. The reaction mixture was purified by column (10% EtOAc in petroleum ether) to afford (R)-tert-butyl 3-(4-chloro-7H-pyrrolo[2,3-d]pyrimidin-7-yl)piperidine-1-carboxylate (2.1 g, 10% in yield) as a colorless oil.

Step 2

The mixture of (R)-tert-butyl 3-(4-chloro-7H-pyrrolo[2,3-d]pyrimidin-7-yl)piperidine-1-carboxylate (1.7 g, 5.05 mmol) and NIS (1.25 g, 5.55 mmol) in DMF (20 mL) was stirred for 12 h at room temperature. Water was added to the mixture, which was extracted with EtOAc, the combined organic layers were dried and purified by column to give (R)-tert-butyl 3-(4-chloro-5-iodo-7H-pyrrolo[2,3-d]pyrimidin-7-yl)piperidine-1-carboxylate (2.0 g, 86% in yield).

Step 3

A solution of (R)-tert-butyl 3-(4-chloro-5-iodo-7H-pyrrolo[2,3-d]pyrimidin-7-yl)piperidine-1-carboxylate (2.0 g, 4.32 mmol) in IPA (saturated with NH$_3$) (20 mL) was stirred at 100° C. for 12 h in a 100 mL of autoclave. The organic layer was concentrated and purified on silica gel chromatography (eluted with PE:EtOAc=1:1) to afford (R)-tert-butyl 3-(4-amino-5-iodo-7H-pyrrolo[2,3-d]pyrimidin-7-yl)piperidine-1-carboxylate (1.5 g, 78% in yield).

Step 4

A mixture of (R)-tert-butyl 3-(4-amino-5-iodo-7H-pyrrolo[2,3-d]pyrimidin-7-yl)piperidine-1-carboxylate (250 mg, 0.56 mmol), 4-phenoxyphenylboronic acid (133 mg, 0.62 mmol), Pd(PPh$_3$)$_4$ (100 mg) and Na$_2$CO$_3$ (150 mg, 1.41 mmol) in dioxane/H$_2$O (40/10 ml) was stirred at 100° C. for 4 h. The reaction mixture was concentrated and purified by Pre-TLC to obtain (R)-tert-butyl 3-(4-amino-5-(4-phenoxyphenyl)-7H-pyrrolo[2,3-d]pyrimidin-7-yl)piperidine-1-carboxylate (150 mg, 55% in yield).

Step 5

The mixture of (R)-tert-butyl 3-(4-amino-5-(4-phenoxyphenyl)-7H-pyrrolo[2,3-d]pyrimidin-7-yl)piperidine-1-carboxylate (150 mg, 0.31 mmol) in 10 ml DCM was added TFA (10 ml). The reaction mixture was stirred at RT for 2 h. Solvent was removed, sat. NaHCO$_3$ (10 mL) was added. The resulted mixture was extracted with DCM. The organic layer was dried and concentrated to afford (R)-5-(4-phenoxyphenyl)-7-(piperidin-3-yl)-7H-pyrrolo[2,3-d]pyrimidin-4-amine (100 mg, 83% in yield), which was subjected to the next step without any further purification.

Reference R

Synthesis of (S)-5-(4-phenoxyphenyl)-7-(pyrrolidin-2-ylmethyl)-7H-pyrrolo[2,3-d]pyrimidin-4-amine

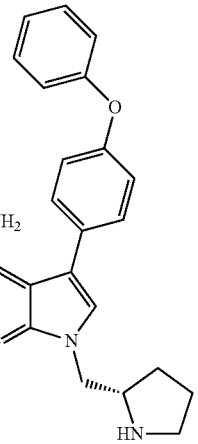

Step 1

To a solution of 4-chloro-7H-pyrrolo[2,3-d]pyrimidine (8.0 g, 52.32 mmol, 1.0 eq) in DMF (40 mL), NIS (15.7 g, 57.55 mmol, 1.1 eq) was added at 0° C. The reaction mixture was stirred overnight at room temperature. Water (40 mL)

was added to the reaction mixture, extracted with EtOAc. The organic layer was dried over Na₂SO₄ and concentrated under vacuum to give 4-chloro-5-iodo-7H-pyrrolo[2,3-d]pyrimidine (14.6 g, 100% in yield).

Step 2

To a solution of 4-chloro-5-iodo-7H-pyrrolo[2,3-d]pyrimidine (4.0 g, 14.34 mmol, 1.0 eq), (S)-tert-butyl 2-(hydroxymethyl)pyrrolidine-1-carboxylate (4.04 g, 20.08 mmol, 1.4 eq), and PPh₃ (7.5 g, 28.68 mmol, 2.0 eq) in dry THF (30 mL) at 0° C. was added DIAD (5.80 g, 28.68 mmol, 2.0 eq) dropwise. The mixture was stirred at RT for 5 h. The reaction mixture was concentrated and purified by silica gel chromatography (eluted with PE:EtOAc=1:1) to afford (S)-2-(4-chloro-5-iodo-pyrrolo[2,3-d]pyrimidin-7-ylmethyl)-pyrrolidine-1-carboxylic acid tert-butyl ester (5.1 g, 77% in yield).

Step 3

A solution of (S)-2-(4-chloro-5-iodo-pyrrolo[2,3-d]pyrimidin-7-ylmethyl)-pyrrolidine-1-carboxylic acid tert-butyl ester (3.5 g, 6.93 mmol) in MeOH (saturated with NH₃) was stirred 100° C. and overnight in a 100 mL of sealed tube. The organic layer was concentrated under reduced pressure to provide a white solid which was purified by silica gel chromatography eluted with PE:EtOAc=1:1 to afford (S)-2-(4-amino-5-iodo-pyrrolo[2,3-d]pyrimidin-7-ylmethyl)-pyrrolidine-1-carboxylic acid tert-butyl ester (2.7 g, 87.98% in yield).

Step 4

A solution of (S)-2-(4-amino-5-iodo-pyrrolo[2,3-d]pyrimidin-7-ylmethyl)-pyrrolidine-1-carboxylic acid tert-butyl ester (500.00 mg, 1.13 mmol, 1.0 eq), 4-phenoxyphenyl-boronic acid (240.00 mg, 1.13 mmol, 1.0 eq), Pd(PPh₃)₄ (100.00 mg), and Na₂CO₃ (300.00 mg, 2.83 mmol, 2.5 eq) in Dioxane/H₂O (40/10 ml) was stirred at 90° C. for 4 h. The reaction mixture was concentrated and purified by Pre-TLC to afford (S)-2-[4-amino-5-(4-phenoxy-phenyl)-pyrrolo[2,3-d]pyrimidin-7-ylmethyl]-pyrrolidine-1-carboxylic acid tert-butyl ester (500 mg, 91% in yield).

Step 5

To a solution of (S)-2-[4-amino-5-(4-phenoxy-phenyl)-pyrrolo[2,3-d]pyrimidin-7-ylmethyl]-pyrrolidine-1-carboxylic acid tert-butyl ester (500 mg, 1.03 mmol) in 10 ml of DCM was added TFA (10 ml). The reaction mixture was stirred at RT for 2 h. The mixture was concentrated to give (S)-5-(4-phenoxy-phenyl)-7-pyrrolidin-2-ylmethyl-7H-pyrrolo[2,3-d]pyrimidin-4-ylamine (400 mg), which was subjected to the next step without any further purification.

Reference S

Synthesis of (S)-6-methyl-5-(4-phenoxyphenyl)-7-(pyrrolidin-2-ylmethyl)-7H-pyrrolo[2,3-d]pyrimidin-4-amine

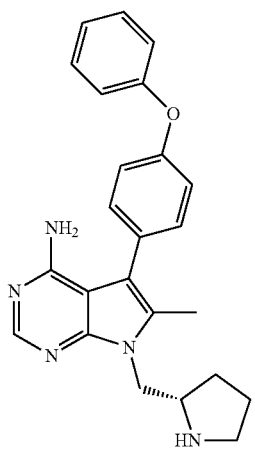 [SMILES: Cc1c(-c2ccc(Oc3ccccc3)cc2)c2c(N)ncnc2n1C[C@@H]1CCCN1]

Step 1

To a solution of 4-chloro-7H-pyrrolo[2,3-d]pyrimidine (10 g, 65.12 mmol, 1.0 eq) in THF (300 mL), NaH (5.30 g, 130.24 mmol, 2 eq) was added at 0° C. After 3 h, benzenesulfonyl chloride (22.53 g, 130.24 mmol, 2 eq) was added. The temperature was warmed to RT and continued for 1 h. The reaction mixture was poured into sat. NH₄Cl and extracted with EtOAc. The organic layers were dried, concentrated and purified by column chromatography (eluting with 10% EtOAc in PE) to afford 4-chloro-7-(phenylsulfonyl)-7H-pyrrolo[2,3-d]pyrimidine as a brown solid (4.5 g, 24% in yield)

Step 2

To the solution of 4-chloro-7-(phenylsulfonyl)-7H-pyrrolo[2,3-d]pyrimidine (3 g, 12.6 mmol, 1.0 eq) and TMEDA (3.0 mL, 18.9 mmol, 1.5 eq) in THF (120 mL) at −78° C. was added n-BuLi (7.5 mL, 18.9 mmol, 1.5 eq). After 3 min, CH₃I (3.7 mL, 59.2 mmol, 4.7 eq) was added. After 3 h, the reaction mixture was warmed to RT over 1 h. The reaction was quenched by addition of sat NH₄Cl (10 mL). EtOAc (200 mL) and water (100 mL) was added. The organic layer was separated, dried and concentrated to afford 4-chloro-6-methyl-7-(phenylsulfonyl)-7H-pyrrolo[2,3-d]pyrimidine as a brown solid (6.7 g, 90% in yield).

Step 3

To the solution of 4-chloro-6-methyl-7-(phenylsulfonyl)-7H-pyrrolo[2,3-d]pyrimidine (10 g, 32.5. mmol, 1.0 eq) in THF (400 mL), t-BuOK (18.23 g, 163.0 mmol, 5 eq) was added and stirred at RT for 12 h. Sat. NaHCO₃ (50 mL) was added and extracted with EtOAc. The organic layers were separated, dried and concentrated to afford 4-chloro-6-methyl-7H-pyrrolo[2,3-d]pyrimidine as a brown solid (2.7 g, 50% in yield).

Step 4

To the solution of 4-chloro-6-methyl-7H-pyrrolo[2,3-d]pyrimidine (1.0 g, 5.97 mmol, 1.0 eq) and (S)-tert-butyl 2-(hydroxymethyl)pyrrolidine-1-carboxylate (1.32 g, 6.57 mmol, 1.1 eq) and PPh₃ (3.03 g, 11.94 mmol, 2.0 eq) in THF (50 mL), DIEA (2.08 g, 11.94 mmol, 2.0 eq) was added at 0° C. The resulted mixture was stirred and warmed to RT for 12 h. Solvent was removed and purified by column chromatography (eluting with 10% EtOAc in PE) to afford (S)-tert-butyl 2-((4-chloro-6-methyl-7H-pyrrolo[2,3-d]pyrimidin-7-yl)methyl)pyrrolidine-1-carboxylate as a white solid (2.08 g, 100% in yield).

Step 5

To the solution of (S)-tert-butyl 2-((4-chloro-6-methyl-7H-pyrrolo[2,3-d]pyrimidin-7-yl)methyl)pyrrolidine-1-carboxylate (1.0 g, 2.86 mmol, 1.0 eq) in DMF (20 mL), 2 (0.675 g, 3.00 mmol, 1.05 eq) was added at 0° C. The resulted mixture was stirred and warmed to RT for 12 h. Solvent was removed and purified by column chromatography to afford (S)-tert-butyl 2-((4-chloro-5-iodo-6-methyl-7H-pyrrolo[2,3-d]pyrimidin-7-yl)methyl)pyrrolidine-1-carboxylate as white solid (1.0 g, 77% in yield) which was converted to the title compound as described in Reference R above.

Example 1

Synthesis of (R)-1-(2-((4-amino-3-(4-phenoxyphenyl)-1H-pyrazolo[3,4-d]pyrimidin-1-yl)methyl)pyrrolidin-1-yl)-3-cyclopropyl-2-fluoroprop-2-en-1-one

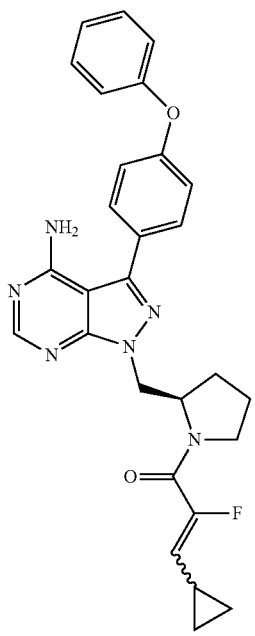 [SMILES: Nc1ncnc2c1c(-c1ccc(Oc3ccccc3)cc1)nn2C[C@H]1CCCN1C(=O)C(F)=CC1CC1]

Step 1

Ethyl 2-(diethoxyphosphoryl)-2-fluoroacetate (1075.5 mg, 4.44 mmol) was placed in 10 mL of THF and cooled to 0° C. in ice-batch. NaH (94.0 mg, 3.92 mmol) was added and stirred for 30 min. Cyclopropanecarbaldehyde was added to the reaction mixture slowly and the reaction mixture was allowed to warm to room temperature for 2 h. The reaction was worked up with dichloromethane and water. The organic layer was washed with brine, dried with $MgSO_4$ and concentrated to give (E/Z)-ethyl 3-cyclopropyl-2-fluoroacrylate isomers. The products were directly used in the next step.

Step 2

A mixture of (E/Z)-ethyl 3-cyclopropyl-2-fluoroacrylate isomers (160 mg, 1.01 mmol) was dissolved in dioxane (5 mL) and water (5 mL), and NaOH (162 mg, 4.04 mmol) were added. The reaction was completed in 10 min. The mixture was acidified with 2M HCl to pH~2 and extracted wht DCM. The organics were washed with brine, dried with $MgSO_4$ and then concentrated to get (E/Z)-3-cyclopropyl-2-fluoroacrylic acid isomers.

Step 3

A mixture of (E/Z)-3-cyclopropyl-2-fluoroacrylic acid (68 mg, 0.52 mmol), (R)-3-(4-phenoxyphenyl)-1-(pyrrolidin-2-ylmethyl)-1H-pyrazolo[3,4-d]pyrimidin-4-amine (158 mg, 0.52 mmol), triethylamine (69 mg, 0.68 mmol) and DMF (4 mL) were stirred at room temperature for 10 mins. O-(7-Azabenzotriazol-1-yl)-N,N,N',N'-tetramethyluronium PF6 (257 mg, 0.68 mmol) was then added and the mixture was stirred for 75 min. The solvent was evaporated and the oil was worked up with ethylacetate and water. Organic layer was washed with brine and dried with $MgSO_4$. Purification with column chromatography ($SiO_2$, MeOH|DCM with gradient form 1% to 2% in total 500 mL) gave (R)-1-(2-((4-amino-3-(4-phenoxyphenyl)-1H-pyrazolo[3,4-d]pyrimidin-1-yl)methyl)pyrrolidin-1-yl)-3-cyclopropyl-2-fluoroprop-2-en-1-one. MS (pos. ion) m/z: 499 (M+1).

Proceeding as described in example 1 above but substituting cyclopropane-carbaldehyde with 2-(dimethylamino)-2-methylpropanal, tert-butyl methyl(2-methyl-1-oxopropan-2-yl)carbamate, and tert-butyl 2-methyl-1-oxopropan-2-ylcarbamate, (R)-1-(2-((4-amino-3-(4-phenoxyphenyl)-1H-pyrazolo[3,4-d]pyrimidin-1-yl)methyl)pyrrolidin-1-yl)-4-(dimethylamino)-2-fluoro-4-methylpent-2-en-1-one, (R)-1-(2-((4-amino-3-(4-phenoxyphenyl)-1H-pyrazolo[3,4-d]pyrimidin-1-yl)methyl)pyrrolidin-1-yl)-2-fluoro-4-methyl-4-(methylamino)pent-2-en-1-one, and (R)-4-amino-1-(2-((4-amino-3-(4-phenoxyphenyl)-1H-pyrazolo[3,4-d]pyrimidin-1-yl)methyl)pyrrolidin-1-yl)-2-fluoro-4-methylpent-2-en-1-one can be prepared respectively, after hydrolysis of the Boc group when tert-butyl methyl(2-methyl-1-oxopropan-2-yl)carbamate, and tert-butyl 2-methyl-1-oxopropan-2-ylcarbamate are used.

Example 2

Synthesis of (R)-1-(2-((4-amino-3-(4-phenoxyphenyl)-1H-pyrazolo[3,4-d]pyrimidin-1-yl)methyl)pyrrolidin-1-yl)-3-cyclopropyl-2-(trifluoromethyl)prop-2-en-1-one

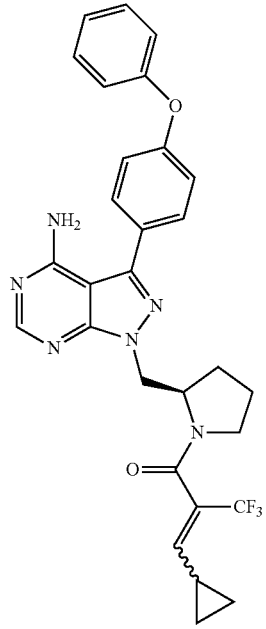 [SMILES: Nc1ncnc2c1c(-c1ccc(Oc3ccccc3)cc1)nn2C[C@H]1CCCN1C(=O)C(=CC1CC1)C(F)(F)F]

Step 1

(Cyclopropylmethyl)triphenylphosphonium bromide was charged to a 2-neck dried 250 mL flask with argon. Dried THF (12 mL) was added slowly dripwise and stirred at room temperature for 1 h. The reaction mixture was cooled to −70° C. (dry ice in ethanol) and BuLi (2.5 M in Hexane, 1.55 mL) was added dropwise as the solution turned from clear to red. The reaction mixture was allowed to warm to room temperature over 2 h and stirred for an additional 1 h. The mixture was again cooled to −70° C. and methyl 3,3,3-trifluoro-2-oxopropanoate was added dropwise. After 90 min, the reaction mixture was warmed to room temperature and then purified with 1% MeOH/DCM (300 mL) to get (E/Z)-methyl 3-cyclopropyl-2-(trifluoromethyl)acrylate isomers.

Step 2

A mixture of (E/Z)-methyl 3-cyclopropyl-2-(trifluoromethyl)acrylate isomers was dissolved in dioxane 65 mL) and water (6 mL), and NaOH (800 mg) was added. After 2 h, the mixture was acidified with 2M HCl to pH~2 and extracted with EtOAc. The organics were washed with brine, dried with $MgSO_4$ and then concentrated to get (E/Z)-3-cyclopropyl-2-(trifluoromethyl)acrylic acid.

Step 3

A mixture of (E/Z)-3-cyclopropyl-2-(trifluoromethyl) acrylic acid (30 mg, 0.17 mmol), (R)-3-(4-phenoxyphenyl)-1-(pyrrolidin-2-ylmethyl)-1H-pyrazolo[3,4-d]pyrimidin-4-amine (158 mg, 0.52 mmol), Triethylamine (18.2 mg, 0.18 mmol) and DMF (3 mL) were stirred at room temperature for 10 min. O-(7-Azabenzotriazol-1-yl)-N,N,N',N'-tetramethyluronium PF6 (69 mg, 0.18 mmol) was added and the reaction mixture was stirred for 2 h. The solvent was evaporated and the oil was worked up with ethylacetate and water. The organic layer was washed with brine and dried over $MgSO_4$. Purification with column chromatography ($SiO_2$, MeOH|DCM with gradient form 1% to 2% in total 500 mL) gave (R)-1-(2-((4-amino-3-(4-phenoxyphenyl)-1H-pyrazolo[3,4-d]pyrimidin-1-yl)methyl)pyrrolidin-1-yl)-3-cyclopropyl-2-fluoroprop-2-en-1-one. MS (pos. ion) m/z: 549 (M+1).

Example 3

Synthesis of 3-(3-(4-amino-3-(4-phenoxyphenyl)-1H-pyrazolo[3,4-d]pyrimidin-1-yl)propyl)-5-(cyclopropylmethylene)thiazolidine-2,4-dione

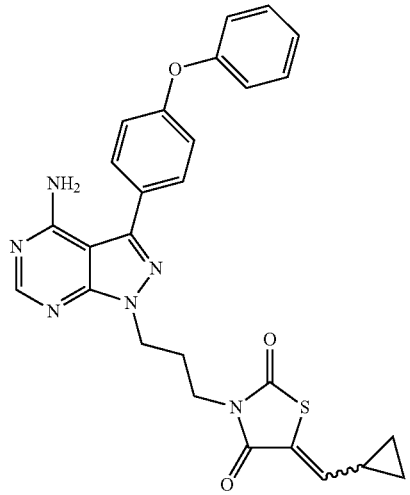 [SMILES: Nc1ncnc2c1c(-c1ccc(Oc3ccccc3)cc1)nn2CCCN1C(=O)SC(=CC2CC2)C1=O]

Step 1

A solution of 3-(4-phenoxyphenyl)-1H-pyrazolo[3,4-d]pyrimidin-4-amine (1.0 g, 3.3 mmol, 1.0 eq.) 3-bromopropan-1-ol (0.55 g, 4.0 mmol, 1.2 eq.) and potassium hydroxide (0.4 g, 10 mmol, 3.0 eq.) in DMSO (25 mL) was stirred at room temperature for 4 h. The reaction mixture was quenched with water and the resulting solution was extracted with ethyl acetate. The organic layers were combined, washed with brine, dried and concentrated. The residue was purified on silica gel eluting with ethyl acetate to give 3-(4-amino-3-(4-phenoxyphenyl)-1H-pyrazolo[3,4-d]pyrimidin-1-yl)propan-1-ol (0.5 g) as a light yellow solid.

Step 2

To a solution of 3-(4-amino-3-(4-phenoxyphenyl)-1H-pyrazolo[3,4-d]pyrimidin-1-yl)propan-1-ol (0.5 g, 1.4 mmol, 1 eq.), thiazolidine-2,4-dione (0.20 g, 1.7 mmol, 1.2 eq.), triphenylphosphine (1.1 g, 4.2 mmol, 3.0 eq.) in THF (25 mL) in ice/water bath was added DIAD (0.85 mmol, 4.2 mmol, 3.0 eq.) dropwise. The resulting solution was stirred at this temperature for 0.5 h and then stirred at room temperature for another 2 h. The volatile phase was removed off under reduced pressure. The residue was applied on silica gel and eluted to give 3-(3-(4-amino-3-(4-phenoxyphenyl)-1H-pyrazolo[3,4-d]pyrimidin-1-yl)propyl)thiazolidine-2,4-dione (0.4 g, 62%) as an off-white solid.

Step 3

A solution of 3-(3-(4-amino-3-(4-phenoxyphenyl)-1H-pyrazolo[3,4-d]pyrimidin-1-yl)propyl)thiazolidine-2,4-dione (0.20 g, 0.43 mmol), cyclopropanecarbaldehyde (91 mg, 1.3 mmol, 3.0 eq.) and a drop of piperidine in ethanol (15 mL) was refluxed overnight. The volatile phase was removed under reduced pressure. The residue was applied on silica gel and eluted with petroleum:ethyl acetate (3:2) to give 3-(3-(4-amino-3-(4-phenoxyphenyl)-1H-pyrazolo[3,4-d]pyrimidin-1-yl)propyl)-5-(cyclopropylmethylene thiazolidine-2,4-dione (50 mg) as a white solid. MS (ESI, pos. ion) m/z: 513 (M+1)

Example 4

Synthesis of 3-(2-(4-amino-3-(4-phenoxyphenyl)-1H-pyrazolo[3,4-d]pyrimidin-1-yl)ethyl)-5-benzylidenethiazolidine-2,4-dione

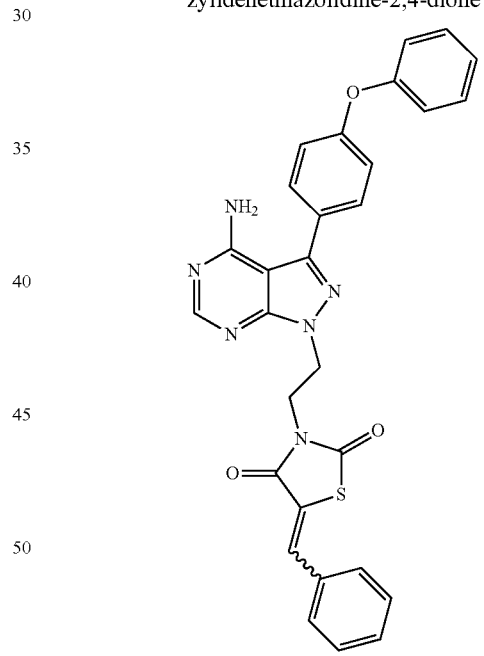

Step 1

Into a 500-mL 3-necked round-bottom flask purged and maintained with an inert atmosphere of nitrogen, was placed a solution of 1,3-thiazolidine-2,4-dione (10 g, 85.38 mmol, 1.00 equiv) in tetrahydrofuran (300 mL), 2-bromoethan-1-ol (10.6 g, 84.82 mmol, 1.00 equiv), triphenylphosphane (27 g, 102.94 mmol, 1.20 equiv). This was followed by the addition of a solution of DIAD (21 g, 103.96 mmol, 1.20 equiv) in tetrahydrofuran (30 mL) dropwise with stirring at 0-10° C. in 30 min. The resulting solution was stirred overnight at room temperature. The resulting mixture was concentrated under vacuum. The residue was applied onto a silica gel column and eluted with ethyl acetate/petroleum ether (1/50) to give 9 g (47%) of 3-(2-bromoethyl)-1,3-thiazolidine-2,4-dione as a colorless oil.

Step 2

Into a 50-mL 3-necked round-bottom flask purged and maintained with an inert atmosphere of nitrogen, was placed a solution of 3-(4-phenoxyphenyl)-1H-pyrazolo[3,4-d]pyrimidin-4-amine (800 mg, 2.64 mmol, 1.00 equiv) in N,N-dimethylformamide (25 mL), 3-(2-bromoethyl)-1,3-thiazolidine-2,4-dione (890 mg, 3.97 mmol, 1.50 equiv) and cesium carbonate (1.72 g, 5.26 mmol, 2.00 equiv). The resulting solution was stirred for 10 h at 80° C. in an oil bath. The reaction mixture was cooled with a water bath, diluted with 150 mL of ethyl acetate and washed with brine and water. The organic layer was dried over anhydrous sodium sulfate and concentrated under vacuum. The residue was applied onto a silica gel column and eluted with dichloromethane/methanol (100/1) to give 500 mg (42%) of 3-[2-[4-amino-3-(4-phenoxyphenyl)-1H-pyrazolo[3,4-d]pyrimidin-1-yl]ethyl]-1,3-thiazolidine-2,4-dione as a light yellow solid.

Step 3

Into a 50-mL round-bottom flask, was placed a solution of 3-[2-[4-amino-3-(4-phenoxyphenyl)-1H-pyrazolo[3,4-d]pyrimidin-1-yl]ethyl]-1,3-thiazolidine-2,4-dione (100 mg, 0.22 mmol, 1.00 equiv) in ethanol (20 mL) and benzaldehyde (47 mg, 0.44 mmol, 1.98 equiv) and piperidine (479.5 mg, 5.63 mmol, 25.14 equiv) were added. The resulting solution was stirred for 12 h at 70° C. in an oil bath. The resulting mixture was concentrated under vacuum. The residue was applied onto a silica gel column and eluted with dichloromethane/methanol (100/1) to give 31 mg (24%) of 3-[2-[4-amino-3-(4-phenoxyphenyl)-1H-pyrazolo[3,4-d]pyrimidin-1-yl]ethyl]-5-(phenylmethylidene)-1,3-thiazolidine-2,4-dione as a light yellow solid. LC-MS: (ES, m/z): 535 (M+H)

Example 5

Synthesis of 3-(2-(4-amino-3-(4-phenoxyphenyl)-1H-pyrazolo[3,4-d]pyrimidin-1-yl)ethyl)-5-(cyclopropylmethylene)thiazolidine-2,4-dione

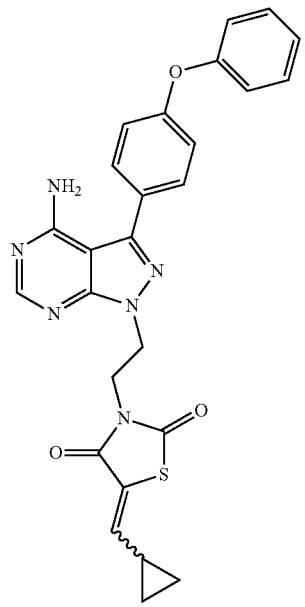 [SMILES: Nc1ncnc2c1c(-c1ccc(Oc3ccccc3)cc1)nn2CCN1C(=O)SC(=CC2CC2)C1=O]

Into a 50-mL scaled tube, was placed a solution of 3-[2-[4-amino-3-(4-phenoxyphenyl)-1H-pyrazolo[3,4-d]pyrimidin-1-yl]ethyl]-1,3-thiazolidine-2,4-dione (100 mg, 0.22 mmol, 1.00 equiv) in methanol (20 mL), cyclopropanecarbaldehyde (47 mg, 0.67 mmol, 2.99 equiv), piperidine (9.5 mg, 0.11 mmol, 0.50 equiv), dichloromethane (5 mL). The resulting solution was stirred overnight at room temperature. The resulting mixture was concentrated under vacuum. The residue was applied onto a silica gel column and eluted with dichloromethane/methanol (100/1) to give 28 mg (24%) of 3-[2-[4-amino-3-(4-phenoxyphenyl)-1H-pyrazolo[3,4-d]pyrimidin-1-yl]ethyl]-5-(cyclopropylmethylidene)-1,3-thiazolidine-2,4-dione as a white solid. LC-MS (ES, m/z): 499 (M+H)$^+$

BIOLOGICAL EXAMPLES

Example 1

Btk Enzymatic Activity Assay

A Caliper-based kinase assay (Caliper Life Sciences, Hopkinton, Mass.) was used to measure inhibition of Btk kinase activity of a compound of Formula (I). Serial dilutions of test compounds were incubated with human recombinant Btk (2 nM), ATP (40 μM) and a phosphoacceptor peptide substrate FAM-GEEPLYWSFPAKKK-NH$_2$ (1 μM) at room temperature for 3 h. The reaction was then terminated with EDTA, final concentration 20 mM and the phosphorylated reaction product was quantified on a Caliper Desktop Profiler (Caliper LabChip 3000). Percent inhibition was calculated for each compound dilution and the concentration that produced 50% inhibition was calculated. This value is presented as the IC$_{50}$. The IC$_{50}$ for a representative no. of compounds of the disclosure are provided below.

| Example # | IC$_{50}$ (um) |
| --- | --- |
| 1 | 0.203 |
| 2 | 0.041 |
| 3 | 0.023 |
| 4 | 0.86 |
| 5 | 0.049 |

Example 2

Tyrosine Kinase TR-FRET Assay

Inhibition of tyrosine kinase enzymatic activity by compounds is measured using time-resolved fluorescence resonance energy transfer (TR-FRET) (Invitrogen pamphlet: Optimization of a LanthaScreen Kinase assay for BTK). Here, a signal is observed only when a Europium-coupled phophotyrosine antibody binds the phosphorylated peptide. Compounds are first prepared in 100% DMSO and serially diluted 10 times via 3-fold dilution. 2.5 μl of inhibitor at 4-fold the final assay concentration is next transferred to the 384-well assay plate (Corning Catalog #3676). A solution of 2-fold the final concentration of appropriate kinase enzyme and Alexafluor 647-coupled peptide substrate (Invitrogen Catalog #5693) is next prepared in advance in a kinase buffer of 50 mM Hepes pH 7.5, 10 mM MgCl2, and 1 mM EGTA. For this solution, the final concentration of the appropriate kinase and peptide is typically 1 nM and 100 nM, respectively. 5 μL of this 2-fold mix of kinase and peptide is added as the second step of the procedure to the 384-well assay plate. To initiate the enzymatic reaction, 2.5 μl of a 4-fold excess ATP solution in kinase buffer is added to the 384-well assay plate. Final ATP concentration is typically set to the Km for ATP. The reaction is allowed to proceed for 60 minutes. During the kinase reaction, a stop solution consisting of EDTA and a Europium-containing phosphotyrosine antibody (Invitrogen Catalog #5692) is prepared in TR-FRET dilution buffer (Invitrogen Catalog #3574). The stop solution contains an EDTA concentration of 20 mM and an antibody concentration of 4 nM. After the 60 minute reaction, 10 µl of the stop solution is added to all wells. Each well is mixed and incubated for 30 minutes at room temperature. Plates are read on a Perkin Elmer Envision TR-FRET plate reader under LanthaScreen settings. Excitation wavelength is 337 nm and Emission wavelengths are 620 nm and 665 nm. Data are acquired as the ratio of emission at 665 nm/emission at 620 nm and plotted as a function of compound concentration to ascertain compound potency. Here, a signal is observed only when a Europium-coupled phophotyrosine antibody binds the phosphorylated peptide.

Example 3

BTK Radiometric Enzyme Assay

BTK activity is measured by product formation based on the incorporation of $^{33}PO_4$ from [33P]ATP into a biotin-tagged substrate peptide (see Dinh M., et. al. Activation mechanism and steady state kinetics of Bruton's tyrosine kinase. *J. Biol Chem.* 282:8768-76. 2007). The peptide Is isolated from unreacted [$^{33}$P]ATP using streptavidin-coated beads. Each well of a 96-well V bottom plate (Greiner, Monroe, N.C.), contains assay buffer (8 mM imidazole, pH 7.2, 8 mM glycerol 2-phosphate, 200 uM EGTA, 20 mM MgCl2, 1 mM $MnCl_2$, 0.1 mg/ml bovine serum albumin, and 2 mM dithiothreitol) which was combined to 40 ul with a mixture of substrates dissolved in assay buffer such that the final concentrations were 1 uCi of [$^{33}$P]ATP, 100 uM ATP, and peptide substrate (biotin-Aca-AAAEEIYGEI-NH2). Initiation of the reaction is by addition of BTK to a final concentration of 10 nM. The reaction is incubated at 30° C. for 15 min. The reaction is stopped by transferring 25 ul of sample to a 96-well 1.2-um hydrophilic polyvinylidene difluoride filter plate (Millipore, Billerica, Mass.) containing 10% streptavidin-Sepharose beads (GE Healthcare) dissolved in phosphate-buffered saline plus 50 mM EDTA. Filter plates are washed with 2 M NaCl, then with 2 M NaCl with 1% phosphoric acid, and then with $H_2O$. Plates were allowed to dry and microscint-20 (PerkinElmer Life Sciences, Boston, Mass.) was added. The [$^{33}$P] phosphoproduct is detected by a top-count scintillation counter. The enzyme activity is calculated for each data point. The corrected number of counts in each well is determined by subtracting the background counts from the measured counts. This value is then divided by the total number of counts that were originally present in the solution (determined by spotting and counting an equivalent volume of unwashed sample on a filter plate) and multiplied by the concentration of ATP in solution to give the concentration of phosphorylated product formed. Selectivity for Btk will be determined using commercially available kinase cross-screening services (DiscoveRx, San Diego, Calif.).

Example 4

BTK TR-FRET Assay

Inhibition of BTK enzymatic activity by compounds is measured using time-resolved fluorescence resonance energy transfer (TR-FRET) (Invitrogen pamphlet: Optimization of a LanthaScreen Kinase assay for BTK). Here, a signal is observed only when a Europium-coupled phophotyrosine antibody binds the phosphorylated peptide. Compounds are first prepared in 100% DMSO and serially diluted 10 times via 3-fold dilution. 2.5 ul of inhibitor at 4-fold the final assay concentration is next transferred to the 384-well assay plate (Corning Catalog #3676). A solution of 2-fold the final concentration of BTK enzyme (Invitrogen Catalog # PV3363) and Alexafluor 647-coupled peptide substrate (Invitrogen Catalog #5693) is next prepared in advance in a kinase buffer of 50 mM Hepes pH 7.5, 10 mM MgCl2, and 1 mM EGTA. For this solution, the final concentration of BTK and peptide is typically 1 nM and 100 nM, respectively. 5 uL of this 2-fold mix of BTK and peptide is added as the second step of the procedure to the 384-well assay plate. To initiate the enzymatic reaction, 2.5 ul of a 4-fold excess ATP solution in kinase buffer is added to the 384-well assay plate. Final ATP concentration is typically set to the Km for ATP of 100 uM. The reaction is allowed to proceed for 60 minutes. During the kinase reaction, a stop solution consisting of EDTA and a Europium-containing phosphotyrosine antibody (Invtrogen Catalog #5692) is prepared in TR-FRET dilution buffer (Invitrogen Catalog #3574). The stop solution contains an EDTA concentration of 20 mM and an antibody concentration of 4 nM. After the 60 minute reaction, 10 ul of the stop solution is added to all wells. Each well is mixed and incubated for 30 minutes at room temperature. Plates are read on a Perkin Elmer Envision TR-FRET plate reader under LanthaScreen settings. Excitation wavelength is 337 nm and Emission wavelengths are 620 nm and 665 nm. Data are acquired as the ratio of emission at 665 nm/emission at 620 nm and plotted as a function of compound concentration to ascertain compound potency. Here, a signal is observed only when a Europium-coupled phophotyrosine antibody binds the phosphorylated peptide.

Example 5

Cellular Btk Activity Measured by Reporter Assay in Ramos Cells

The beta lactamase-based select-screen reporter assay is used to measure Btk cell-based activity (Invitrogen Selectscreen Screening Protocol and Assay Conditions document. Revised 8 Feb. 2010). 32 µL of NFAT-bla RA1 (Invitrogen) cells diluted in Assay Media to appropriate cell density are added to the Poly-D-Lysine assay plate containing 4 µL of a 10x serial dilution of a Btk control compound or test compounds. Pre-incubation at 37° C./5% CO2 in a humidified incubator with compounds and control inhibitor titration is for 30 minutes. 4 µL of 10x control activator Goat anti-Human IgM at the pre-determined EC80 concentration is added to wells containing the control inhibitor or compounds. The plate is incubated for 5 hours at 37° C./5% CO2 in a humidified incubator. 8 µL of 1 µM Substrate Loading Solution is added to each well and the plate is incubated for 2 hours at room temperature. The plate is read on a fluorescence plate reader and the data is analyzed. A response ratio is calculated from the emissions of cleaved and uncleaved substrate. The response ratio of wells with compound dilutions is compared with wells that contain only DMSO to calculate the percent inhibition at each compound concentration. A dose response curve is constructed and an $IC_{50}$ is calculated.

Example 6

Blockade of CD69 Expression in Whole Blood Samples

Activation of the B cell receptor leads to increased Btk activity, calcium mobilization and B cell activation (see Honigberg L. A., et. al. *Proc Natl Acad Sci USA* 107:13075-80. 2010). Btk inhibitors have been shown to block B cell activation as measured by CD69 expression (see Karp, R., et al. Inhibition of Btk with AVL-292 Translates to Protective Activity in Animal Models of Rheumatoid Arthritis. Inflammation Research Association Meeting, September, 2010). We used expression of CD69 following B cell activation as a measure of Btk activity in whole blood. Aliquots of whole blood are pre-incubated with serial dilutions of test compound for 30 minutes followed by activation with anti-IgM (goat Fab'2, 50 ug/ml). Samples are incubated overnight at 37 C and then stained with PE labeled anti-CD20 and APC labeled anti-CD69 (BD Pharmingen) for 30 minutes according to the manufacturer's directions. Whole blood is then lysed and cells gated on CD20 expression are quantified for CD 69 expression by FACS. The percent inhibition is calculated based on a DMSO control for no inhibition and plotted as a function of test compound concentration from which an $IC_{50}$ value is calculated.

Example 7

Inhibition of Mouse Collagen-induced Arthritis

Inhibition of murine collagen-induced arthritis (mCIA) is a standard animal disease model for rheumatoid arthritis. Previous studies have demonstrated that inhibition of Btk is efficacious in blocking mCIA (see Honigberg L. A., et. al. *Proc Nail Acad Sci USA*. 107:13075-80. 2010). Starting on day 0 DBA/1 mice are injected with an emulsion of Type II collagen in Complete Freund's Adjuvant. Mice are boosted 21 days later to synchronize development of disease. After development of mild disease, animals are enrolled in the study and randomized. Dosing is oral, Q.D. typically for 11 days with test compound or dexamethasone (0.2 mg/kg) as control. One group receives vehicle alone. Clinical scoring (0-4) is based on the extent of swelling and severity of arthritis. Scores for all four paws are added for maximum score of 16. Anti-collagen antibodies and total Ig are measured for each animal by Elisa at the end of the study (Bolder BioPath, Boulder, Colo.).

FORMULATION EXAMPLES

The following are representative pharmaceutical formulations containing a compound of Formula (I).

Tablet Formulation

The following ingredients are mixed intimately and pressed into single scored tablets.

| Ingredient | Quantity per tablet mg |
|---|---|
| compound of this disclosure | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per capsule mg |
|---|---|
| compound of this disclosure | 200 |
| lactose spray dried | 148 |
| magnesium stearate | 2 |

Injectable Formulation

Compound of the disclosure (e.g., compound 1) in 2% HPMC, 1% Tween 80 in DI water, pH 2.2 with MSA, q.s. to at least 20 mg/mL The foregoing disclosure has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the disclosure should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed:

1. A compound of Formula (I):

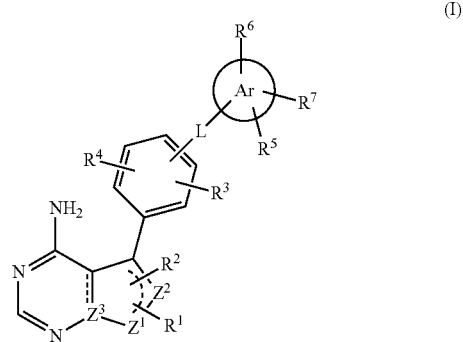

wherein:

the dashed lines are independently an optional bond;

$Z^1$, $Z^2$, and $Z^3$ are —N— or CH, provided that at least one and not more than two of $Z^1$, $Z^2$, and $Z^3$ are simultaneously N;

L is O, CO, $CH_2$, S, SO, $SO_2$, NR, NRCO, CONR, NR'$SO_2$, $SO_2$NR', or NRCONR', where each R and R' is independently hydrogen, alkyl, or cycloalkyl;

Ar is aryl, heteroaryl, cycloalkyl or heterocyclyl;

one of $R^1$ and $R^5$ is hydrogen, alkyl, hydroxy, cyano, alkoxy, halo, haloalkyl, or haloalkoxy and the other of $R^1$ and $R^5$ is:

formula (a) or (b);

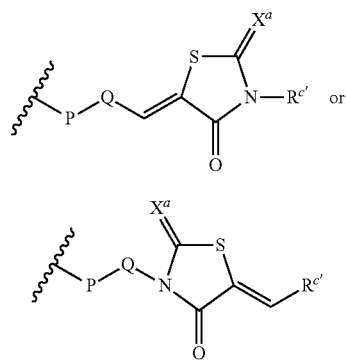

where P is a bond, $NR^a$ (where $R^a$ is hydrogen or alkyl), —O—, S, SO, $SO_2$, alkylene or heteroalkylene;

Q is a bond, aryl or heteroaryl wherein aryl or heteroaryl is optionally substituted with one or two substituents independently selected from hydrogen, halo, alkyl, alkoxy, alkylthio, haloalkyl, or haloalkoxy;

$X^a$ is O, S, N(H), or N(alkyl);

$R^{c'}$ is hydrogen, alkyl, substituted alkyl, haloalkoxy, cycloalkyl, or cycloalkyleneNR$^d$R$^e$ where $R^d$ and $R^e$ are independently hydrogen, alkyl, or cycloalkyl;

$R^2$ is hydrogen, alkyl, hydroxy, alkoxy, cyano, halo or haloalkyl;

$R^3$ and $R^4$ are independently hydrogen, alkyl, cycloalkyl, hydroxy, alkoxy, cyano, halo, haloalkyl or haloalkoxy; and $R^6$ and $R^7$ are independently hydrogen, alkyl, hydroxy, alkoxy, halo, haloalkyl, haloalkoxy, carboxy, alkoxycarbonyl, cyano, —$CONH_2$, amino, monosubstituted or disubstituted amino;

or a pharmaceutically acceptable salt thereof.

2. The compound of claim 1 or a pharmaceutically acceptable salt thereof wherein:

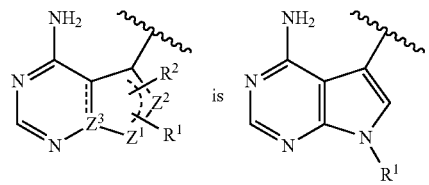

3. The compound of claim 1 or a pharmaceutically acceptable salt thereof wherein:

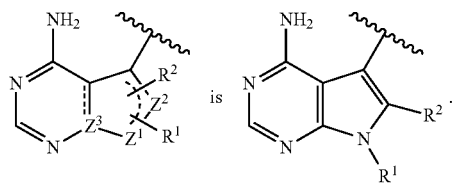

4. The compound of claim 2 or a pharmaceutically acceptable salt thereof wherein L is O, S, NH, N(methyl), NHCO, CONH, or NHCONH.

5. The compound of claim 3 or a pharmaceutically acceptable salt thereof wherein L is O, S, NH, N(methyl), NHCO, CONH, or NHCONH.

6. The compound of claim 1 or a pharmaceutically acceptable salt thereof wherein $R^3$ and $R^4$ are independently hydrogen, methyl, fluoro, methoxy, chloro, trifluoromethyl, or trifluoromethoxy.

7. The compound of claim 4 or a pharmaceutically acceptable salt thereof wherein $R^3$ and $R^4$ are independently hydrogen, methyl, fluoro, methoxy, chloro, trifluoromethyl, or trifluoromethoxy.

8. The compound of claim 5 or a pharmaceutically acceptable salt thereof wherein $R^3$ and $R^4$ are independently hydrogen, methyl, fluoro, methoxy, chloro, trifluoromethyl, or trifluoromethoxy.

9. The compound of claim 6 or a pharmaceutically acceptable salt thereof wherein $R^6$ and $R^7$ are independently hydrogen, methyl, methoxy, fluoro, chloro, trifluoromethyl, trifluoromethoxy, or cyano.

10. The compound of claim 7 or a pharmaceutically acceptable salt thereof wherein $R^5$ is hydrogen, methyl, methoxy, fluoro, chloro, trifluoromethyl, trifluoromethoxy or cyano;

$R^1$ is formula (a)

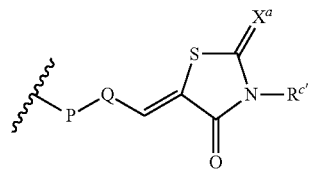

where $X^a$ is O, S, N(H) or N(alkyl);

$R^{c'}$ is hydrogen, alkyl, cycloalkyl, substituted alkyl or cycloalkyleneNR$^d$R$^e$;

$R^6$ and $R^7$ are independently hydrogen, methyl, methoxy, fluoro, chloro, trifluoromethyl, trifluoromethoxy, or cyano; and L is O.

11. The compound of claim 8 or a pharmaceutically acceptable salt thereof wherein $R^5$ is hydrogen, methyl, methoxy, fluoro, chloro, trifluoromethyl, trifluoromethoxy, or cyano;

$R^1$ is formula (a)

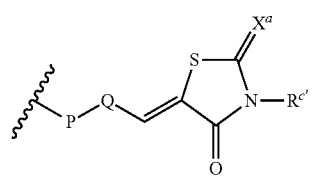

where $X^a$ is O, S, N(H) or N(alkyl);

$R^{c'}$ is hydrogen, alkyl, cycloalkyl, substituted alkyl or cycloalkyleneNR$^d$R$^e$;

$R^6$ and $R^7$ are independently hydrogen, methyl, methoxy, fluoro, chloro, trifluoromethyl, trifluoromethoxy, or cyano; and L is O.

12. The compound of claim 7 or a pharmaceutically acceptable salt thereof wherein $R^5$ is hydrogen, alkyl, hydroxy, alkoxy, halo, haloalkyl, or haloalkoxy;

R¹ is formula (b)

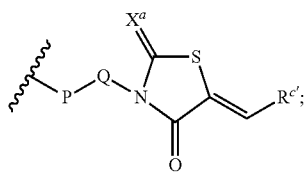

R⁶ and R⁷ are independently hydrogen, methyl, methoxy, fluoro, chloro, trifluoromethyl, or trifluoromethoxy; and
L is O.

13. The compound of claim 8 or a pharmaceutically acceptable salt thereof wherein R⁵ is hydrogen, alkyl, hydroxy, alkoxy, halo, haloalkyl, or haloalkoxy;

R¹ is formula (b);

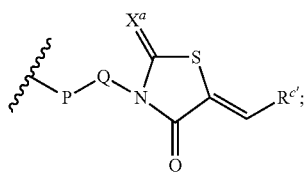

R⁶ and R⁷ are independently hydrogen, methyl, methoxy, fluoro, chloro, trifluoromethyl, or trifluoromethoxy; and
L is O.

14. The compound of claim 12 or a pharmaceutically acceptable salt thereof wherein $X^a$ is O;

R^{c'} is ethyl, propyl, cyclopropyl, or alkyl substituted with hydroxyl, alkoxy, alkylamino or dialkylamino;

P is alkylene; and

Q is a bond.

15. The compound of claim 13 or a pharmaceutically acceptable salt thereof wherein $X^a$ is O;

R^{c'} is ethyl, propyl, cyclopropyl, or alkyl substituted with hydroxyl, alkoxy, alkylamino or dialkylamino;

P is alkylene; and

Q is a bond.

16. The compound of claim 9 or a pharmaceutically acceptable salt thereof wherein the

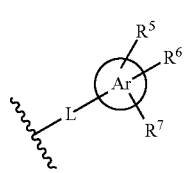

group is attached at the 4-position of the phenyl ring, the carbon atom of the phenyl ring attached to

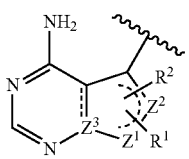

being carbon 1; and

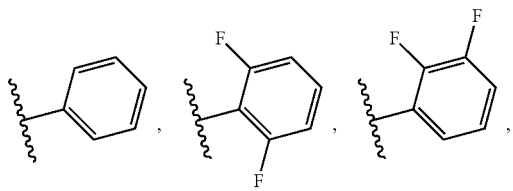

is selected from

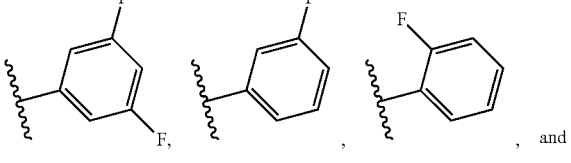

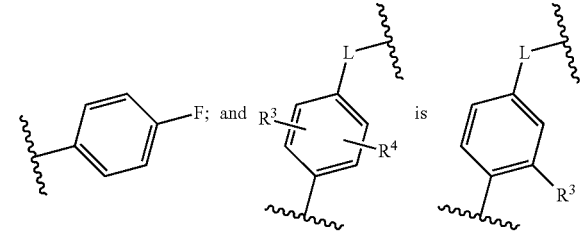

where R³ is hydrogen or fluoro.

17. The compound of claim 14 or a pharmaceutically acceptable salt thereof wherein the

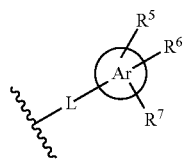

group is attached at the 4-position of the phenyl ring, the carbon atom of the phenyl ring attached to

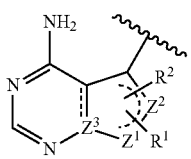

being carbon 1; and

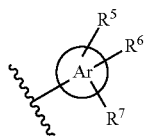

is selected from

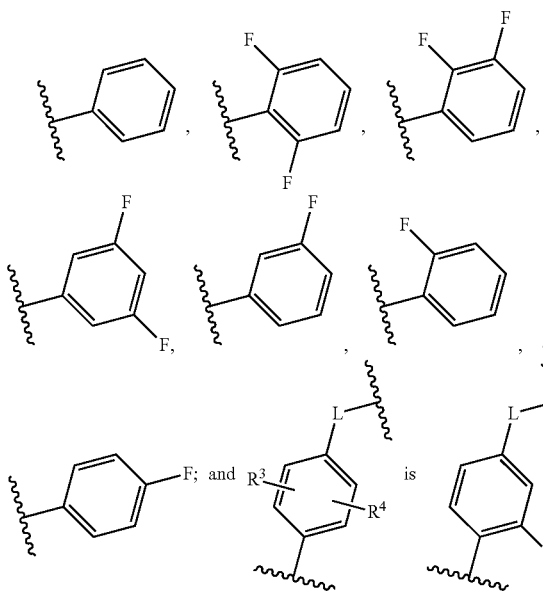

where R³ is hydrogen or fluoro.

18. The compound of claim 15 or a pharmaceutically acceptable salt thereof wherein the

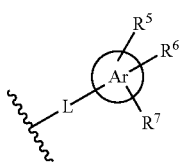

group is attached at the 4-position of the phenyl ring, the carbon atom of the phenyl ring attached to

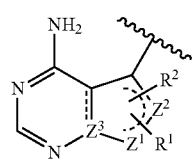

being carbon 1; and

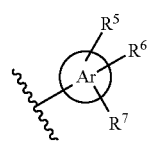

is selected from

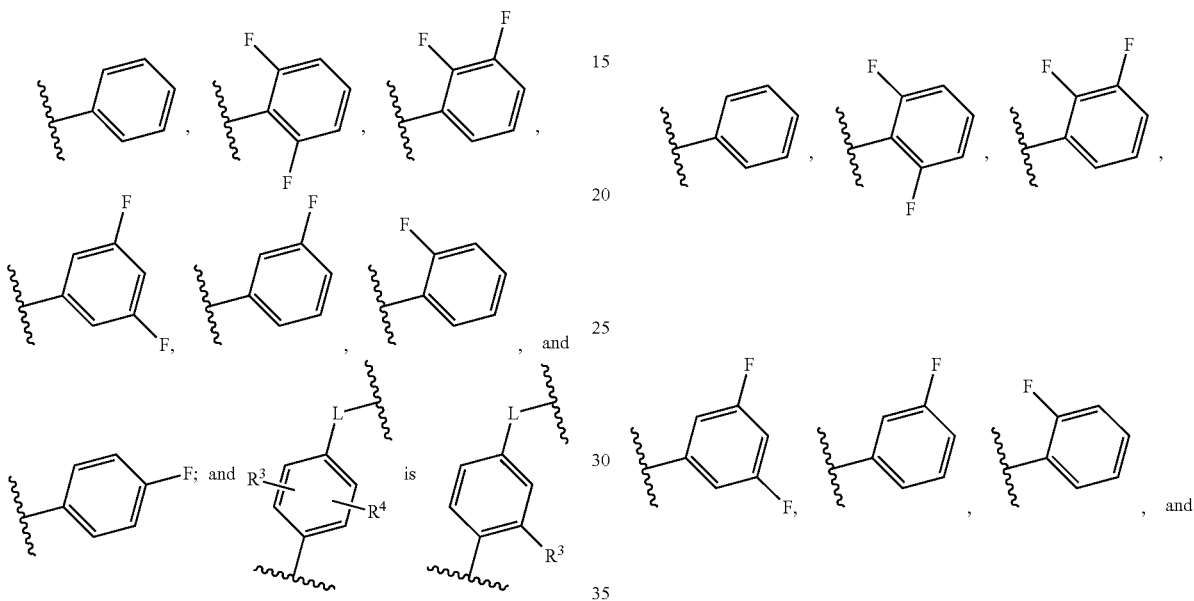

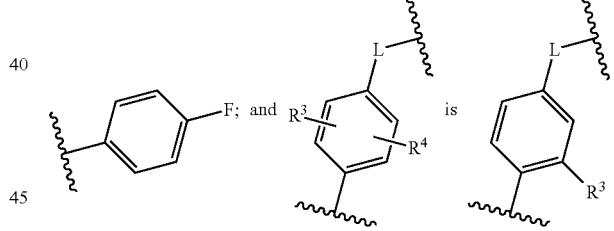

where R³ is hydrogen or fluoro.

19. A pharmaceutical composition comprising a compound of claim 1 or a pharmaceutically acceptable salt thereof; and a pharmaceutically acceptable excipient.

20. A method of treating chronic lymphocytic leukemia or mantle cell lymphoma in a patient which method comprises administering to the patient in need thereof, a pharmaceutical composition comprising a compound of claim 1 or a pharmaceutically acceptable salt thereof and a pharmaceutically acceptable exciplent.

* * * * *